United States Patent [19]
Acton

[11] Patent Number: 6,153,417
[45] Date of Patent: Nov. 28, 2000

[54] CSAPK-1 PROTEIN AND USES THEREFOR

[75] Inventor: Susan Acton, Lexington, Mass.

[73] Assignee: Millennium Pharmaceuticals, Inc., Cambridge, Mass.

[21] Appl. No.: 09/221,416

[22] Filed: Dec. 28, 1998

Related U.S. Application Data

[62] Division of application No. 09/163,115, Sep. 29, 1998.
[60] Provisional application No. 60/099,657, Sep. 9, 1998.

[51] Int. Cl.$^7$ ............................. C12N 9/12; C07H 21/04; C07K 1/00
[52] U.S. Cl. ......................... 435/194; 536/23.2; 530/350
[58] Field of Search ........................... 435/194; 536/23.2; 530/350

[56] References Cited

U.S. PATENT DOCUMENTS 5,928,874   7/1999   Bandman et al. ............................ 435/6

OTHER PUBLICATIONS

GenBank™ Accession Number AA746653 for Homo Sapiens cDNA clone 1257327; Jan. 22, 1990.
GenBank™ Accession Number AA937590 for Homo Sapiens cDNA clone 1425841; Aug. 24, 1998.
GenBank™ Accession Number AA503192 for Homo Sapiens cDNA clone 956612; Aug. 20, 1997
GenBank™ Accession Number B38320 for Homo sapiens genomic clone Plate=CT 830 Col=16 Row=0; Oct. 17, 1997.
GenBank™ Accession Number AL023513 for Human DNA sequence for clone268D13; Sep. 23, 1998.
GenBank™ Accession Number G21973 for Human STS WI–15835; May 31, 1996.
GenBank™ Accession Number AA399022 for Soares testis–NHT Homo sapiens cDNA clone 729929; May 16, 1997.
GenBank™ Accession Number AA516800 for Barstead mouse mytotubes MPLRB5 Mus musculus cDNA clone 902193; Jul. 14, 1997.
GenBank™ Accession Number Q09298 for Hypothetical 141.2 KD Pritein EEED8.9; Jul. 15, 1998.
GenBank™ Accession Number AA307961 for Colon carcinoma (HCC) cell line II Homo sapiens cDNA; Apr. 18, 1997.
GenBank™ Accession Number AA307684 for Colon carcinoma (HCC) cell line II Homo sapiens cDNA; Apr. 18, 1997.
GenBank™ Accession Number AA310905 Jurkat T–cells V Homo Sapiens cDNA; Apr. 19, 1997.

Adams, M.D. et al., "Initial Assessment of Human Gene Diversity and Expression Patterns Based Upon 83 Million Nucleotides of cDNA Sequence," Nature vol. 377 (supp), 3–174 (1995).
Claverie, J–M. et al., "Alu Alert," Nature vol. 371, 752 (1994).
Deiss, L.P. et al., "Identification of a Novel Serine/Threonine Kinase and a Novel 15–kd protein as Potential Mediaters of the Gamma Interferon–Induced Cell death," Genes Dev. vol. 9 No. 1 15–30 (1995).
Dorow, D.S. et al., "Identification of a New Family of Human Epithelial Protein Kinases Containing Two Leucine/isoleucine–Zipper Domains," Eur. J. Biochem. vol. 213 No. 2, 701–710 (1993).
Jurka, J. et al., "Reconstruction and Analysis of human Alu Genes," J. Mol. Evol. vol. 32, No. 2, 105–121 (1991).
Katoh, M. et al., "CloOning and Characterization of MST, a Novel (Putative) Serine/Threonine Kinase with SH3 Domain," Oncogene vol. 10, No. 7, 1447–1451 (1995).
Kawai, T. et al., "Zip–Kinase, a Novel Serine.Threonine Kinase which Medites Apoptosis," Mol. Cell. Biol. vol. 18, 1642–1651 (1998).
Nagase, T. et al., "Prediction of the Coding Sequences of Unidentified Human Genes. IX. The Complete Sequence of 100 New cDNA Clones From the Brain which Can Code for Large Proteins in Vitro," DNA Res. vol. 5, 31–39 (1998).
Schultz, S.J. et al., "Identification of 21 Novel Human Protein Kinases, Including 3 Members of a Family Related to the Cell Cycle Regulator nimA of Aspergillus Nidulans," Cell Growth Differ. vol. 4, No. 10, 821–830 (1993).
Schultz, S.J. et al., "Cell Cycle–Dependant Expression of Nek2, a Novel Human Protein Kinase Related to the NIMA Mitotic Regulator of Aspergillus Nidulans," Cell Growth Differ. vol. 5, No. 6, 625–635 (1994).
Su, Y.C. et al., NIK is a New ste20–Related Kinase That Binds NCK and MEKK1 and activates the SAPK/JNK cascade via a Conserved Regulatory Domain.
Wilson, R. et al., "2.2 Mb of Contiguous Nucleotide Sequence from Chromosome III of C. elegans," Nature vol. 368 No. 6466, 32–38 (1994).

*Primary Examiner*—Rebecca E. Prouty
*Assistant Examiner*—M. Monshipouri
*Attorney, Agent, or Firm*—Lahive & Cockfield, LLP; Amy E. Mandragouras

[57] ABSTRACT

The present invention provides a novel protein kinase, CSAPK-1, as well as CSAPK-1 fusion proteins, antigenic peptides and anti-CSAPK-1 antibodies.

13 Claims, 11 Drawing Sheets

```
TCGACCCACGCGTCCGGGAGGATCGGGAGTCGCGGGAGGATGGGCCGCCGCTAGGCTCGCACTCCGGA
CGCGCCTCGC
AGTGCGCAGGGTGGGTGCCCCGCGCCTGCAGCGTCCGCCGGGGCGGCGCGGCGGGAGGTGGCCGACAG
GCTCCGGGCC
TCGCAGCCTCAGCCCCCGGCCCAGCGCGCTTTCCGACGGCGGCGCCGCGCCGAGCCACCCGCC
CGCCCAAGGTCTCTCGCGGGCGGGAGAACGGAAAACTCCCAACTTCCTGAGTTCTAAAGTTCCTGTTG
CTTCAGACAA
TGGATGAGCAATCACAAGGAATGCAAGGGCCACCTGTTCCTCAGTTCCAACCACAGAAGGCCTTACGA
CCGGATATGG
GCTATAATACATTAGCCAACTTTCGAATAGAAAAGAAAATTGGTCGCGGACAATTTAGTGAAG
TTTATAGAGCAGCCTGTCTCTTGGATGGAGTACCAGTAGCTTTAAAAAAAGTGCAGATATTTGATTTA
ATGGATGCCA
AAGCACGTGCTGATTGCATCAAAGAAATAGATCTTCTTAAGCAACTCAACCATCCAAATGTAATAAAA
TATTATGCAT
CATTCATTGAAGATAATGAACTAAACATAGTTTTGGAACTAGCAGATGCTGGCGACCTATCCA
GAATGATCAAGCATTTTAAGAAGCAAAAGAGGCTAATTCCTGAAAGAACTGTTTGGAAGTATTTTGTT
CAGCTTTGCA
GTGCATTGGAACACATGCATTCTCGAAGAGTCATGCATAGAGATATAAAACCAGCTAATGTGTTCATT
ACAGCCACTG
GGGTGGTAAAACTTGGAGATCTTGGGCTTGGCCGGTTTTTCAGCTCAAAAACCACAGCTGCAC
ATTCTTTAGTTGGTACGCCTTATTACATGTCTCCAGAGAGAATACATGAAAATGGATACAACTTCAAA
TCTGACATCT
GGTCTCTTGGCTGTCTACTATATGAGATGGCTGCATTACAAAGTCCTTTCTATGGTGACAAAATGAAT
TTATACTCAC
TGTGTAAGAAGATAGAACAGTGTGACTACCCACCTCTTCCTTCAGATCACTATTCAGAAGAAC
TCCGACAGTTAGTTAATATGTGCATCAACCCAGATCCAGAGAAGCGACCAGACGTCACCTATGTTTAT
GACGTAGCAA
AGAGGATGCATGCATGCACTGCAAGCAGCTAAACATGCAAGATCATGAAGAGTGTAACCAAAGTAATT
GAAAGTATTT
TGTGCAAAGTCGTACCTSCCCATTTATGTCTGGGTGTTAAGATTAATATTTCAGAGCTAGTGT
GCTCTGAATCCTTAACCAGTTTTCATATAAGCTTCATTTTGTACCAGTCACCTAAATCACCTCCTTGC
AACCCCCAAA
TGACTTTGGAATAACTGAATTGCATGTTAGGAGAGAAAATGAAACATGATGGTTTTGAATGGCTAAAG
GTTTATAGAA
TTTCTTACAGTTTTCTGCTGATAAATTGTGTTTAGATAGACTGTCAGTGCCAAATATTGAAGG
TGCAGCTTGGCACACATCAGAATAGACTCATACCTGAGAAAAAGTATCTGAACATGTGACTTGTTTCT
TTTTTAGTAA
TTTATGGACATTGAGATGAACACAATTGTGAACTTTTGTGAAGATTTTATTTTTAAACGTTTGAAGTA
CTAGTTTTAG
TTCTTAGCAGAGTAGTTTTCAAATATGATTCTTATGATAAATGTAGACACAAACTATTTGAGA
AACATTTAGAACTCTTAGCTTATACATTCAAAATGTAACTATTAAATGTGAAGATTTGGGGACAAAAT
GTGAGTCAGA
CACTGAAGAGTTTTTTGTTTTGTTTTAATATTTTTGATATTCTCTTTGCATTGAAATGGTATAAATGA
ATCCATTTAA
AAAGTGGTTAAGGATTTGTTTAGCTGGTGTGATAATAATTTTTAAAGTTGCACATTGCCCAAG
GCTTTTTTTGTGTGTTTTTATTGTTGTTTGTACATTTGAAAAATATTCTTTGAATAACCTTGCAGTAC
TATATTTCAA
```

Fig. 1

```
TTTCTTTATAAATTTAAGTGCATTTTAACTCATAATTGTACACTATAATATAAGCCTAAGTTTTTATT
CATAAGTTTT
ATTGAAGTTCTGATCGGTCCCCTTCAGAAATTTTTTTATATTATTCTTCAAGTTACTTTCTTA
TTTATATTGTATGTGCATTTTATCCATTAATGTTTCATACTTTCTGAGAGTATAATACCCTTTTAAAA
GATATTTGGT
ATACCAATACTTTTCCTGGATTGAAAACTTTTTTTAAACTTTTTAAAATTTGGGCCACTCTGTATGCA
TATGTTTGGT
CTTGTTAAAGAGGAAGAAAGGATGTGTGTTATACTGTACCTGTGAATGTTGATACAGTTACAA
TTTATTTGACAAGGTTGTAATTCTAGAATATGCTTAATAAAATGAAAACTGGCCATGACTACAGCCAG
AACTGTTATG
AGATTAACATTTCTATTGAGAAGCTTTTGAGTAAAGTACTGTATTTGTTCATGAAGATGACTGAGATG
GTAACACTTC
GTGTAGCTTAAGGAAATGGGCAGAATTTCGTAAATGCTGTTGTGCAGATGTGTTTTCCCTGAA
TGCTTTCGTATTAGTGGCGACCAGTTTCTCACAGAATTGTGAAGCCTGAAGGCCAAGAGGAAGTCACT
GTTAAAGGAC
TCTGTGCCATCTTACAACCTTGGATGAATTATCCTGCCAACGTGAAAACCTCATGTTCAAAGAACACT
TCCCTTTAGC
CGATGTAACTGCTGGTTTTGTTTTTCATATGTGTTTTTCTTACACTCATTTGAATGCTTTCAA
GCATTTGTAAACTTAAAAAAAANWAWAAAGGGCAAAAAGTCTGAACCCTTGTTTTCTGAAATCTAATC
AGTTATGTAT
GGTTTCTGAAGGGTAATTTTATTTTGGAATAGGTAAAGCGAAACCTGTTTTGTCWTGTTTTTCCTGAG
GGCTAGATGC
ATTTTTTTTCTCACACTCTTAATGACTTTTAACATTTATACTGAGCATCCATAGATATATTCC
TAGAAGTATGAGAAGAATTATTCTTATTGACCATTAATGTCATGTTCATTTTAATGTAATATAATTGA
GATGAAATGT
TCTCTGGTTGGAACAGATACTCTCTTTTTTTTTCTTGCAATCTTTAAGAATACATAGATCTAAAATTC
ATTAGCTTGA
CCCCTCAAAGTAACTTTTAAGTAAAGATTAAAGCTTTTCTTCTCAGTGAATATATCTGCTAGA
AGGAAATAGCTGGGAAGAATTTAATGATCAGGGAAATTCATTATTTCTATATGTGGAAACTTTTTGCT
TCGAATATTG
TATCTTTTTAAATCTAAATGTTCATATTTTTCCTGAAGAAACCACTGTGTAAAAATCAAATTTTAATT
TTGAATGGAA
TAATTTCAAAGAACTATGAAGATGATTTGAAGCTCTAATTTATATAGTCACCTATAAAATGTT
CTTTATATGTGTTCATAAGTAAATTTTATATTGATTAAGTTAAACTTTTGAATTGATTTGAGGAGCAG
TAAAATGAAA
GCTATATCTATTNCTAAACCYTATTTAGACATTGGKACCAGTTACCCAGGTGAAAATAKGGAGTAACT
TTGTTTTGTA
TGGTAAGGTTTAGGAATGGNGGATGAAGGGTATCTCTATATAAATAAAGTGCTCAACAATGTG
CAATGATTGTAAATTTAGTAAGATATTACAGCCATTTCATGAATGCTTTACCATTCAACATAGTATCT
ATTACAAAAC
ACCTTTCTTGTATCCATATACTTCAGGTGTTGCTGTTAACATTTACTATGATATTTATTTTAACCAAA
ATGTTACTCA
CATTAAATGTTTATTCTTTAAAATGAATGTATTATGTTTTTAACCCACAAATGCATACTTACC
CTGTGCCTCATATTTCAATAGTACTGTAATATGGACATCTTTTGTGAAATACTTTTATTTTGTTATGC
TTTAAATATA
CATACAAAAGATTTCTGTTATTAGCTTTGAAAATTGTATAATATCCTAATATAAACAAAAATATAAA
AATAAAAATG
AATACAGTAAAAAAAAAAAAAAAAAAAAAAAAAAAAAGG
```

Fig. 1 (continued)

MDEQSQGMQGPPVPQFQPQKALRPDMGYNTLANFRIEKKIGRGQFSEVYRAACLLDGVPVALKKVQIF
DLMDAKARAD
CIKEIDLLKQLNHPNVIKYYASFIEDNELNIVLELADAGDLSRMIKHFKKQKRLIPERTVWKYFVQLC
SALEHMHSRR
VMHRDIKPANVFITATGVVKLGDLGLGRFFSSKTTAAHSLVGTPYYMSPERIHENGYNFKSDI
WSLGCLLYEMAALQSPFYGDKMNLYSLCKKIEQCDYPPLPSDHYSEELRQLVNMCINPDPEKRPDVTY
VYDVAKRMHA
CTASS

Fig. 1 (continued)

```
GTCGACCCACGCGTCCGGTGGAAGTATAATACTTTGTCATTATGAGATGTCGTCTCTCGG
TGCCTCCTTTGTGCAAATTAAATTTGATGACTTGCAGTTTTTTGAAAACTGCGGTGGAGG
AAGTTTTGGGAGTGTTTATCGAGCCAAATGGATATCACAGGACAAGGAGGTGGCTGTAAA
GAAGCTCCTCAAAATAGAGAAAGAGGCAGAAATACTCAGTGTCCTCAGTCACAGAAACAT
CATCCAGTTTTATGGAGTAATTCTTGAACCTCCCAACTATGGCATTGTCACAGAATATGC
TTCTCTGGGATCACTCTATGATTACATTAACAGTAACAGAAGTGAGGAGATGGATATGGA
TCACATTATGACCTGGGCCACTGATGTAGCCAAAGGAATGCATTATTTACATATGGAGGC
TCCTGTCAAGGTGATTCACAGAGACCTCAAGTCAAGAAACGTTGTTATAGCTGCTGATGG
AGTACTGAAGATCTGTGACTTTGGTGCCTCTCGGTTCCATAACCATACAACACACATGTC
CTTGGTTGGAACTTTCCCATGGATGGCTCCAGAAGTTATCCAGAGTCTCCCTGTGTCAGA
AACTTGTGACACATATTCCTATGGTGTGGTTCTCTGGGAGATGCTAACAAGGGAGGTCCC
CTTTAAAGGTTTGGAAGGATTACAAGTAGCTTGGCTTGTAGTGGAAAAAAACGAGAGATT
AACCATTCCAAGCAGTTGCCCCAGAAGTTTTGCTGAACTGTTACATCAGTGTTGGGAAGC
TGATGCCAAGAAACGGCCATCATTCAAGCAAATCATTTCAATCCTGGAGTCCATGTCAAA
TGACACGAGCCTTCCTGACAAGTGTAACTCATTCCTACACAACAAGGCGGAGTGGAGGTG
CGAAATTGAGGCAACTCTTGAGAGGCTAAAGAAACTAGAGCGTGATCTCAGCTTTAAGGA
GCAGGAGCTTAAAGAACGAGAAAGACGTTTAAAGATGTGGGAGCAAAAGCTGACAGAGCA
GTCCAACACCCCGCTTCTCTTGCCTCTTGCTGCAAGAATGTCTGAGGAGTCTTACTTTGA
ATCTAAAACAGAGGAGTCAAACAGTGCAGAGATGTCATGTCAGATCACAGCAACAAGTAA
CGGGGAGGGCCATGGCATGAACCCAAGTCTGCAGGCCATGATGCTGATGGGCTTTGGGGA
TATCTTCTCAATGAACAAAGCAGGAGCTGTGATGCATTCTGGGATGCAGATAAACATGCA
AGCCAAGCAGAATTCTTCCAAAACCACATCTAAGAGAAGGGGGAAGAAAGTCAACATGGC
TCTGGGGTTCAGTGATTTTGACTTGTCAGAAGGTGACGATGATGATGATGATGACGGTGA
GGAGGAGGATAATGACATGGATAATAGTGAATGAAAGCAGAAAGCAAAGTAATAAAATCA
CAAATGTTTGGAAAACACAAAAGTAACTTGTTTATCTCAGTCTGTACAAAAACAGTAAGG
AGGCAGAAAGCCAAGCACTGCATTTTTAGGCCAATCACATTTACATGACCGTAATTTCTT
ATCAATTCTACTTTTATTTTTGCTTACAGAAAAACGGGGGGAGAATTAAGCCAAAGAAGT
ATATTTATGAATCAGCAAATGTGGTGCCTGATTATAGAAATTTGTGATCCTATATACAAT
ATAGGACTTTTAAAGTTGTGACATTCTGGCTTTTTCTTTTAATGAATACTTTTTAGTTTG
TATTTGACTTTATTTCCTTTATTCAAATCATTTTTAAAAACTTACATTTTGAACAAACAC
TCTTAACTCCTAATTGTTCTTTGACACGTAGTAATTCTGTGACATACTTTTTTTTTCTTA
TAGCAATACACTGTAATATCAGAAATGGTTGGCCTGAGCAACCTAGTAAGACCTCGTCTC
TACTAATAATTAAAAAACTAGCTGGCATGGTAGCACACACCTGTAGTCCCAGATACTTGG
GAGGCCAAGGCAGGAGGATTGCTTGAGACCTAGCAATCAGTCAGGGCTGCAGTGAGCCAT
GATGGCACCACTGCACTCTAGCCTGGGCAAGAGAACAAGATCCTGTCTCAAAAAACAAAA
AAAAAAAAAAGGGCGGCCG
```

MSSLGASFVQIKFDDLQFFENCGGGSFGSVYRAKWISQDKEVAVK
KLLKIEKEAEILSVLSHRNIIQFYGVILEPPNYGIVTEYASLGSLYDYINSNRSEEMDMD
HIMTWATDVAKGMHYLHMEAPVKVIHRDLKSRNVVIAADGVLKICDFGASRFHNHTTHMS
LVGTFPWMAPEVIQSLPVSETCDTYSYGVVLWEMLTREVPFKGLEGLQVAWLVVEKNERL
TIPSSCPRSFAELLHQCWEADAKKRPSFKQIISILESMSNDTSLPDKCNSFLHNKAEWRC
EIEATLERLKKLERDLSFKEQELKERERRLKMWEQKLTEQSNTPLLLPLAARMSEESYFE
SKTEESNSAEMSCQITATSNGEGHGMNPSLQAMMLMGFGDIFSMNKAGAVMHSGMQINMQ
AKQNSSKTTSKRRGKKVNMALGFSDFDLSEGDDDDDDDGEEEDNDMDNSE

Fig. 2

```
CGGTGGTGGCGGCAGCGGCGGCTGCGGGGGCACCGGGCCGCGGCGCCACCATGGCCGTGC
GACAGGCGCTGGGCCGCGGCCTGCAGCTGGGTCGAGCGCTGCTGCTGCGCTTCACGGGCA
AGCCCGGCCGGGCCTACGGCTTGGGGCGGCCGGGCCCGGCGGCGGGCTGTGTCCGCGGGG
AGCGTCCAGGCTGGGCCGCAGGACCGGGCGCGGAGCCTCGCAGGGTCGGGCTCGGGCTTC
CTAACCGTCTCCGCTTCTTCCGCCAGTCGGTGGCCGGGCTGGCGGCGCGGTTGCAGCGGC
AGTTCGTGGTGCGGGCCTGGGGCTGCGCGGGCCCTTGCGGCCGGGCAGTCTTTCTGGCCT
TCGGGCTAGGGCTGGGCCTCATCGAGGAAAAACAGGCGGAGAGCCGGCGGGCGGTCTCGG
CCTGTCAGGAGATCCAGGCAATTTTTACCCAGAAAAGCAAGCCGGGGCCTGACCCGTTGG
ACACGAGACGCTTGCAGGGCTTTCGGCTGGAGGAGTATCTGATAGGGCAGTCCATTGGTA
AGGGCTGCAGTGCTGCTGTGTATGAAGCCACCATGCCTACATTGCCCCAGAACCTGGAGG
TGACAAAGAGCACCGGGTTGCTTCCAGGGAGAGGCCCAGGTACCAGTGCACCAGGAGAAG
GGCAGGAGCGAGCTCCGGGGGCCCCTGCCTTCCCCTTGGCCATCAAGATGATGTGGAACA
TCTCGGCAGGTTCCTCCAGCGAAGCCATCTTGAACACAATGAGCCAGGAGCTGGTCCCAG
CGAGCCGAGTGGCCTTGGCTGGGGAGTATGGAGCAGTCACTTACAGAAAATCCAAGAGAG
GTCCCAAGCAACTAGCCCCTCACCCCAACATCATCCGGGTTCTCCGCGCCTTCACCTCTT
CCGTGCCGCTGCTGCCAGGGGCCCTGGTCGACTACCCTGATGTGCTGCCCCTCACGCCTCC
ACCCTGAAGGCCTGGGCCATGGCCGGACGCTGTTCCTCGTTATGAAGAACTATCCCTGTA
CCCTGCGCCAGTACCTTTGTGTGAACACACCCAGCCCCCGCCTCGCCGCCATGATGCTGC
TGCAGCTGCTGGAAGGCGTGGACCATCTGGTTCAACAGGGCATCGCGCACAGAGACCTGA
AATCCGACAACATCCTTGTGGAGCTGGACCCAGACGGCTGCCCCTGGCTGGTGATCGCAG
ATTTTGGCTGCTGCCTGGCTGATGAGAGCATCGGCCTGCAGTTGCCCTTCAGCAGCTGGT
ACGTGGATCGGGGCGGAAACGGCTGTCTGATGGCCCCAGAGGTGTCCACGGCCCGTCCTG
GCCCCAGGGCAGTGATTGACTACAGCAAGGCTGATGCCTGGGCAGTGGGAGCCATCGCCT
ATGAAATCTTCGGGCTTGTCAATCCCTTCTACGGCCAGGGCAAGGCCCACCTTGAAAGCC
GCAGCTACCAAGAGGCTCAGCTACCTGCACTGCCCGAGTCAGTGCCTCCAGACGTGAGAC
AGTTGGTGAGGGCACTGCTCCAGCGAGAGGCCAGCAAGAGACCATCTGCCCGAGTAGCCG
CAAATGTGCTTCATCTAAGCCTCTGGGGTGAACATATTCTAGCCCTGAAGAATCTGAAGT
TAGACAAGATGGTTGGCTGGCTCCTCCAACAATCGGCCGCCACTTTGTTGGCCAACAGGC
TCACAGAGAAGTGTTGTGTGGAAACAAAAATGAAGATGCTCTTTCTGGCTAACCTGGAGT
GTGAAACGCTCTGCCAGGCAGCCCTCCTCCTCTGCTCATGGAGGGCAGCCCTGTGATGTC
CCTGCATGGAGCTGGTGAATTACTAAAAGAACTTGGCATCCTCTGTGTCGTGATGGTCTG
TGAATGGTGAGGGTGGGAGTCAGGAGACAAGACAGCGCAGAGAGGGCTGGTTAGCCGGAA
AAGGCCTCGGGCTTGGCAAATGGAAGAACTTGAGTGAGAGTTCAGTCTGCAGTCCTCTGC
TCACAGACATCTGAAAAGTGAATGGCCAAGCTGGTCTAGTAGATGAGGCTGGACTGAGGA
GGGGTAGGCCTGCATCCACAGAGAGGATCCAGGCCAAGGCACTGGCTGTCAGTGGCAGAG
TTTGGCTGTGACCTTTGCCCCTAACACGAGGAACTCGTTTGAAGGGGCAGCGTAGCATG
TCTGATTTGCCACCTGGATGAAGGCAGACATCAACATGGGTCAGCACGTTCAGTTACGGG
AGTGGGAAATTACATGAGGCCTGGGCCTCTGCGTTCCCAAGCTGTGCGTTCTGGACCAGC
TACTGAATTATTAATCTCACTTAGCGAAAGTGACGGATGAGCAGTAAGTAAGTAAGTGTG
GGGATTTAAACTTGAGGGTTTCCCTCCTGACTAGCCTCTCTTACAGGAATTGTGAAATAT
TAAATGCAAATTTACAACTGCAAAAAAAAAAAAAAAAAAAAAAAAGGGCGGCCC
```

Fig. 3

```
                                                    Met Ala
Val Arg Gln Ala Leu Gly Arg Gly Leu Gln Leu Gly Arg Ala Leu Leu
         5                   10              15

Leu Arg Phe Thr Gly Lys Pro Gly Arg Ala Tyr Gly Leu Gly Arg Pro
     20              25                  30

Gly Pro Ala Ala Gly Cys Val Arg Gly Glu Arg Pro Gly Trp Ala Ala
 35              40                  45                      50

Gly Pro Gly Ala Glu Pro Arg Arg Val Gly Leu Gly Leu Pro Asn Arg
             55                  60                      65

Leu Arg Phe Phe Arg Gln Ser Val Ala Gly Leu Ala Ala Arg Leu Gln
             70              75                  80

Arg Gln Phe Val Val Arg Ala Trp Gly Cys Ala Gly Pro Cys Gly Arg
         85              90              95

Ala Val Phe Leu Ala Phe Gly Leu Gly Leu Gly Leu Ile Glu Glu Lys
     100             105             110

Gln Ala Glu Ser Arg Arg Ala Val Ser Ala Cys Gln Glu Ile Gln Ala
115             120             125             130

Ile Phe Thr Gln Lys Ser Lys Pro Gly Pro Asp Pro Leu Asp Thr Arg
            135             140             145

Arg Leu Gln Gly Phe Arg Leu Glu Glu Tyr Leu Ile Gly Gln Ser Ile
            150             155             160

Gly Lys Gly Cys Ser Ala Ala Val Tyr Glu Ala Thr Met Pro Thr Leu
        165             170             175

Pro Gln Asn Leu Glu Val Thr Lys Ser Thr Gly Leu Leu Pro Gly Arg
    180             185             190

Gly Pro Gly Thr Ser Ala Pro Gly Glu Gly Gln Glu Arg Ala Pro Gly
195             200             205                     210

Ala Pro Ala Phe Pro Leu Ala Ile Lys Met Met Trp Asn Ile Ser Ala
            215             220             225
```

Fig. 3 (continued)

Gly Ser Ser Ser Glu Ala Ile Leu Asn Thr Met Ser Gln Glu Leu Val
        230                     235                 240

Pro Ala Ser Arg Val Ala Leu Ala Gly Glu Tyr Gly Ala Val Thr Tyr
        245                     250                 255

Arg Lys Ser Lys Arg Gly Pro Lys Gln Leu Ala Pro His Pro Asn Ile
    260                 265                 270

Ile Arg Val Leu Arg Ala Phe Thr Ser Ser Val Pro Leu Leu Pro Gly
275                     280                 285                 290

Ala Leu Val Asp Tyr Pro Asp Val Leu Pro Ser Arg Leu His Pro Glu
                295                 300                 305

Gly Leu Gly His Gly Arg Thr Leu Phe Leu Val Met Lys Asn Tyr Pro
            310                 315                 320

Cys Thr Leu Arg Gln Tyr Leu Cys Val Asn Thr Pro Ser Pro Arg Leu
        325                 330                 335

Ala Ala Met Met Leu Leu Gln Leu Leu Glu Gly Val Asp His Leu Val
        340                 345                 350

Gln Gln Gly Ile Ala His Arg Asp Leu Lys Ser Asp Asn Ile Leu Val
355                 360                 365                 370

Glu Leu Asp Pro Asp Gly Cys Pro Trp Leu Val Ile Ala Asp Phe Gly
            375                 380                 385

Cys Cys Leu Ala Asp Glu Ser Ile Gly Leu Gln Leu Pro Phe Ser Ser
        390                 395                 400

Trp Tyr Val Asp Arg Gly Gly Asn Gly Cys Leu Met Ala Pro Glu Val
        405                 410                 415

Ser Thr Ala Arg Pro Gly Pro Arg Ala Val Ile Asp Tyr Ser Lys Ala
    420                 425                 430

Fig. 3 (continued)

Asp Ala Trp Ala Val Gly Ala Ile Ala Tyr Glu Ile Phe Gly Leu Val
435                 440                 445                 450

Asn Pro Phe Tyr Gly Gln Gly Lys Ala His Leu Glu Ser Arg Ser Tyr
                455                 460                 465

Gln Glu Ala Gln Leu Pro Ala Leu Pro Glu Ser Val Pro Pro Asp Val
            470                 475                 480

Arg Gln Leu Val Arg Ala Leu Leu Gln Arg Glu Ala Ser Lys Arg Pro
        485                 490                 495

Ser Ala Arg Val Ala Ala Asn Val Leu His Leu Ser Leu Trp Gly Glu
    500                 505                 510

His Ile Leu Ala Leu Lys Asn Leu Lys Leu Asp Lys Met Val Gly Trp
515                 520                 525                 530

Leu Leu Gln Gln Ser Ala Ala Thr Leu Leu Ala Asn Arg Leu Thr Glu
                535                 540                 545

Lys Cys Cys Val Glu Thr Lys Met Lys Met Leu Phe Leu Ala Asn Leu
            550                 555                 560

Glu Cys Glu Thr Leu Cys Gln Ala Ala Leu Leu Leu Cys Ser Trp Arg
        565                 570                 575

Ala Ala Leu

Fig. 3 (continued)

```
GTCGACCCACGCGGTCCGCCCACGCGTTCCGGAGACATGTCTCTGTGTTTC
TCTCCCCTCCGCTTTTGAGTCCGTTGAAGACACAATTTCTCTCTGTCGGGT
GCTTAGGAGGAGCTCCATGAACATGTATTGAATTGGACTTAGCTGAACAG
GCTGCTGGTTGGCTGCCCAGAGGGGGCAGGCTGTGTTGCTGGGAGCCTTC
CAGCTCCCTGCAGCAGTCATGGGGCAGGGTTCCCCGAGTCCGTAATCCCC
ATTTCCACCTACTTTCCCTTAGTTATTTGATTCCCTGTCTGTCGTACTCAGC
TTAAGTGGAGCATCCCCTTTCCTGGGAGACACGAAGCAGGAAACACTGGC
AAATATCACAGCAGTGAGTTACGACTTTGATGAGGAATTCTTCAGCCAGA
CGAGCGAGCTGGCCAAGGACTTTATTCGGAAGCTTCTGGTTAAAGAGACC
CGGAAACGGCTCACAATCCAAGAGGCTCTCAGACACCCTGGATCACGCC
GGTGGACAACCAGCAAGCCATGGTGCGCAGGGAGTCTGTGGTCAATCTGG
AGAACTTCAGGAAGCAGTATGTCCGCAGGCGGTGGAAGCTTTCCTTCAGC
ATCGTGTCCCTGTGCAACCACCTCACCCGCTCGCTGATGAAGAAGGTGCA
CCTGAGGCCGGATGAGGACCTGAGGAACTGTGAGAGTGACACTGAGGAG
GACATCGCCAGGAGGAAAGCCCTCCACCCACGGAGGAGGAGCAGCACCT
CCTAACTGGCCTGACCTGCAGTGGCCGCCAGGGAGGTCTGGGCCCAGCGG
GGCTCCCTTCTGTGCAGACTTTTGGACCCAGCTCAGCACCAGCACCCGGGC
GTCCTGAGCACTTTGCAAGAGAGATGGGCCCAAGGAATTCAGAAGAGCTT
GCAGGCAAGCCAGGAGACCCTGGGAGCTGTGGCTGTCTTCTGTGGAGGAG
GCTCCAGCATTCCCAAAGCTCTTAATTCTCCATAAAATGGGCTTTCCTCTG
TCTGCCATCCTCAGAGTCTGGGGTGGGAGTGTGGACTTAGGAAAACAATA
TAAAGGACATCCTCATCATCACGGGGTGAAGGTCAGACTAAGGCAGCCTT
CTTCACAGGCTGAGGGGGTTCAGAACCAGCCTGGCCAAAAATTACACCAG
AGAGACAGAGTCCTCCCCATTGGGAACAGGGTGATTGAGGAAAGTGAACC
TTGGGTGTGAGGGACCAATCCTGTGACCTCCCAGAACCATGGAAGCCAGG
ACGTCAGGCTGACCAACACCTCAGACCTTCTGAAGCAGCCCATTGCTGGC
CCGCCATGTTGTAATTTTGCTCATTTTTATTAAACTTCTGGTTTACCTGATG
CTTGGCTTCTTTTAGGGCTACCCCCATCTCATTTCCTTTAGCCCGTGTGCCT
GTAACTCTGAGGGGGGGCACCCAGTGGGGTGCTGAGTGGGCAGAATCTCA
GAAGGTCCTCCTGAACCGTCCGCGCAGGCCTGCAGTGGGCCTGCCTCCTC
CTTGCTTCCCTAACAGGAAGGTGTCCAGTTCAAGAGAACCCACCCAGAGA
CTGGGAGTGGTGGCTCACGCCTATAATCCCTGCGCTTTGGCAGTCCGAGG
CAGGGGAATTGCTTGAACTCAGGAGTTGGAGACCAGCCTGGGCAACATGG
CAAAACGCAGTCTGTACAAAAAATACAAAAAATTAGCCAGGTGTAGGGGT
AGGCACCTGGCATCCCAGCTACTCCAGGGGCTGAGGTGACAGCATTGCTT
AAGCCCAGAAGGTCGAGGCTGCAGTGAGCTGAGATCACGCCACTGCACTC
CAGTCTGGGTGACAGAGAGAGACCATATCCAAAAAAAAAAAAAAAGGG
CGGCCGC
```

LFDSLSVVLSLSGASPFLGDTKQETLANITAVSYDFDEEFFSQTSELAKDFIRKL
LVKETRKRLTIQEALRHPWITPVDNQQAMVRRESVVNLENFRKQYVRRRWK
LSFSIVSLCNHLTRSLMKKVHLRPDEDLRNCESDTEEDIARRKALHPRRRSSTS

Fig. 4

```
  T   A   L   A   K   E   L   R   E   L   R   I   E   E   T   N   R   P   M      19
G ACG GCA TTA GCC AAA GAA CTA AGA GAA CTC CGG ATT GAA GAA ACA AAC CGC CCA ATG     57

K   K   V   T   D   Y   S   S   S   E   E   S   E   S   S   E   E   E   E      39
AAG AAG GTG ACT GAT TAC TCC TCC TCC AGT GAG GAG TCA GAA AGT AGC GAG GAA GAG GAG  117

E   D   G   E   S   E   T   H   D   G   T   V   A   V   S   D   I   P   R   L  59
GAA GAT GGA GAG AGC GAG ACC CAT GAT GGG ACA GTG GCT GTC AGC GAC ATA CCC AGA CTG 177

I   P   T   G   A   P   G   S   N   E   Q   Y   N   V   G   M   V   G   T   H  79
ATA CCA ACA GGA GCT CCA GGC AGC AAC GAG CAG TAC AAT GTG GGA ATG GTG GGG ACG CAT 237

G   L   E   T   S   H   A   D   S   F   S   G   S   I   S   R   E   G   T   L  99
GGG CTG GAG ACC TCT CAT GCG GAC AGT TTC AGC GGC AGT ATT TCA AGA GAA GGA ACC TTG 297

M   I   R   E   T   S   G   E   K   K   R   S   G   H   S   D   S   N   G   F 119
ATG ATT AGA GAG ACG TCT GGA GAG AAG AAG CGA TCT GGC CAC AGT GAC AGC AAT GGC TTT 357

A   G   H   I   N   L   P   D   L   V   Q   Q   S   H   S   P   A   G   T   P 139
GCT GGC CAC ATC AAC CTC CCT GAC CTG GTG CAG CAG AGC CAT TCT CCA GCT GGA ACC CCG 417

T   E   G   L   G   R   V   S   T   H   S   Q   E   M   D   S   G   T   E   Y 159
ACT GAG GGA CTG GGG CGC GTC TCA ACC CAT TCC CAG GAG ATG GAC TCT GGG ACT GAA TAT 477

G   M   G   S   S   T   K   A   S   F   T   P   F   V   D   P   R   V   Y   Q 179
GGC ATG GGG AGC AGC ACC AAA GCC TCC TTC ACC CCC TTT GTG GAC CCC AGA GTA TAC CAG 537

T   S   P   T   D   E   D   E   E   D   E   E   S   S   A   A   A   L   F   T 199
ACG TCT CCC ACT GAT GAA GAT GAA GAG GAT GAG GAA TCA TCA GCC GCA GCT CTG TTT ACT 597

S   E   L   L   R   Q   E   Q   A   K   L   N   E   A   R   K   I   S   V   V 219
AGC GAA CTT CTT AGG CAA GAA CAG GCC AAA CTC AAT GAA GCA AGA AAG ATT TCG GTG GTA 657

N   V   N   P   T   N   I   R   P   H   S   D   T   P   E   I   R   K   Y   K 239
AAT GTA AAC CCA ACC AAC ATT CGG CCT CAT AGC GAC ACA CCA GAA ATC AGA AAA TAC AAG 717

K   R   F   N   S   E   I   L   C   A   A   L   W   G   V   N   L   L   V   G 259
AAA CGA TTC AAC TCA GAA ATA CTT TGT GCA GCT CTG TGG GGT GTA AAC CTT CTG GTG GGG 777

T   E   N   G   L   M   L   L   D   R   S   G   Q   G   K   V   Y   N   L   I 279
ACT GAA AAT GGC CTG ATG CTT TTG GAC CGA AGT GGG CAA GGC AAA GTC TAT AAT CTG ATC 837

N   R   R   R   F   Q   Q   M   D   V   L   E   G   L   N   V   L   V   T   I 299
AAC CGG AGG GGA TTT CAG CAG ATG GAT GTG CTA GAG GGA CTG AAT GTC CTT GTG ACA ATT 897

S   G   K   K   N   K   L   R   V   Y   Y   L   S   W   L   R   N   R   I   L 319
TCA GGA AAG AAG AAT AAG CTA CGA GTT TAC TAT CTT TCA TGG TTA AGA AAC AGA ATA CTA 957

H   N   D   P   E   V   E   K   K   Q   G   W   I   T   V   G   D   L   E   G 339
CAT AAT GAC CCA GAA GTA GAA AAG AAA CAA GGC TGG ATC ACT GTT GGG GAC TTG GAA GGC 1017
```

Fig. 5

```
C   I   H   Y   K   V   V   K   Y   E   R   I   K   F   L   V   I   A   L   K    359
TGT ATA CAT TAT AAA GTT GTT AAA TAT GAA AGG ATC AAA TTT TTG GTG ATT GCC TTA AAG  1077

N   A   V   E   I   Y   A   W   A   P   K   P   Y   H   K   F   M   A   F   K    379
AAT GCT GTG GAA ATA TAT GCT TGG GCT CCT AAA CCG TAT CAT AAA TTC ATG GCA TTT AAG  1137

S   F   A   D   L   Q   H   K   P   L   L   V   D   L   T   V   E   E   G   Q    399
TCT TTT GCA GAT CTC CAG CAC AAG CCT CTG CTA GTT GAT CTC ACG GTA GAA GAA GGT CAA  1197

R   L   K   V   I   F   G   S   H   T   G   F   H   V   I   D   V   D   S   G    419
AGA TTA AAG GTT ATT TTT GGT TCA CAC ACT GGT TTC CAT GTA ATT GAT GTT GAT TCA GGA  1257

N   S   Y   D   I   Y   I   P   S   H   I   Q   G   N   I   T   P   H   A   I    439
AAC TCT TAT GAT ATC TAC ATA CCA TCT CAT ATT CAG GGC AAT ATC ACT CCT CAT GCT ATT  1317

V   I   L   P   K                                                                 444
GTC ATC TTG CCT AAA                                                              1332
```

Fig. 5 (continued)

SEQUENCE LISTING

```
<160> NUMBER OF SEQ ID NOS: 15

<210> SEQ ID NO 1
<211> LENGTH: 4137
<212> TYPE: DNA
<213> ORGANISM: Homo sapiens
<220> FEATURE:
<223> OTHER INFORMATION: 'n' at positions 2872, 3597 and 3682 may be any
      nucleic acid
<220> FEATURE:
<221> NAME/KEY: CDS
<222> LOCATION: (297)..(1202)
```

-continued

```
<400> SEQUENCE: 1
tcgacccacg cgtccgggag gatcgggagt cgcgggagga tgggccgccg ctaggctcgc        60
actccggacg cgcctcgcag tgcgcagggt gggtgcccg  cgcctgcagc gtccgccggg       120
gcggcgcggc gggaggtggc cgacaggctc cgggcctcgc agcctcagcc cccggcccag       180
cgcgctttcc gacggcggcg ccgcgccgag ccacccgccc gcccaaggtc tctcgcgggc       240
gggagaacgg aaaactccca acttcctgag ttctaaagtt cctgttgctt cagaca atg       299
                                                                   Met
                                                                    1 gat gag caa tca caa gga atg caa ggg cca cct gtt cct cag ttc caa        347
Asp Glu Gln Ser Gln Gly Met Gln Gly Pro Pro Val Pro Gln Phe Gln
              5                  10                  15 cca cag aag gcc tta cga ccg gat atg ggc tat aat aca tta gcc aac        395
Pro Gln Lys Ala Leu Arg Pro Asp Met Gly Tyr Asn Thr Leu Ala Asn
         20                  25                  30 ttt cga ata gaa aag aaa att ggt cgc gga caa ttt agt gaa gtt tat        443
Phe Arg Ile Glu Lys Lys Ile Gly Arg Gly Gln Phe Ser Glu Val Tyr
     35                  40                  45 aga gca gcc tgt ctc ttg gat gga gta cca gta gct tta aaa aaa gtg        491
Arg Ala Ala Cys Leu Leu Asp Gly Val Pro Val Ala Leu Lys Lys Val
 50                  55                  60                  65 cag ata ttt gat tta atg gat gcc aaa gca cgt gct gat tgc atc aaa        539
Gln Ile Phe Asp Leu Met Asp Ala Lys Ala Arg Ala Asp Cys Ile Lys
                 70                  75                  80 gaa ata gat ctt ctt aag caa ctc aac cat cca aat gta ata aaa tat        587
Glu Ile Asp Leu Leu Lys Gln Leu Asn His Pro Asn Val Ile Lys Tyr
             85                  90                  95 tat gca tca ttc att gaa gat aat gaa cta aac ata gtt ttg gaa cta        635
Tyr Ala Ser Phe Ile Glu Asp Asn Glu Leu Asn Ile Val Leu Glu Leu
        100                 105                 110 gca gat gct ggc gac cta tcc aga atg atc aag cat ttt aag aag caa        683
Ala Asp Ala Gly Asp Leu Ser Arg Met Ile Lys His Phe Lys Lys Gln
    115                 120                 125 aag agg cta att cct gaa aga act gtt tgg aag tat ttt gtt cag ctt        731
Lys Arg Leu Ile Pro Glu Arg Thr Val Trp Lys Tyr Phe Val Gln Leu
130                 135                 140                 145 tgc agt gca ttg gaa cac atg cat tct cga aga gtc atg cat aga gat        779
Cys Ser Ala Leu Glu His Met His Ser Arg Arg Val Met His Arg Asp
                150                 155                 160 ata aaa cca gct aat gtg ttc att aca gcc act ggg gtg gta aaa ctt        827
Ile Lys Pro Ala Asn Val Phe Ile Thr Ala Thr Gly Val Val Lys Leu
            165                 170                 175 gga gat ctt ggg ctt ggc cgg ttt ttc agc tca aaa acc aca gct gca        875
Gly Asp Leu Gly Leu Gly Arg Phe Phe Ser Ser Lys Thr Thr Ala Ala
        180                 185                 190 cat tct tta gtt ggt acg cct tat tac atg tct cca gag aga ata cat        923
His Ser Leu Val Gly Thr Pro Tyr Tyr Met Ser Pro Glu Arg Ile His
    195                 200                 205 gaa aat gga tac aac ttc aaa tct gac atc tgg tct ctt ggc tgt cta        971
Glu Asn Gly Tyr Asn Phe Lys Ser Asp Ile Trp Ser Leu Gly Cys Leu
210                 215                 220                 225 cta tat gag atg gct gca tta caa agt cct ttc tat ggt gac aaa atg       1019
Leu Tyr Glu Met Ala Ala Leu Gln Ser Pro Phe Tyr Gly Asp Lys Met
                230                 235                 240 aat tta tac tca ctg tgt aag aag ata gaa cag tgt gac tac cca cct       1067
Asn Leu Tyr Ser Leu Cys Lys Lys Ile Glu Gln Cys Asp Tyr Pro Pro
            245                 250                 255 ctt cct tca gat cac tat tca gaa gaa ctc cga cag tta gtt aat atg       1115
```

```
Leu Pro Ser Asp His Tyr Ser Glu Glu Leu Arg Gln Leu Val Asn Met
        260                 265                 270 tgc atc aac cca gat cca gag aag cga cca gac gtc acc tat gtt tat    1163
Cys Ile Asn Pro Asp Pro Glu Lys Arg Pro Asp Val Thr Tyr Val Tyr
    275                 280                 285 gac gta gca aag agg atg cat gca tgc act gca agc agc taaacatgca     1212
Asp Val Ala Lys Arg Met His Ala Cys Thr Ala Ser Ser
290                 295                 300 agatcatgaa gagtgtaacc aaagtaattg aaagtatttt gtgcaaagtc gtacctsccc  1272
atttatgtct gggtgttaag attaatattt cagagctagt gtgctctgaa tccttaacca  1332
gttttcatat aagcttcatt ttgtaccagt cacctaaatc acctccttgc aaccccaaa   1392 tgactttgga ataactgaat tgcatgttag gagagaaaat gaaacatgat ggttttgaat  1452
ggctaaaggt ttatagaatt tcttacagtt ttctgctgat aaattgtgtt tagatagact  1512
gtcagtgcca aatattgaag gtgcagcttg cacacatca aatagactc atcctgaga    1572 aaaagtatct gaacatgtga cttgtttctt ttttagtaat ttatggacat tgagatgaac  1632
acaattgtga acttttgtga agatttatt tttaaacgtt tgaagtacta gttttagttc   1692
ttagcagagt agttttcaaa tatgattctt atgataaatg tagacacaaa ctatttgaga  1752
aacatttaga actcttagct tatacattca aaatgtaact attaaatgtg aagatttggg  1812
gacaaaatgt gagtcagaca ctgaagagtt ttttgttttg ttttaatatt tttgatattc  1872
tctttgcatt gaaatggtat aaatgaatcc atttaaaaag tggttaagga tttgtttagc  1932
tggtgtgata ataattttta aagttgcaca ttgcccaagg cttttttttgt gtgtttttat  1992 tgttgtttgt acatttgaaa aatattcttt gaataacctt gcagtactat atttcaagrt  2052
ttctttataa atttaagtgc attttaactc ataattgtac actataatat aagcctaagt  2112
ttttattcat aagttttatt gaagttctga tcggtcccct tcagaaattt ttttatatta  2172
ttcttcaagt tactttctta tttatattgt atgtgcattt tatccattaa tgtttcatac  2232
tttctgagag tataataccc ttttaaaaga tatttggtat accaatactt ttcctggatt  2292
gaaaactttt tttaaacttt ttaaaatttg ggccactctg tatgcatatg tttggtcttg  2352
ttaaagagga agaaaggatg tgtgttatac tgtacctgtg aatgttgata cagttacaat  2412
ttatttgaca aggttgtaat tctagaatat gcttaataaa atgaaaactg gccatgacta  2472
cagccagaac tgttatgaga ttaacatttc tattgagaag cttttgagta aagtactgta  2532
tttgttcatg aagatgactg agatggtaac acttcgtgta gcttaaggaa atgggcagaa  2592
tttcgtaaat gctgttgtgc agatgtgttt tccctgaatg cttcgtatt agtggcgacc    2652 agtttctcac agaattgtga agcctgaagg ccaagaggaa gtcactgtta aaggactctg  2712
tgccatctta caaccttgga tgaattatcc tgccaacgtg aaaacctcat gttcaaagaa  2772
cacttccctt tagccgatgt aactgctggt tttgtttttc atatgtgttt ttcttacact  2832
catttgaatg ctttcaagca tttgtaaact taaaaaaaan wawaaagggc aaaaagtctg  2892
aacccttgtt ttctgaaatc taatcagtta tgtatggttt ctgaagggta attttatttt  2952
ggaataggta aagcgaaacc tgttttgtcw tgttttttcct gagggctaga tgcattttt   3012 ttctcacact cttaatgact tttaacattt atactgagca tccatagata tattcctaga  3072
agtatgagaa gaattattct tattgaccat taatgtcatg ttcattttaa tgtaatataa  3132
ttgagatgaa atgttctctg gttggaacag atactctctt ttttttttctt gcaatcttta  3192 agaatacata gatctaaaat tcattagctt gacccctcaa agtaacttttt aagtaaagat  3252
```

```
taaagctttt cttctcagtg aatatatctg ctagaaggaa atagctggga agaatttaat    3312
gatcagggaa attcattatt tctatatgtg gaaactttt gcttcgaata ttgtatcttt    3372
ttaaatctaa atgttcatat ttttcctgaa gaaaccactg tgtaaaaatc aaatttaat    3432 tttgaatgga ataatttcaa agaactatga agatgatttg aagctctaat ttatatagtc    3492
acctataaaa tgttctttat atgtgttcat aagtaaattt tatattgatt aagttaaact    3552
tttgaattga tttgaggagc agtaaaatga aagctatatc tattnctaaa ccytatttag    3612
acattggkac cagttaccca ggtgaaaata kggagtaact ttgttttgta tggtaaggtt    3672
taggaatggn ggatgaaggg tatctctata taaataaagt gctcaacaat gtgcaatgat    3732
tgtaaattta gtaagatatt acagccattt catgaatgct ttaccattca acatagtatc    3792
tattacaaaa cacctttctt gtatccatat acttcaggtg ttgctgttaa catttactat    3852
gatatttatt ttaaccaaaa tgttactcac attaaatgtt tattctttaa aatgaatgta    3912
ttatgttttt aacccacaaa tgcatactta ccctgtgcct catatttcaa tagtactgta    3972
atatggacat cttttgtgaa atactttat tttgttatgc tttaaatata catacaaaaa    4032
gatttctgtt attagctttg aaaattgtat aatatcctaa tataacaaaa atataaaaat    4092
aaaaatgaat acagtaaaaa aaaaaaaaaa aaaaaaaaaa aaagg    4137
```

<210> SEQ ID NO 2
<211> LENGTH: 302
<212> TYPE: PRT
<213> ORGANISM: Homo sapiens

<400> SEQUENCE: 2

```
Met Asp Glu Gln Ser Gln Gly Met Gln Gly Pro Pro Val Pro Gln Phe
  1               5                  10                  15

Gln Pro Gln Lys Ala Leu Arg Pro Asp Met Gly Tyr Asn Thr Leu Ala
             20                  25                  30

Asn Phe Arg Ile Glu Lys Lys Ile Gly Arg Gly Gln Phe Ser Glu Val
         35                  40                  45

Tyr Arg Ala Ala Cys Leu Leu Asp Gly Val Pro Val Ala Leu Lys Lys
     50                  55                  60

Val Gln Ile Phe Asp Leu Met Asp Ala Lys Ala Arg Ala Asp Cys Ile
 65                  70                  75                  80

Lys Glu Ile Asp Leu Leu Lys Gln Leu Asn His Pro Asn Val Ile Lys
                 85                  90                  95

Tyr Tyr Ala Ser Phe Ile Glu Asp Asn Glu Leu Asn Ile Val Leu Glu
            100                 105                 110

Leu Ala Asp Ala Gly Asp Leu Ser Arg Met Ile Lys His Phe Lys Lys
        115                 120                 125

Gln Lys Arg Leu Ile Pro Glu Arg Thr Val Trp Lys Tyr Phe Val Gln
    130                 135                 140

Leu Cys Ser Ala Leu Glu His Met His Ser Arg Arg Val Met His Arg
145                 150                 155                 160

Asp Ile Lys Pro Ala Asn Val Phe Ile Thr Ala Thr Gly Val Val Lys
                165                 170                 175

Leu Gly Asp Leu Gly Leu Gly Arg Phe Phe Ser Ser Lys Thr Thr Ala
            180                 185                 190

Ala His Ser Leu Val Gly Thr Pro Tyr Tyr Met Ser Pro Glu Arg Ile
        195                 200                 205

His Glu Asn Gly Tyr Asn Phe Lys Ser Asp Ile Trp Ser Leu Gly Cys
    210                 215                 220
```

```
Leu Leu Tyr Glu Met Ala Ala Leu Gln Ser Pro Phe Tyr Gly Asp Lys
225                 230                 235                 240

Met Asn Leu Tyr Ser Leu Cys Lys Lys Ile Glu Gln Cys Asp Tyr Pro
                245                 250                 255

Pro Leu Pro Ser Asp His Tyr Ser Glu Glu Leu Arg Gln Leu Val Asn
            260                 265                 270

Met Cys Ile Asn Pro Asp Pro Glu Lys Arg Pro Asp Val Thr Tyr Val
        275                 280                 285

Tyr Asp Val Ala Lys Arg Met His Ala Cys Thr Ala Ser Ser
    290                 295                 300

<210> SEQ ID NO 3
<211> LENGTH: 906
<212> TYPE: DNA
<213> ORGANISM: Homo sapiens
<220> FEATURE:
<221> NAME/KEY: CDS
<222> LOCATION: (1)..(906)

<400> SEQUENCE: 3 atg gat gag caa tca caa gga atg caa ggg cca cct gtt cct cag ttc      48
Met Asp Glu Gln Ser Gln Gly Met Gln Gly Pro Pro Val Pro Gln Phe
1               5                   10                  15 caa cca cag aag gcc tta cga ccg gat atg ggc tat aat aca tta gcc      96
Gln Pro Gln Lys Ala Leu Arg Pro Asp Met Gly Tyr Asn Thr Leu Ala
            20                  25                  30 aac ttt cga ata gaa aag aaa att ggt cgc gga caa ttt agt gaa gtt     144
Asn Phe Arg Ile Glu Lys Lys Ile Gly Arg Gly Gln Phe Ser Glu Val
        35                  40                  45 tat aga gca gcc tgt ctc ttg gat gga gta cca gta gct tta aaa aaa     192
Tyr Arg Ala Ala Cys Leu Leu Asp Gly Val Pro Val Ala Leu Lys Lys
    50                  55                  60 gtg cag ata ttt gat tta atg gat gcc aaa gca cgt gct gat tgc atc     240
Val Gln Ile Phe Asp Leu Met Asp Ala Lys Ala Arg Ala Asp Cys Ile
65                  70                  75                  80 aaa gaa ata gat ctt ctt aag caa ctc aac cat cca aat gta ata aaa     288
Lys Glu Ile Asp Leu Leu Lys Gln Leu Asn His Pro Asn Val Ile Lys
                85                  90                  95 tat tat gca tca ttc att gaa gat aat gaa cta aac ata gtt ttg gaa     336
Tyr Tyr Ala Ser Phe Ile Glu Asp Asn Glu Leu Asn Ile Val Leu Glu
            100                 105                 110 cta gca gat gct ggc gac cta tcc aga atg atc aag cat ttt aag aag     384
Leu Ala Asp Ala Gly Asp Leu Ser Arg Met Ile Lys His Phe Lys Lys
        115                 120                 125 caa aag agg cta att cct gaa aga act gtt tgg aag tat ttt gtt cag     432
Gln Lys Arg Leu Ile Pro Glu Arg Thr Val Trp Lys Tyr Phe Val Gln
    130                 135                 140 ctt tgc agt gca ttg gaa cac atg cat tct cga aga gtc atg cat aga     480
Leu Cys Ser Ala Leu Glu His Met His Ser Arg Arg Val Met His Arg
145                 150                 155                 160 gat ata aaa cca gct aat gtg ttc att aca gcc act ggg gtg gta aaa     528
Asp Ile Lys Pro Ala Asn Val Phe Ile Thr Ala Thr Gly Val Val Lys
                165                 170                 175 ctt gga gat ctt ggg ctt ggc cgg ttt ttc agc tca aaa acc aca gct     576
Leu Gly Asp Leu Gly Leu Gly Arg Phe Phe Ser Ser Lys Thr Thr Ala
            180                 185                 190 gca cat tct tta gtt ggt acg cct tat tac atg tct cca gag aga ata     624
Ala His Ser Leu Val Gly Thr Pro Tyr Tyr Met Ser Pro Glu Arg Ile
        195                 200                 205
```

```
cat gaa aat gga tac aac ttc aaa tct gac atc tgg tct ctt ggc tgt      672
His Glu Asn Gly Tyr Asn Phe Lys Ser Asp Ile Trp Ser Leu Gly Cys
    210                 215                 220 cta cta tat gag atg gct gca tta caa agt cct ttc tat ggt gac aaa      720
Leu Leu Tyr Glu Met Ala Ala Leu Gln Ser Pro Phe Tyr Gly Asp Lys
225                 230                 235                 240 atg aat tta tac tca ctg tgt aag aag ata gaa cag tgt gac tac cca      768
Met Asn Leu Tyr Ser Leu Cys Lys Lys Ile Glu Gln Cys Asp Tyr Pro
                245                 250                 255 cct ctt cct tca gat cac tat tca gaa gaa ctc cga cag tta gtt aat      816
Pro Leu Pro Ser Asp His Tyr Ser Glu Glu Leu Arg Gln Leu Val Asn
            260                 265                 270 atg tgc atc aac cca gat cca gag aag cga cca gac gtc acc tat gtt      864
Met Cys Ile Asn Pro Asp Pro Glu Lys Arg Pro Asp Val Thr Tyr Val
        275                 280                 285 tat gac gta gca aag agg atg cat gca tgc act gca agc agc              906
Tyr Asp Val Ala Lys Arg Met His Ala Cys Thr Ala Ser Ser
290                 295                 300

<210> SEQ ID NO 4
<211> LENGTH: 2120
<212> TYPE: DNA
<213> ORGANISM: Homo sapiens
<220> FEATURE:
<221> NAME/KEY: CDS
<222> LOCATION: (47)..(1411)

<400> SEQUENCE: 4
gtcgacccac gcgtccggtg gaagtataat actttgtcat tatgag atg tcg tct        55
                                              Met Ser Ser
                                                1 ctc ggt gcc tcc ttt gtg caa att aaa ttt gat gac ttg cag ttt ttt      103
Leu Gly Ala Ser Phe Val Gln Ile Lys Phe Asp Asp Leu Gln Phe Phe
    5                  10                  15 gaa aac tgc ggt gga gga agt ttt ggg agt gtt tat cga gcc aaa tgg      151
Glu Asn Cys Gly Gly Gly Ser Phe Gly Ser Val Tyr Arg Ala Lys Trp
 20                 25                  30                  35 ata tca cag gac aag gag gtg gct gta aag aag ctc ctc aaa ata gag      199
Ile Ser Gln Asp Lys Glu Val Ala Val Lys Lys Leu Leu Lys Ile Glu
                40                  45                  50 aaa gag gca gaa ata ctc agt gtc ctc agt cac aga aac atc atc cag      247
Lys Glu Ala Glu Ile Leu Ser Val Leu Ser His Arg Asn Ile Ile Gln
            55                  60                  65 ttt tat gga gta att ctt gaa cct ccc aac tat ggc att gtc aca gaa      295
Phe Tyr Gly Val Ile Leu Glu Pro Pro Asn Tyr Gly Ile Val Thr Glu
        70                  75                  80 tat gct tct ctg gga tca ctc tat gat tac att aac agt aac aga agt      343
Tyr Ala Ser Leu Gly Ser Leu Tyr Asp Tyr Ile Asn Ser Asn Arg Ser
85                  90                  95 gag gag atg gat atg gat cac att atg acc tgg gcc act gat gta gcc      391
Glu Glu Met Asp Met Asp His Ile Met Thr Trp Ala Thr Asp Val Ala
100                 105                 110                 115 aaa gga atg cat tat tta cat atg gag gct cct gtc aag gtg att cac      439
Lys Gly Met His Tyr Leu His Met Glu Ala Pro Val Lys Val Ile His
                120                 125                 130 aga gac ctc aag tca aga aac gtt gtt ata gct gct gat gga gta ctg      487
Arg Asp Leu Lys Ser Arg Asn Val Val Ile Ala Ala Asp Gly Val Leu
            135                 140                 145 aag atc tgt gac ttt ggt gcc tct cgg ttc cat aac cat aca aca cac      535
Lys Ile Cys Asp Phe Gly Ala Ser Arg Phe His Asn His Thr Thr His
        150                 155                 160
```

-continued

| | |
|---|---|
| atg tcc ttg gtt gga act ttc cca tgg atg gct cca gaa gtt atc cag<br>Met Ser Leu Val Gly Thr Phe Pro Trp Met Ala Pro Glu Val Ile Gln<br>165                    170                  175 | 583 |
| agt ctc cct gtg tca gaa act tgt gac aca tat tcc tat ggt gtg gtt<br>Ser Leu Pro Val Ser Glu Thr Cys Asp Thr Tyr Ser Tyr Gly Val Val<br>180                    185                  190                195 | 631 |
| ctc tgg gag atg cta aca agg gag gtc ccc ttt aaa ggt ttg gaa gga<br>Leu Trp Glu Met Leu Thr Arg Glu Val Pro Phe Lys Gly Leu Glu Gly<br>                    200                  205                210 | 679 |
| tta caa gta gct tgg ctt gta gtg gaa aaa aac gag aga tta acc att<br>Leu Gln Val Ala Trp Leu Val Val Glu Lys Asn Glu Arg Leu Thr Ile<br>              215                  220                225 | 727 |
| cca agc agt tgc ccc aga agt ttt gct gaa ctg tta cat cag tgt tgg<br>Pro Ser Ser Cys Pro Arg Ser Phe Ala Glu Leu Leu His Gln Cys Trp<br>        230                  235                240 | 775 |
| gaa gct gat gcc aag aaa cgg cca tca ttc aag caa atc att tca atc<br>Glu Ala Asp Ala Lys Lys Arg Pro Ser Phe Lys Gln Ile Ile Ser Ile<br>245                    250                  255 | 823 |
| ctg gag tcc atg tca aat gac acg agc ctt cct gac aag tgt aac tca<br>Leu Glu Ser Met Ser Asn Asp Thr Ser Leu Pro Asp Lys Cys Asn Ser<br>260                    265                  270                275 | 871 |
| ttc cta cac aac aag gcg gag tgg agg tgc gaa att gag gca act ctt<br>Phe Leu His Asn Lys Ala Glu Trp Arg Cys Glu Ile Glu Ala Thr Leu<br>              280                  285                290 | 919 |
| gag agg cta aag aaa cta gag cgt gat ctc agc ttt aag gag cag gag<br>Glu Arg Leu Lys Lys Leu Glu Arg Asp Leu Ser Phe Lys Glu Gln Glu<br>        295                  300                305 | 967 |
| ctt aaa gaa cga gaa aga cgt tta aag atg tgg gag caa aag ctg aca<br>Leu Lys Glu Arg Glu Arg Arg Leu Lys Met Trp Glu Gln Lys Leu Thr<br>310                    315                  320 | 1015 |
| gag cag tcc aac acc ccg ctt ctc ttg cct ctt gct gca aga atg tct<br>Glu Gln Ser Asn Thr Pro Leu Leu Leu Pro Leu Ala Ala Arg Met Ser<br>325                    330                  335 | 1063 |
| gag gag tct tac ttt gaa tct aaa aca gag gag tca aac agt gca gag<br>Glu Glu Ser Tyr Phe Glu Ser Lys Thr Glu Glu Ser Asn Ser Ala Glu<br>340                    345                  350                355 | 1111 |
| atg tca tgt cag atc aca gca aca agt aac ggg gag ggc cat ggc atg<br>Met Ser Cys Gln Ile Thr Ala Thr Ser Asn Gly Glu Gly His Gly Met<br>              360                  365                370 | 1159 |
| aac cca agt ctg cag gcc atg atg ctg atg ggc ttt ggg gat atc ttc<br>Asn Pro Ser Leu Gln Ala Met Met Leu Met Gly Phe Gly Asp Ile Phe<br>        375                  380                385 | 1207 |
| tca atg aac aaa gca gga gct gtg atg cat tct ggg atg cag ata aac<br>Ser Met Asn Lys Ala Gly Ala Val Met His Ser Gly Met Gln Ile Asn<br>390                    395                  400 | 1255 |
| atg caa gcc aag cag aat tct tcc aaa acc aca tct aag aga agg ggg<br>Met Gln Ala Lys Gln Asn Ser Ser Lys Thr Thr Ser Lys Arg Arg Gly<br>405                    410                  415 | 1303 |
| aag aaa gtc aac atg gct ctg ggg ttc agt gat ttt gac ttg tca gaa<br>Lys Lys Val Asn Met Ala Leu Gly Phe Ser Asp Phe Asp Leu Ser Glu<br>420                    425                  430                435 | 1351 |
| ggt gac gat gat gat gat gat gac ggt gag gag gag gat aat gac atg<br>Gly Asp Asp Asp Asp Asp Asp Asp Gly Glu Glu Glu Asp Asn Asp Met<br>              440                  445                450 | 1399 |
| gat aat agt gaa tgaaagcaga aagcaaagta ataaaatcac aaatgtttgg<br>Asp Asn Ser Glu<br>        455 | 1451 |
| aaaacacaaa agtaacttgt ttatctcagt ctgtacaaaa acagtaagga ggcagaaagc | 1511 |
| caagcactgc atttttaggc caatcacatt tacatgaccg taatttctta tcaattctac | 1571 |

```
ttttattttt gcttacagaa aaacgggggg agaattaagc caaagaagta tatttatgaa    1631
tcagcaaatg tggtgcctga ttatagaaat ttgtgatcct atatacaata taggactttt    1691
aaagttgtga cattctggct ttttctttta atgaatactt tttagtttgt atttgacttt    1751
atttccttta ttcaaatcat ttttaaaaac ttacattttg aacaaacact cttaactcct    1811
aattgttctt tgacacgtag taattctgtg acatacttttt tttttcttat agcaatacac   1871
tgtaatatca gaaatggttg gcctgagcaa cctagtaaga cctcgtctct actaataatt    1931
aaaaaactag ctggcatggt agcacacacc tgtagtccca gatacttggg aggccaaggc    1991
aggaggattg cttgagacct agcaatcagt cagggctgca gtgagccatg atggcaccac    2051
tgcactctag cctgggcaag agaacaagat cctgtctcaa aaacaaaaa aaaaaaaaa     2111 gggcggccg                                                           2120
```

<210> SEQ ID NO 5
<211> LENGTH: 455
<212> TYPE: PRT
<213> ORGANISM: Homo sapiens

<400> SEQUENCE: 5

```
Met Ser Ser Leu Gly Ala Ser Phe Val Gln Ile Lys Phe Asp Asp Leu
 1               5                  10                  15

Gln Phe Phe Glu Asn Cys Gly Gly Gly Ser Phe Gly Ser Val Tyr Arg
            20                  25                  30

Ala Lys Trp Ile Ser Gln Asp Lys Glu Val Ala Val Lys Lys Leu Leu
        35                  40                  45

Lys Ile Glu Lys Glu Ala Glu Ile Leu Ser Val Leu Ser His Arg Asn
    50                  55                  60

Ile Ile Gln Phe Tyr Gly Val Ile Leu Glu Pro Pro Asn Tyr Gly Ile
65                  70                  75                  80

Val Thr Glu Tyr Ala Ser Leu Gly Ser Leu Tyr Asp Tyr Ile Asn Ser
                85                  90                  95

Asn Arg Ser Glu Glu Met Asp Met Asp His Ile Met Thr Trp Ala Thr
            100                 105                 110

Asp Val Ala Lys Gly Met His Tyr Leu His Met Glu Ala Pro Val Lys
        115                 120                 125

Val Ile His Arg Asp Leu Lys Ser Arg Asn Val Ile Ala Ala Asp
    130                 135                 140

Gly Val Leu Lys Ile Cys Asp Phe Gly Ala Ser Arg Phe His Asn His
145                 150                 155                 160

Thr Thr His Met Ser Leu Val Gly Thr Phe Pro Trp Met Ala Pro Glu
                165                 170                 175

Val Ile Gln Ser Leu Pro Val Ser Glu Thr Cys Asp Thr Tyr Ser Tyr
            180                 185                 190

Gly Val Val Leu Trp Glu Met Leu Thr Arg Glu Val Pro Phe Lys Gly
        195                 200                 205

Leu Glu Gly Leu Gln Val Ala Trp Leu Val Val Glu Lys Asn Glu Arg
    210                 215                 220

Leu Thr Ile Pro Ser Ser Cys Pro Arg Ser Phe Ala Glu Leu Leu His
225                 230                 235                 240

Gln Cys Trp Glu Ala Asp Ala Lys Lys Arg Pro Ser Phe Lys Gln Ile
                245                 250                 255

Ile Ser Ile Leu Glu Ser Met Ser Asn Asp Thr Ser Leu Pro Asp Lys
            260                 265                 270
```

```
Cys Asn Ser Phe Leu His Asn Lys Ala Glu Trp Arg Cys Glu Ile Glu
            275                 280                 285

Ala Thr Leu Glu Arg Leu Lys Lys Leu Glu Arg Asp Leu Ser Phe Lys
        290                 295                 300

Glu Gln Glu Leu Lys Glu Arg Arg Leu Lys Met Trp Glu Gln
305                 310                 315                 320

Lys Leu Thr Glu Gln Ser Asn Thr Pro Leu Leu Pro Leu Ala Ala
            325                 330                 335

Arg Met Ser Glu Glu Ser Tyr Phe Glu Ser Lys Thr Glu Glu Ser Asn
            340                 345                 350

Ser Ala Glu Met Ser Cys Gln Ile Thr Ala Thr Ser Asn Gly Glu Gly
            355                 360                 365

His Gly Met Asn Pro Ser Leu Gln Ala Met Met Leu Met Gly Phe Gly
        370                 375                 380

Asp Ile Phe Ser Met Asn Lys Ala Gly Ala Val Met His Ser Gly Met
385                 390                 395                 400

Gln Ile Asn Met Gln Ala Lys Gln Asn Ser Lys Thr Thr Ser Lys
            405                 410                 415

Arg Arg Gly Lys Lys Val Asn Met Ala Leu Gly Phe Ser Asp Phe Asp
            420                 425                 430

Leu Ser Glu Gly Asp Asp Asp Asp Asp Asp Gly Glu Glu Glu Asp
        435                 440                 445

Asn Asp Met Asp Asn Ser Glu
        450                 455

<210> SEQ ID NO 6
<211> LENGTH: 1365
<212> TYPE: DNA
<213> ORGANISM: Homo sapiens
<220> FEATURE:
<221> NAME/KEY: CDS
<222> LOCATION: (1)..(1365)

<400> SEQUENCE: 6 atg tcg tct ctc ggt gcc tcc ttt gtg caa att aaa ttt gat gac ttg      48
Met Ser Ser Leu Gly Ala Ser Phe Val Gln Ile Lys Phe Asp Asp Leu
  1               5                  10                  15 cag ttt ttt gaa aac tgc ggt gga gga agt ttt ggg agt gtt tat cga      96
Gln Phe Phe Glu Asn Cys Gly Gly Gly Ser Phe Gly Ser Val Tyr Arg
             20                  25                  30 gcc aaa tgg ata tca cag gac aag gag gtg gct gta aag aag ctc ctc     144
Ala Lys Trp Ile Ser Gln Asp Lys Glu Val Ala Val Lys Lys Leu Leu
         35                  40                  45 aaa ata gag aaa gag gca gaa ata ctc agt gtc ctc agt cac aga aac     192
Lys Ile Glu Lys Glu Ala Glu Ile Leu Ser Val Leu Ser His Arg Asn
     50                  55                  60 atc atc cag ttt tat gga gta att ctt gaa cct ccc aac tat ggc att     240
Ile Ile Gln Phe Tyr Gly Val Ile Leu Glu Pro Pro Asn Tyr Gly Ile
 65                  70                  75                  80 gtc aca gaa tat gct tct ctg gga tca ctc tat gat tac att aac agt     288
Val Thr Glu Tyr Ala Ser Leu Gly Ser Leu Tyr Asp Tyr Ile Asn Ser
                 85                  90                  95 aac aga agt gag gag atg gat atg gat cac att atg acc tgg gcc act     336
Asn Arg Ser Glu Glu Met Asp Met Asp His Ile Met Thr Trp Ala Thr
            100                 105                 110 gat gta gcc aaa gga atg cat tat tta cat atg gag gct cct gtc aag     384
Asp Val Ala Lys Gly Met His Tyr Leu His Met Glu Ala Pro Val Lys
        115                 120                 125
```

```
gtg att cac aga gac ctc aag tca aga aac gtt gtt ata gct gct gat      432
Val Ile His Arg Asp Leu Lys Ser Arg Asn Val Val Ile Ala Ala Asp
    130                 135                 140 gga gta ctg aag atc tgt gac ttt ggt gcc tct cgg ttc cat aac cat      480
Gly Val Leu Lys Ile Cys Asp Phe Gly Ala Ser Arg Phe His Asn His
145                 150                 155                 160 aca aca cac atg tcc ttg gtt gga act ttc cca tgg atg gct cca gaa      528
Thr Thr His Met Ser Leu Val Gly Thr Phe Pro Trp Met Ala Pro Glu
                165                 170                 175 gtt atc cag agt ctc cct gtg tca gaa act tgt gac aca tat tcc tat      576
Val Ile Gln Ser Leu Pro Val Ser Glu Thr Cys Asp Thr Tyr Ser Tyr
            180                 185                 190 ggt gtg gtt ctc tgg gag atg cta aca agg gag gtc ccc ttt aaa ggt      624
Gly Val Val Leu Trp Glu Met Leu Thr Arg Glu Val Pro Phe Lys Gly
        195                 200                 205 ttg gaa gga tta caa gta gct tgg ctt gta gtg gaa aaa aac gag aga      672
Leu Glu Gly Leu Gln Val Ala Trp Leu Val Val Glu Lys Asn Glu Arg
    210                 215                 220 tta acc att cca agc agt tgc ccc aga agt ttt gct gaa ctg tta cat      720
Leu Thr Ile Pro Ser Ser Cys Pro Arg Ser Phe Ala Glu Leu Leu His
225                 230                 235                 240 cag tgt tgg gaa gct gat gcc aag aaa cgg cca tca ttc aag caa atc      768
Gln Cys Trp Glu Ala Asp Ala Lys Lys Arg Pro Ser Phe Lys Gln Ile
                245                 250                 255 att tca atc ctg gag tcc atg tca aat gac acg agc ctt cct gac aag      816
Ile Ser Ile Leu Glu Ser Met Ser Asn Asp Thr Ser Leu Pro Asp Lys
            260                 265                 270 tgt aac tca ttc cta cac aac aag gcg gag tgg agg tgc gaa att gag      864
Cys Asn Ser Phe Leu His Asn Lys Ala Glu Trp Arg Cys Glu Ile Glu
        275                 280                 285 gca act ctt gag agg cta aag aaa cta gag cgt gat ctc agc ttt aag      912
Ala Thr Leu Glu Arg Leu Lys Lys Leu Glu Arg Asp Leu Ser Phe Lys
    290                 295                 300 gag cag gag ctt aaa gaa cga gaa aga cgt tta aag atg tgg gag caa      960
Glu Gln Glu Leu Lys Glu Arg Glu Arg Arg Leu Lys Met Trp Glu Gln
305                 310                 315                 320 aag ctg aca gag cag tcc aac acc ccg ctt ctc ttg cct ctt gct gca     1008
Lys Leu Thr Glu Gln Ser Asn Thr Pro Leu Leu Leu Pro Leu Ala Ala
                325                 330                 335 aga atg tct gag gag tct tac ttt gaa tct aaa aca gag gag tca aac     1056
Arg Met Ser Glu Glu Ser Tyr Phe Glu Ser Lys Thr Glu Glu Ser Asn
            340                 345                 350 agt gca gag atg tca tgt cag atc aca gca aca agt aac ggg gag ggc     1104
Ser Ala Glu Met Ser Cys Gln Ile Thr Ala Thr Ser Asn Gly Glu Gly
        355                 360                 365 cat ggc atg aac cca agt ctg cag gcc atg atg ctg atg ggc ttt ggg     1152
His Gly Met Asn Pro Ser Leu Gln Ala Met Met Leu Met Gly Phe Gly
    370                 375                 380 gat atc ttc tca atg aac aaa gca gga gct gtg atg cat tct ggg atg     1200
Asp Ile Phe Ser Met Asn Lys Ala Gly Ala Val Met His Ser Gly Met
385                 390                 395                 400 cag ata aac atg caa gcc aag cag aat tct tcc aaa acc aca tct aag     1248
Gln Ile Asn Met Gln Ala Lys Gln Asn Ser Ser Lys Thr Thr Ser Lys
                405                 410                 415 aga agg ggg aag aaa gtc aac atg gct ctg ggg ttc agt gat ttt gac     1296
Arg Arg Gly Lys Lys Val Asn Met Ala Leu Gly Phe Ser Asp Phe Asp
            420                 425                 430 ttg tca gaa ggt gac gat gat gat gat gat gac ggt gag gag gag gat     1344
Leu Ser Glu Gly Asp Asp Asp Asp Asp Asp Asp Gly Glu Glu Glu Asp
```

```
                435                 440                 445
aat gac atg gat aat agt gaa                                              1365
Asn Asp Met Asp Asn Ser Glu
    450                 455

<210> SEQ ID NO 7
<211> LENGTH: 2454
<212> TYPE: DNA
<213> ORGANISM: Homo sapiens
<220> FEATURE:
<221> NAME/KEY: CDS
<222> LOCATION: (51)..(1793)

<400> SEQUENCE: 7
cggtggtggc ggcagcggcg gctgcggggg caccgggccg cggcgccacc atg gcg        56
                                                         Met Ala
                                                           1 gtg cga cag gcg ctg ggc cgc ggc ctg cag ctg ggt cga gcg ctg ctg       104
Val Arg Gln Ala Leu Gly Arg Gly Leu Gln Leu Gly Arg Ala Leu Leu
         5                  10                  15 ctg cgc ttc acg ggc aag ccc ggc cgg gcc tac ggc ttg ggc cgg ccg       152
Leu Arg Phe Thr Gly Lys Pro Gly Arg Ala Tyr Gly Leu Gly Arg Pro
     20                  25                  30 ggc ccg gcg gcg ggc tgt gtc cgc ggg gag cgt cca ggc tgg gcc gca       200
Gly Pro Ala Ala Gly Cys Val Arg Gly Glu Arg Pro Gly Trp Ala Ala
 35                  40                  45                  50 gga ccg ggc gcg gag cct cgc agg gtc ggg ctc ggg ctt cct aac cgt       248
Gly Pro Gly Ala Glu Pro Arg Arg Val Gly Leu Gly Leu Pro Asn Arg
                 55                  60                  65 ctc cgc ttc ttc cgc cag tcg gtg gcc ggg ctg gcg gcg cgg ttg cag       296
Leu Arg Phe Phe Arg Gln Ser Val Ala Gly Leu Ala Ala Arg Leu Gln
             70                  75                  80 cgg cag ttc gtg gtg cgg gcc tgg ggc tgc gcg ggc cct tgc ggc cgg       344
Arg Gln Phe Val Val Arg Ala Trp Gly Cys Ala Gly Pro Cys Gly Arg
         85                  90                  95 gca gtc ttt ctg gcc ttc ggg cta ggg ctg ggc ctc atc gag gaa aaa       392
Ala Val Phe Leu Ala Phe Gly Leu Gly Leu Gly Leu Ile Glu Glu Lys
    100                 105                 110 cag gcg gag agc cgg cgg gcg gtc tcg gcc tgt cag gag atc cag gca       440
Gln Ala Glu Ser Arg Arg Ala Val Ser Ala Cys Gln Glu Ile Gln Ala
115                 120                 125                 130 att ttt acc cag aaa agc aag ccg ggg cct gac ccg ttg gac acg aga       488
Ile Phe Thr Gln Lys Ser Lys Pro Gly Pro Asp Pro Leu Asp Thr Arg
                135                 140                 145 cgc ttg cag ggc ttt cgg ctg gag gag tat ctg ata ggg cag tcc att       536
Arg Leu Gln Gly Phe Arg Leu Glu Glu Tyr Leu Ile Gly Gln Ser Ile
            150                 155                 160 ggt aag ggc tgc agt gct gct gtg tat gaa gcc acc atg cct aca ttg       584
Gly Lys Gly Cys Ser Ala Ala Val Tyr Glu Ala Thr Met Pro Thr Leu
        165                 170                 175 ccc cag aac ctg gag gtg aca aag agc acc ggg ttg ctt cca ggg aga       632
Pro Gln Asn Leu Glu Val Thr Lys Ser Thr Gly Leu Leu Pro Gly Arg
    180                 185                 190 ggc cca ggt acc agt gca cca gga gaa ggg cag gag cga gct ccg ggg       680
Gly Pro Gly Thr Ser Ala Pro Gly Glu Gly Gln Glu Arg Ala Pro Gly
195                 200                 205                 210 gcc cct gcc ttc ccc ttg gcc atc aag atg atg tgg aac atc tcg gca       728
Ala Pro Ala Phe Pro Leu Ala Ile Lys Met Met Trp Asn Ile Ser Ala
                215                 220                 225 ggt tcc tcc agc gaa gcc atc ttg aac aca atg agc cag gag ctg gtc       776
Gly Ser Ser Ser Glu Ala Ile Leu Asn Thr Met Ser Gln Glu Leu Val
            230                 235                 240
```

-continued

| | | | | | | | | | | | | | | | |
|---|---|---|---|---|---|---|---|---|---|---|---|---|---|---|---|
| | | 230 | | | | 235 | | | | 240 | | | | | |
| cca | gcg | agc | cga | gtg | gcc | ttg | gct | ggg | gag | tat | gga | gca | gtc | act | tac | 824 |
| Pro | Ala | Ser | Arg | Val | Ala | Leu | Ala | Gly | Glu | Tyr | Gly | Ala | Val | Thr | Tyr |
| | | 245 | | | | 250 | | | | 255 | | | | | |

| aga | aaa | tcc | aag | aga | ggt | ccc | aag | caa | cta | gcc | cct | cac | ccc | aac | atc | 872 |
|---|---|---|---|---|---|---|---|---|---|---|---|---|---|---|---|---|
| Arg | Lys | Ser | Lys | Arg | Gly | Pro | Lys | Gln | Leu | Ala | Pro | His | Pro | Asn | Ile |
| | 260 | | | | | 265 | | | | | 270 | | | | |

| atc | cgg | gtt | ctc | cgc | gcc | ttc | acc | tct | tcc | gtg | ccg | ctg | ctg | cca | ggg | 920 |
|---|---|---|---|---|---|---|---|---|---|---|---|---|---|---|---|---|
| Ile | Arg | Val | Leu | Arg | Ala | Phe | Thr | Ser | Ser | Val | Pro | Leu | Leu | Pro | Gly |
| 275 | | | | | 280 | | | | | 285 | | | | | 290 |

| gcc | ctg | gtc | gac | tac | cct | gat | gtg | ctg | ccc | tca | cgc | ctc | cac | cct | gaa | 968 |
|---|---|---|---|---|---|---|---|---|---|---|---|---|---|---|---|---|
| Ala | Leu | Val | Asp | Tyr | Pro | Asp | Val | Leu | Pro | Ser | Arg | Leu | His | Pro | Glu |
| | | | | 295 | | | | | 300 | | | | | 305 | |

| ggc | ctg | ggc | cat | ggc | cgg | acg | ctg | ttc | ctc | gtt | atg | aag | aac | tat | ccc | 1016 |
|---|---|---|---|---|---|---|---|---|---|---|---|---|---|---|---|---|
| Gly | Leu | Gly | His | Gly | Arg | Thr | Leu | Phe | Leu | Val | Met | Lys | Asn | Tyr | Pro |
| | | | 310 | | | | | 315 | | | | | 320 | | |

| tgt | acc | ctg | cgc | cag | tac | ctt | tgt | gtg | aac | aca | ccc | agc | ccc | cgc | ctc | 1064 |
|---|---|---|---|---|---|---|---|---|---|---|---|---|---|---|---|---|
| Cys | Thr | Leu | Arg | Gln | Tyr | Leu | Cys | Val | Asn | Thr | Pro | Ser | Pro | Arg | Leu |
| | | 325 | | | | | 330 | | | | | 335 | | | |

| gcc | gcc | atg | atg | ctg | ctg | cag | ctg | ctg | gaa | ggc | gtg | gac | cat | ctg | gtt | 1112 |
|---|---|---|---|---|---|---|---|---|---|---|---|---|---|---|---|---|
| Ala | Ala | Met | Met | Leu | Leu | Gln | Leu | Leu | Glu | Gly | Val | Asp | His | Leu | Val |
| | 340 | | | | | 345 | | | | | 350 | | | | |

| caa | cag | ggc | atc | gcg | cac | aga | gac | ctg | aaa | tcc | gac | aac | atc | ctt | gtg | 1160 |
|---|---|---|---|---|---|---|---|---|---|---|---|---|---|---|---|---|
| Gln | Gln | Gly | Ile | Ala | His | Arg | Asp | Leu | Lys | Ser | Asp | Asn | Ile | Leu | Val |
| 355 | | | | | 360 | | | | | 365 | | | | | 370 |

| gag | ctg | gac | cca | gac | ggc | tgc | ccc | tgg | ctg | gtg | atc | gca | gat | ttt | ggc | 1208 |
|---|---|---|---|---|---|---|---|---|---|---|---|---|---|---|---|---|
| Glu | Leu | Asp | Pro | Asp | Gly | Cys | Pro | Trp | Leu | Val | Ile | Ala | Asp | Phe | Gly |
| | | | | 375 | | | | | 380 | | | | | 385 | |

| tgc | tgc | ctg | gct | gat | gag | agc | atc | ggc | ctg | cag | ttg | ccc | ttc | agc | agc | 1256 |
|---|---|---|---|---|---|---|---|---|---|---|---|---|---|---|---|---|
| Cys | Cys | Leu | Ala | Asp | Glu | Ser | Ile | Gly | Leu | Gln | Leu | Pro | Phe | Ser | Ser |
| | | | 390 | | | | | 395 | | | | | 400 | | |

| tgg | tac | gtg | gat | cgg | ggc | gga | aac | ggc | tgt | ctg | atg | gcc | cca | gag | gtg | 1304 |
|---|---|---|---|---|---|---|---|---|---|---|---|---|---|---|---|---|
| Trp | Tyr | Val | Asp | Arg | Gly | Gly | Asn | Gly | Cys | Leu | Met | Ala | Pro | Glu | Val |
| | | 405 | | | | | 410 | | | | | 415 | | | |

| tcc | acg | gcc | cgt | cct | ggc | ccc | agg | gca | gtg | att | gac | tac | agc | aag | gct | 1352 |
|---|---|---|---|---|---|---|---|---|---|---|---|---|---|---|---|---|
| Ser | Thr | Ala | Arg | Pro | Gly | Pro | Arg | Ala | Val | Ile | Asp | Tyr | Ser | Lys | Ala |
| | 420 | | | | | 425 | | | | | 430 | | | | |

| gat | gcc | tgg | gca | gtg | gga | gcc | atc | gcc | tat | gaa | atc | ttc | ggg | ctt | gtc | 1400 |
|---|---|---|---|---|---|---|---|---|---|---|---|---|---|---|---|---|
| Asp | Ala | Trp | Ala | Val | Gly | Ala | Ile | Ala | Tyr | Glu | Ile | Phe | Gly | Leu | Val |
| 435 | | | | | 440 | | | | | 445 | | | | | 450 |

| aat | ccc | ttc | tac | ggc | cag | ggc | aag | gcc | cac | ctt | gaa | agc | cgc | agc | tac | 1448 |
|---|---|---|---|---|---|---|---|---|---|---|---|---|---|---|---|---|
| Asn | Pro | Phe | Tyr | Gly | Gln | Gly | Lys | Ala | His | Leu | Glu | Ser | Arg | Ser | Tyr |
| | | | | 455 | | | | | 460 | | | | | 465 | |

| caa | gag | gct | cag | cta | cct | gca | ctg | ccc | gag | tca | gtg | cct | cca | gac | gtg | 1496 |
|---|---|---|---|---|---|---|---|---|---|---|---|---|---|---|---|---|
| Gln | Glu | Ala | Gln | Leu | Pro | Ala | Leu | Pro | Glu | Ser | Val | Pro | Pro | Asp | Val |
| | | | 470 | | | | | 475 | | | | | 480 | | |

| aga | cag | ttg | gtg | agg | gca | ctg | ctc | cag | cga | gag | gcc | agc | aag | aga | cca | 1544 |
|---|---|---|---|---|---|---|---|---|---|---|---|---|---|---|---|---|
| Arg | Gln | Leu | Val | Arg | Ala | Leu | Leu | Gln | Arg | Glu | Ala | Ser | Lys | Arg | Pro |
| | | 485 | | | | | 490 | | | | | 495 | | | |

| tct | gcc | cga | gta | gcc | gca | aat | gtg | ctt | cat | cta | agc | ctc | tgg | ggt | gaa | 1592 |
|---|---|---|---|---|---|---|---|---|---|---|---|---|---|---|---|---|
| Ser | Ala | Arg | Val | Ala | Ala | Asn | Val | Leu | His | Leu | Ser | Leu | Trp | Gly | Glu |
| | 500 | | | | | 505 | | | | | 510 | | | | |

| cat | att | cta | gcc | ctg | aag | aat | ctg | aag | tta | gac | aag | atg | gtt | ggc | tgg | 1640 |
|---|---|---|---|---|---|---|---|---|---|---|---|---|---|---|---|---|
| His | Ile | Leu | Ala | Leu | Lys | Asn | Leu | Lys | Leu | Asp | Lys | Met | Val | Gly | Trp |
| 515 | | | | | 520 | | | | | 525 | | | | | 530 |

| ctc | ctc | caa | caa | tcg | gcc | gcc | act | ttg | ttg | gcc | aac | agg | ctc | aca | gag | 1688 |
|---|---|---|---|---|---|---|---|---|---|---|---|---|---|---|---|---|
| Leu | Leu | Gln | Gln | Ser | Ala | Ala | Thr | Leu | Leu | Ala | Asn | Arg | Leu | Thr | Glu |
| | | | | 535 | | | | | 540 | | | | | 545 | |

| aag | tgt | tgt | gtg | gaa | aca | aaa | atg | aag | atg | ctc | ttt | ctg | gct | aac | ctg | 1736 |
|---|---|---|---|---|---|---|---|---|---|---|---|---|---|---|---|---|

-continued

```
                      Lys Cys Cys Val Glu Thr Lys Met Lys Met Leu Phe Leu Ala Asn Leu
                                      550                 555                 560 gag tgt gaa acg ctc tgc cag gca gcc ctc ctc ctc tgc tca tgg agg              1784
Glu Cys Glu Thr Leu Cys Gln Ala Ala Leu Leu Leu Cys Ser Trp Arg
            565                 570                 575 gca gcc ctg tgatgtccct gcatggagct ggtgaattac taaaagaact                       1833
Ala Ala Leu
    580 tggcatcctc tgtgtcgtga tggtctgtga atggtgaggg tgggagtcag gagacaagac             1893 agcgcagaga gggctggtta gccggaaaag gcctcgggct tggcaaatgg aagaacttga             1953 gtgagagttc agtctgcagt cctctgctca cagacatctg aaaagtgaat ggccaagctg             2013 gtctagtaga tgaggctgga ctgaggaggg gtaggcctgc atccacagag aggatccagg             2073 ccaaggcact ggctgtcagt ggcagagttt ggctgtgacc tttgcccta acacgaggaa              2133 ctcgtttgaa gggggcagcg tagcatgtct gatttgccac ctggatgaag cagacatca              2193 acatgggtca gcacgttcag ttacgggagt gggaaattac atgaggcctg gcctctgcg              2253 ttcccaagct gtgcgttctg gaccagctac tgaattatta atctcactta gcaaagtga              2313 cggatgagca gtaagtaagt aagtgtgggg atttaaactt gagggtttcc ctcctgacta             2373 gcctctctta caggaattgt gaatattaa atgcaaattt acaactgcaa aaaaaaaaa               2433 aaaaaaaaaa aagggcggcc c                                                       2454

<210> SEQ ID NO 8
<211> LENGTH: 581
<212> TYPE: PRT
<213> ORGANISM: Homo sapiens

<400> SEQUENCE: 8

Met Ala Val Arg Gln Ala Leu Gly Arg Gly Leu Gln Leu Gly Arg Ala
 1               5                  10                  15

Leu Leu Leu Arg Phe Thr Gly Lys Pro Gly Arg Ala Tyr Gly Leu Gly
                20                  25                  30

Arg Pro Gly Pro Ala Ala Gly Cys Val Arg Gly Glu Arg Pro Gly Trp
            35                  40                  45

Ala Ala Gly Pro Gly Ala Glu Pro Arg Arg Val Gly Leu Gly Leu Pro
        50                  55                  60

Asn Arg Leu Arg Phe Phe Arg Gln Ser Val Ala Gly Leu Ala Ala Arg
65                  70                  75                  80

Leu Gln Arg Gln Phe Val Val Arg Ala Trp Gly Cys Ala Gly Pro Cys
                85                  90                  95

Gly Arg Ala Val Phe Leu Ala Phe Gly Leu Gly Leu Gly Leu Ile Glu
            100                 105                 110

Glu Lys Gln Ala Glu Ser Arg Arg Ala Val Ser Ala Cys Gln Glu Ile
        115                 120                 125

Gln Ala Ile Phe Thr Gln Lys Ser Lys Pro Gly Pro Asp Pro Leu Asp
    130                 135                 140

Thr Arg Arg Leu Gln Gly Phe Arg Leu Glu Glu Tyr Leu Ile Gly Gln
145                 150                 155                 160

Ser Ile Gly Lys Gly Cys Ser Ala Ala Val Tyr Glu Ala Thr Met Pro
                165                 170                 175

Thr Leu Pro Gln Asn Leu Glu Val Thr Lys Ser Thr Gly Leu Leu Pro
            180                 185                 190

Gly Arg Gly Pro Gly Thr Ser Ala Pro Gly Glu Gly Gln Glu Arg Ala
        195                 200                 205
```

```
Pro Gly Ala Pro Ala Phe Pro Leu Ala Ile Lys Met Met Trp Asn Ile
    210                 215                 220
Ser Ala Gly Ser Ser Ser Glu Ala Ile Leu Asn Thr Met Ser Gln Glu
225                 230                 235                 240
Leu Val Pro Ala Ser Arg Val Ala Leu Ala Gly Glu Tyr Gly Ala Val
                245                 250                 255
Thr Tyr Arg Lys Ser Lys Arg Gly Pro Lys Gln Leu Ala Pro His Pro
            260                 265                 270
Asn Ile Ile Arg Val Leu Arg Ala Phe Thr Ser Val Pro Leu Leu
                275                 280                 285
Pro Gly Ala Leu Val Asp Tyr Pro Asp Val Leu Pro Ser Arg Leu His
    290                 295                 300
Pro Glu Gly Leu Gly His Gly Arg Thr Leu Phe Leu Val Met Lys Asn
305                 310                 315                 320
Tyr Pro Cys Thr Leu Arg Gln Tyr Leu Cys Val Asn Thr Pro Ser Pro
                325                 330                 335
Arg Leu Ala Ala Met Met Leu Leu Gln Leu Leu Glu Gly Val Asp His
            340                 345                 350
Leu Val Gln Gln Gly Ile Ala His Arg Asp Leu Lys Ser Asp Asn Ile
                355                 360                 365
Leu Val Glu Leu Asp Pro Asp Gly Cys Pro Trp Leu Val Ile Ala Asp
    370                 375                 380
Phe Gly Cys Cys Leu Ala Asp Glu Ser Ile Gly Leu Gln Leu Pro Phe
385                 390                 395                 400
Ser Ser Trp Tyr Val Asp Arg Gly Gly Asn Gly Cys Leu Met Ala Pro
                405                 410                 415
Glu Val Ser Thr Ala Arg Pro Gly Pro Arg Ala Val Ile Asp Tyr Ser
            420                 425                 430
Lys Ala Asp Ala Trp Ala Val Gly Ala Ile Ala Tyr Glu Ile Phe Gly
                435                 440                 445
Leu Val Asn Pro Phe Tyr Gly Gln Gly Lys Ala His Leu Glu Ser Arg
    450                 455                 460
Ser Tyr Gln Glu Ala Gln Leu Pro Ala Leu Pro Glu Ser Val Pro Pro
465                 470                 475                 480
Asp Val Arg Gln Leu Val Arg Ala Leu Leu Gln Arg Glu Ala Ser Lys
                485                 490                 495
Arg Pro Ser Ala Arg Val Ala Ala Asn Val Leu His Leu Ser Leu Trp
            500                 505                 510
Gly Glu His Ile Leu Ala Leu Lys Asn Leu Lys Leu Asp Lys Met Val
                515                 520                 525
Gly Trp Leu Leu Gln Gln Ser Ala Ala Thr Leu Leu Ala Asn Arg Leu
    530                 535                 540
Thr Glu Lys Cys Cys Val Glu Thr Lys Met Lys Met Leu Phe Leu Ala
545                 550                 555                 560
Asn Leu Glu Cys Glu Thr Leu Cys Gln Ala Ala Leu Leu Leu Cys Ser
                565                 570                 575
Trp Arg Ala Ala Leu
            580

<210> SEQ ID NO 9
<211> LENGTH: 1743
<212> TYPE: DNA
<213> ORGANISM: Homo sapiens
<220> FEATURE:
```

-continued

```
<221> NAME/KEY: CDS
<222> LOCATION: (1)..(1743)

<400> SEQUENCE: 9
```

| | | | | | | | | | | | | | | | | |
|---|---|---|---|---|---|---|---|---|---|---|---|---|---|---|---|---|
| atg | gcg | gtg | cga | cag | gcg | ctg | ggc | cgc | ggc | ctg | cag | ctg | ggt | cga | gcg | 48 |
| Met | Ala | Val | Arg | Gln | Ala | Leu | Gly | Arg | Gly | Leu | Gln | Leu | Gly | Arg | Ala | |
| 1 | | | | 5 | | | | | 10 | | | | | 15 | | |
| ctg | ctg | ctg | cgc | ttc | acg | ggc | aag | ccc | ggc | cgg | gcc | tac | ggc | ttg | ggg | 96 |
| Leu | Leu | Leu | Arg | Phe | Thr | Gly | Lys | Pro | Gly | Arg | Ala | Tyr | Gly | Leu | Gly | |
| | | | 20 | | | | | 25 | | | | | 30 | | | |
| cgg | ccg | ggc | ccg | gcg | gcg | ggc | tgt | gtc | cgc | ggg | gag | cgt | cca | ggc | tgg | 144 |
| Arg | Pro | Gly | Pro | Ala | Ala | Gly | Cys | Val | Arg | Gly | Glu | Arg | Pro | Gly | Trp | |
| | 35 | | | | | 40 | | | | | 45 | | | | | |
| gcc | gca | gga | ccg | ggc | gcg | gag | cct | cgc | agg | gtc | ggg | ctc | ggg | ctt | cct | 192 |
| Ala | Ala | Gly | Pro | Gly | Ala | Glu | Pro | Arg | Arg | Val | Gly | Leu | Gly | Leu | Pro | |
| 50 | | | | | 55 | | | | | 60 | | | | | | |
| aac | cgt | ctc | cgc | ttc | ttc | cgc | cag | tcg | gtg | gcc | ggg | ctg | gcg | gcg | cgg | 240 |
| Asn | Arg | Leu | Arg | Phe | Phe | Arg | Gln | Ser | Val | Ala | Gly | Leu | Ala | Ala | Arg | |
| 65 | | | | 70 | | | | | 75 | | | | | 80 | | |
| ttg | cag | cgg | cag | ttc | gtg | gtg | cgg | gcc | tgg | ggc | tgc | gcg | ggc | cct | tgc | 288 |
| Leu | Gln | Arg | Gln | Phe | Val | Val | Arg | Ala | Trp | Gly | Cys | Ala | Gly | Pro | Cys | |
| | | | | 85 | | | | | 90 | | | | | 95 | | |
| ggc | cgg | gca | gtc | ttt | ctg | gcc | ttc | ggg | cta | ggg | ctg | ggc | ctc | atc | gag | 336 |
| Gly | Arg | Ala | Val | Phe | Leu | Ala | Phe | Gly | Leu | Gly | Leu | Gly | Leu | Ile | Glu | |
| | | | 100 | | | | | 105 | | | | | 110 | | | |
| gaa | aaa | cag | gcg | gag | agc | cgg | cgg | gcg | gtc | tcg | gcc | tgt | cag | gag | atc | 384 |
| Glu | Lys | Gln | Ala | Glu | Ser | Arg | Arg | Ala | Val | Ser | Ala | Cys | Gln | Glu | Ile | |
| | | 115 | | | | | 120 | | | | | 125 | | | | |
| cag | gca | att | ttt | acc | cag | aaa | agc | aag | ccg | ggg | cct | gac | ccg | ttg | gac | 432 |
| Gln | Ala | Ile | Phe | Thr | Gln | Lys | Ser | Lys | Pro | Gly | Pro | Asp | Pro | Leu | Asp | |
| 130 | | | | | 135 | | | | | 140 | | | | | | |
| acg | aga | cgc | ttg | cag | ggc | ttt | cgg | ctg | gag | gag | tat | ctg | ata | ggg | cag | 480 |
| Thr | Arg | Arg | Leu | Gln | Gly | Phe | Arg | Leu | Glu | Glu | Tyr | Leu | Ile | Gly | Gln | |
| 145 | | | | | 150 | | | | | 155 | | | | | 160 | |
| tcc | att | ggt | aag | ggc | tgc | agt | gct | gct | gtg | tat | gaa | gcc | acc | atg | cct | 528 |
| Ser | Ile | Gly | Lys | Gly | Cys | Ser | Ala | Ala | Val | Tyr | Glu | Ala | Thr | Met | Pro | |
| | | | | 165 | | | | | 170 | | | | | 175 | | |
| aca | ttg | ccc | cag | aac | ctg | gag | gtg | aca | aag | agc | acc | ggg | ttg | ctt | cca | 576 |
| Thr | Leu | Pro | Gln | Asn | Leu | Glu | Val | Thr | Lys | Ser | Thr | Gly | Leu | Leu | Pro | |
| | | | 180 | | | | | 185 | | | | | 190 | | | |
| ggg | aga | ggc | cca | ggt | acc | agt | gca | cca | gga | gaa | ggg | cag | gag | cga | gct | 624 |
| Gly | Arg | Gly | Pro | Gly | Thr | Ser | Ala | Pro | Gly | Glu | Gly | Gln | Glu | Arg | Ala | |
| | 195 | | | | | 200 | | | | | 205 | | | | | |
| ccg | ggg | gcc | cct | gcc | ttc | ccc | ttg | gcc | atc | aag | atg | atg | tgg | aac | atc | 672 |
| Pro | Gly | Ala | Pro | Ala | Phe | Pro | Leu | Ala | Ile | Lys | Met | Met | Trp | Asn | Ile | |
| 210 | | | | | 215 | | | | | 220 | | | | | | |
| tcg | gca | ggt | tcc | tcc | agc | gaa | gcc | atc | ttg | aac | aca | atg | agc | cag | gag | 720 |
| Ser | Ala | Gly | Ser | Ser | Ser | Glu | Ala | Ile | Leu | Asn | Thr | Met | Ser | Gln | Glu | |
| 225 | | | | | 230 | | | | | 235 | | | | | 240 | |
| ctg | gtc | cca | gcg | agc | cga | gtg | gcc | ttg | gct | ggg | gag | tat | gga | gca | gtc | 768 |
| Leu | Val | Pro | Ala | Ser | Arg | Val | Ala | Leu | Ala | Gly | Glu | Tyr | Gly | Ala | Val | |
| | | | | 245 | | | | | 250 | | | | | 255 | | |
| act | tac | aga | aaa | tcc | aag | aga | ggt | ccc | aag | caa | cta | gcc | cct | cac | ccc | 816 |
| Thr | Tyr | Arg | Lys | Ser | Lys | Arg | Gly | Pro | Lys | Gln | Leu | Ala | Pro | His | Pro | |
| | | | 260 | | | | | 265 | | | | | 270 | | | |
| aac | atc | atc | cgg | gtt | ctc | cgc | gcc | ttc | acc | tct | tcc | gtg | ccg | ctg | ctg | 864 |
| Asn | Ile | Ile | Arg | Val | Leu | Arg | Ala | Phe | Thr | Ser | Ser | Val | Pro | Leu | Leu | |
| | | 275 | | | | | 280 | | | | | 285 | | | | |
| cca | ggg | gcc | ctg | gtc | gac | tac | cct | gat | gtg | ctg | ccc | tca | cgc | ctc | cac | 912 |
| Pro | Gly | Ala | Leu | Val | Asp | Tyr | Pro | Asp | Val | Leu | Pro | Ser | Arg | Leu | His | |

```
            290                 295                 300
cct gaa ggc ctg ggc cat ggc cgg acg ctg ttc ctc gtt atg aag aac      960
Pro Glu Gly Leu Gly His Gly Arg Thr Leu Phe Leu Val Met Lys Asn
305                 310                 315                 320 tat ccc tgt acc ctg cgc cag tac ctt tgt gtg aac aca ccc agc ccc     1008
Tyr Pro Cys Thr Leu Arg Gln Tyr Leu Cys Val Asn Thr Pro Ser Pro
                325                 330                 335 cgc ctc gcc gcc atg atg ctg ctg cag ctg ctg gaa ggc gtg gac cat     1056
Arg Leu Ala Ala Met Met Leu Leu Gln Leu Leu Glu Gly Val Asp His
            340                 345                 350 ctg gtt caa cag ggc atc gcg cac aga gac ctg aaa tcc gac aac atc     1104
Leu Val Gln Gln Gly Ile Ala His Arg Asp Leu Lys Ser Asp Asn Ile
        355                 360                 365 ctt gtg gag ctg gac cca gac ggc tgc ccc tgg ctg gtg atc gca gat     1152
Leu Val Glu Leu Asp Pro Asp Gly Cys Pro Trp Leu Val Ile Ala Asp
370                 375                 380 ttt ggc tgc tgc ctg gct gat gag agc atc ggc ctg cag ttg ccc ttc     1200
Phe Gly Cys Cys Leu Ala Asp Glu Ser Ile Gly Leu Gln Leu Pro Phe
385                 390                 395                 400 agc agc tgg tac gtg gat cgg ggc gga aac ggc tgt ctg atg gcc cca     1248
Ser Ser Trp Tyr Val Asp Arg Gly Gly Asn Gly Cys Leu Met Ala Pro
                405                 410                 415 gag gtg tcc acg gcc cgt cct ggc ccc agg gca gtg att gac tac agc     1296
Glu Val Ser Thr Ala Arg Pro Gly Pro Arg Ala Val Ile Asp Tyr Ser
            420                 425                 430 aag gct gat gcc tgg gca gtg gga gcc atc gcc tat gaa atc ttc ggg     1344
Lys Ala Asp Ala Trp Ala Val Gly Ala Ile Ala Tyr Glu Ile Phe Gly
        435                 440                 445 ctt gtc aat ccc ttc tac ggc cag ggc aag gcc cac ctt gaa agc cgc     1392
Leu Val Asn Pro Phe Tyr Gly Gln Gly Lys Ala His Leu Glu Ser Arg
    450                 455                 460 agc tac caa gag gct cag cta cct gca ctg ccc gag tca gtg cct cca     1440
Ser Tyr Gln Glu Ala Gln Leu Pro Ala Leu Pro Glu Ser Val Pro Pro
465                 470                 475                 480 gac gtg aga cag ttg gtg agg gca ctc ctc cag cga gag gcc agc aag     1488
Asp Val Arg Gln Leu Val Arg Ala Leu Leu Gln Arg Glu Ala Ser Lys
                485                 490                 495 aga cca tct gcc cga gta gcc gca aat gtg ctt cat cta agc ctc tgg     1536
Arg Pro Ser Ala Arg Val Ala Ala Asn Val Leu His Leu Ser Leu Trp
            500                 505                 510 ggt gaa cat att cta gcc ctg aag aat ctg aag tta gac aag atg gtt     1584
Gly Glu His Ile Leu Ala Leu Lys Asn Leu Lys Leu Asp Lys Met Val
        515                 520                 525 ggc tgg ctc ctc caa caa tcg gcc gcc act ttg ttg gcc aac agg ctc     1632
Gly Trp Leu Leu Gln Gln Ser Ala Ala Thr Leu Leu Ala Asn Arg Leu
    530                 535                 540 aca gag aag tgt tgt gtg gaa aca aaa atg aag atg ctc ttt ctg gct     1680
Thr Glu Lys Cys Cys Val Glu Thr Lys Met Lys Met Leu Phe Leu Ala
545                 550                 555                 560 aac ctg gag tgt gaa acg ctc tgc cag gca gcc ctc ctc ctc tgc tca     1728
Asn Leu Glu Cys Glu Thr Leu Cys Gln Ala Ala Leu Leu Leu Cys Ser
                565                 570                 575 tgg agg gca gcc ctg                                                  1743
Trp Arg Ala Ala Leu
            580

<210> SEQ ID NO 10
<211> LENGTH: 1864
<212> TYPE: DNA
<213> ORGANISM: Homo sapiens
```

```
<220> FEATURE:
<221> NAME/KEY: CDS
<222> LOCATION: (275)..(754)

<400> SEQUENCE: 10
gtcgacccac gcggtccgcc cacgcgttcc ggagacatgt ctctgtgttt ctctcccctc     60
cgcttttgag tccgttgaag acacaatttc tctctgtcgg gtgcttagga ggagctccat    120
gaacatgtat tgaattggac ttagctgaac aggctgctgg ttggctgccc agaggggggca   180 ggctgtgttg ctgggagcct ccagctccc tgcagcagtc atggggcagg ttccccgag     240 tccgtaatcc ccatttccac ctactttccc ttag tta ttt gat tcc ctg tct gtc   295
                                       Leu Phe Asp Ser Leu Ser Val
                                        1               5 gta ctc agc tta agt gga gca tcc cct ttc ctg gga gac acg aag cag     343
Val Leu Ser Leu Ser Gly Ala Ser Pro Phe Leu Gly Asp Thr Lys Gln
        10                  15                  20 gaa aca ctg gca aat atc aca gca gtg agt tac gac ttt gat gag gaa     391
Glu Thr Leu Ala Asn Ile Thr Ala Val Ser Tyr Asp Phe Asp Glu Glu
    25                  30                  35 ttc ttc agc cag acg agc gag ctg gcc aag gac ttt att cgg aag ctt     439
Phe Phe Ser Gln Thr Ser Glu Leu Ala Lys Asp Phe Ile Arg Lys Leu
40                  45                  50                  55 ctg gtt aaa gag acc cgg aaa cgg ctc aca atc caa gag gct ctc aga     487
Leu Val Lys Glu Thr Arg Lys Arg Leu Thr Ile Gln Glu Ala Leu Arg
                60                  65                  70 cac ccc tgg atc acg ccg gtg gac aac cag caa gcc atg gtg cgc agg     535
His Pro Trp Ile Thr Pro Val Asp Asn Gln Gln Ala Met Val Arg Arg
            75                  80                  85 gag tct gtg gtc aat ctg gag aac ttc agg aag cag tat gtc cgc agg     583
Glu Ser Val Val Asn Leu Glu Asn Phe Arg Lys Gln Tyr Val Arg Arg
        90                  95                  100 cgg tgg aag ctt tcc ttc agc atc gtg tcc ctg tgc aac cac ctc acc     631
Arg Trp Lys Leu Ser Phe Ser Ile Val Ser Leu Cys Asn His Leu Thr
    105                 110                 115 cgc tcg ctg atg aag aag gtg cac ctg agg ccg gat gag gac ctg agg     679
Arg Ser Leu Met Lys Lys Val His Leu Arg Pro Asp Glu Asp Leu Arg
120                 125                 130                 135 aac tgt gag agt gac act gag gag gac atc gcc agg agg aaa gcc ctc     727
Asn Cys Glu Ser Asp Thr Glu Glu Asp Ile Ala Arg Arg Lys Ala Leu
                140                 145                 150 cac cca cgg agg agg agc agc acc tcc taactggcct gacctgcagt           774
His Pro Arg Arg Arg Ser Ser Thr Ser
            155                 160 ggccgccagg gaggtctggg cccagcgggg ctcccttctg tgcagacttt tggacccagc    834
tcagcaccag caccccgggcg tcctgagcac tttgcaagag agatgggccc aaggaattca   894
gaagagcttg caggcaagcc aggagaccct gggagctgtg ctgtcttct gtggaggagg    954 ctccagcatt cccaaagctc ttaattctcc ataaaatggg ctttcctctg tctgccatcc   1014
tcagagtctg gggtgggagt gtggacttag gaaaacaata taaaggacat cctcatcatc   1074 acgggtgaa ggtcagacta aggcagcctt cttcacaggc tgagggggtt cagaaccagc   1134
ctggccaaaa attacaccag agagacagag tcctccccat tgggaacagg gtgattgagg   1194
aaagtgaacc ttgggtgtga gggaccaatc ctgtgacctc ccagaaccat ggaagccagg   1254
acgtcaggct gaccaacacc tcagaccttg tgaagcagcc cattgctggc ccgccatgtt   1314
gtaattttgc tcatttttat taaacttctg gtttacctga tgcttggctt cttttagggc   1374
tacccccatc tcatttcctt tagcccgtgt gcctgtaact ctgaggggg gcacccagtg    1434
```

```
gggtgctgag tgggcagaat ctcagaaggt cctcctgaac cgtccgcgca ggcctgcagt      1494 ggcctgcct cctccttgct tccctaacag gaaggtgtcc agttcaagag aacccaccca       1554
gagactggga gtggtggctc acgcctataa tccctgcgct ttggcagtcc gaggcagggg      1614
aattgcttga actcaggagt tggagaccag cctgggcaac atggcaaaac gcagtctgta      1674
caaaaaatac aaaaaattag ccaggtgtag gggtaggcac ctggcatccc agctactcca     1734
ggggctgagg tgacagcatt gcttaagccc agaaggtcga ggctgcagtg agctgagatc      1794
acgccactgc actccagtct gggtgacaga gagagaccat atccaaaaaa aaaaaaaaa       1854 gggcggccgc                                                              1864
```

<210> SEQ ID NO 11
<211> LENGTH: 160
<212> TYPE: PRT
<213> ORGANISM: Homo sapiens

<400> SEQUENCE: 11

```
Leu Phe Asp Ser Leu Ser Val Val Leu Ser Leu Ser Gly Ala Ser Pro
  1               5                  10                  15

Phe Leu Gly Asp Thr Lys Gln Glu Thr Leu Ala Asn Ile Thr Ala Val
             20                  25                  30

Ser Tyr Asp Phe Asp Glu Glu Phe Phe Ser Gln Thr Ser Glu Leu Ala
         35                  40                  45

Lys Asp Phe Ile Arg Lys Leu Leu Val Lys Glu Thr Arg Lys Arg Leu
     50                  55                  60

Thr Ile Gln Glu Ala Leu Arg His Pro Trp Ile Thr Pro Val Asp Asn
 65                  70                  75                  80

Gln Gln Ala Met Val Arg Arg Glu Ser Val Val Asn Leu Glu Asn Phe
                 85                  90                  95

Arg Lys Gln Tyr Val Arg Arg Trp Lys Leu Ser Phe Ser Ile Val
            100                 105                 110

Ser Leu Cys Asn His Leu Thr Arg Ser Leu Met Lys Lys Val His Leu
        115                 120                 125

Arg Pro Asp Glu Asp Leu Arg Asn Cys Glu Ser Asp Thr Glu Glu Asp
    130                 135                 140

Ile Ala Arg Arg Lys Ala Leu His Pro Arg Arg Arg Ser Ser Thr Ser
145                 150                 155                 160
```

<210> SEQ ID NO 12
<211> LENGTH: 480
<212> TYPE: DNA
<213> ORGANISM: Homo sapiens
<220> FEATURE:
<221> NAME/KEY: CDS
<222> LOCATION: (1)..(480)

<400> SEQUENCE: 12

```
tta ttt gat tcc ctg tct gtc gta ctc agc tta agt gga gca tcc cct        48
Leu Phe Asp Ser Leu Ser Val Val Leu Ser Leu Ser Gly Ala Ser Pro
  1               5                  10                  15 ttc ctg gga gac acg aag cag gaa aca ctg gca aat atc aca gca gtg        96
Phe Leu Gly Asp Thr Lys Gln Glu Thr Leu Ala Asn Ile Thr Ala Val
             20                  25                  30 agt tac gac ttt gat gag gaa ttc ttc agc cag acg agc gag ctg gcc       144
Ser Tyr Asp Phe Asp Glu Glu Phe Phe Ser Gln Thr Ser Glu Leu Ala
         35                  40                  45 aag gac ttt att cgg aag ctt ctg gtt aaa gag acc cgg aaa cgg ctc       192
```

```
Lys Asp Phe Ile Arg Lys Leu Leu Val Lys Glu Thr Arg Lys Arg Leu
 50                  55                  60 aca atc caa gag gct ctc aga cac ccc tgg atc acg ccg gtg gac aac      240
Thr Ile Gln Glu Ala Leu Arg His Pro Trp Ile Thr Pro Val Asp Asn
 65                  70                  75                  80 cag caa gcc atg gtg cgc agg gag tct gtg gtc aat ctg gag aac ttc      288
Gln Gln Ala Met Val Arg Arg Glu Ser Val Val Asn Leu Glu Asn Phe
                 85                  90                  95 agg aag cag tat gtc cgc agg cgg tgg aag ctt tcc ttc agc atc gtg      336
Arg Lys Gln Tyr Val Arg Arg Arg Trp Lys Leu Ser Phe Ser Ile Val
            100                 105                 110 tcc ctg tgc aac cac ctc acc cgc tcg ctg atg aag aag gtg cac ctg      384
Ser Leu Cys Asn His Leu Thr Arg Ser Leu Met Lys Lys Val His Leu
        115                 120                 125 agg ccg gat gag gac ctg agg aac tgt gag agt gac act gag gag gac      432
Arg Pro Asp Glu Asp Leu Arg Asn Cys Glu Ser Asp Thr Glu Glu Asp
    130                 135                 140 atc gcc agg agg aaa gcc ctc cac cca cgg agg agg agc agc acc tcc      480
Ile Ala Arg Arg Lys Ala Leu His Pro Arg Arg Arg Ser Ser Thr Ser
145                 150                 155                 160

<210> SEQ ID NO 13
<211> LENGTH: 1333
<212> TYPE: DNA
<213> ORGANISM: Homo sapiens
<220> FEATURE:
<221> NAME/KEY: CDS
<222> LOCATION: (2)..(1333)

<400> SEQUENCE: 13 g acg gca tta gcc aaa gaa cta aga gaa ctc cgg att gaa gaa aca aac    49
  Thr Ala Leu Ala Lys Glu Leu Arg Glu Leu Arg Ile Glu Glu Thr Asn
    1               5                  10                  15 cgc cca atg aag aag gtg act gat tac tcc tcc tcc agt gag gag tca      97
Arg Pro Met Lys Lys Val Thr Asp Tyr Ser Ser Ser Ser Glu Glu Ser
             20                  25                  30 gaa agt agc gag gaa gag gag gaa gat gga gag agc gag acc cat gat      145
Glu Ser Ser Glu Glu Glu Glu Asp Gly Glu Ser Glu Thr His Asp
         35                  40                  45 ggg aca gtg gct gtc agc gac ata ccc aga ctg ata cca aca gga gct      193
Gly Thr Val Ala Val Ser Asp Ile Pro Arg Leu Ile Pro Thr Gly Ala
 50                  55                  60 cca ggc agc aac gag cag tac aat gtg gga atg gtg ggg acg cat ggg      241
Pro Gly Ser Asn Glu Gln Tyr Asn Val Gly Met Val Gly Thr His Gly
 65                  70                  75                  80 ctg gag acc tct cat gcg gac agt ttc agc ggc agt att tca aga gaa      289
Leu Glu Thr Ser His Ala Asp Ser Phe Ser Gly Ser Ile Ser Arg Glu
                 85                  90                  95 gga acc ttg atg att aga gag acg tct gga gag aag aag cga tct ggc      337
Gly Thr Leu Met Ile Arg Glu Thr Ser Gly Glu Lys Lys Arg Ser Gly
            100                 105                 110 cac agt gac agc aat ggc ttt gct ggc cac atc aac ctc cct gac ctg      385
His Ser Asp Ser Asn Gly Phe Ala Gly His Ile Asn Leu Pro Asp Leu
        115                 120                 125 gtg cag cag agc cat tct cca gct gga acc ccg act gag gga ctg ggg      433
Val Gln Gln Ser His Ser Pro Ala Gly Thr Pro Thr Glu Gly Leu Gly
    130                 135                 140 cgc gtc tca acc cat tcc cag gag atg gac tct ggg act gaa tat ggc      481
Arg Val Ser Thr His Ser Gln Glu Met Asp Ser Gly Thr Glu Tyr Gly
145                 150                 155                 160 atg ggg agc agc acc aaa gcc tcc ttc acc ccc ttt gtg gac ccc aga      529
```

```
Met Gly Ser Ser Thr Lys Ala Ser Phe Thr Pro Phe Val Asp Pro Arg
            165                 170                 175 gta tac cag acg tct ccc act gat gaa gat gaa gag gat gag gaa tca      577
Val Tyr Gln Thr Ser Pro Thr Asp Glu Asp Glu Glu Asp Glu Glu Ser
            180                 185                 190 tca gcc gca gct ctg ttt act agc gaa ctt ctt agg caa gaa cag gcc      625
Ser Ala Ala Ala Leu Phe Thr Ser Glu Leu Leu Arg Gln Glu Gln Ala
            195                 200                 205 aaa ctc aat gaa gca aga aag att tcg gtg gta aat gta aac cca acc      673
Lys Leu Asn Glu Ala Arg Lys Ile Ser Val Val Asn Val Asn Pro Thr
        210                 215                 220 aac att cgg cct cat agc gac aca cca gaa atc aga aaa tac aag aaa      721
Asn Ile Arg Pro His Ser Asp Thr Pro Glu Ile Arg Lys Tyr Lys Lys
225                 230                 235                 240 cga ttc aac tca gaa ata ctt tgt gca gct ctg tgg ggt gta aac ctt      769
Arg Phe Asn Ser Glu Ile Leu Cys Ala Ala Leu Trp Gly Val Asn Leu
                245                 250                 255 ctg gtg ggg act gaa aat ggc ctg atg ctt ttg gac cga agt ggg caa      817
Leu Val Gly Thr Glu Asn Gly Leu Met Leu Leu Asp Arg Ser Gly Gln
            260                 265                 270 ggc aaa gtc tat aat ctg atc aac cgg agg cga ttt cag cag atg gat      865
Gly Lys Val Tyr Asn Leu Ile Asn Arg Arg Arg Phe Gln Gln Met Asp
            275                 280                 285 gtg cta gag gga ctg aat gtc ctt gtg aca att tca gga aag aag aat      913
Val Leu Glu Gly Leu Asn Val Leu Val Thr Ile Ser Gly Lys Lys Asn
        290                 295                 300 aag cta cga gtt tac tat ctt tca tgg tta aga aac aga ata cta cat      961
Lys Leu Arg Val Tyr Tyr Leu Ser Trp Leu Arg Asn Arg Ile Leu His
305                 310                 315                 320 aat gac cca gaa gta gaa aag aaa caa ggc tgg atc act gtt ggg gac     1009
Asn Asp Pro Glu Val Glu Lys Lys Gln Gly Trp Ile Thr Val Gly Asp
                325                 330                 335 ttg gaa ggc tgt ata cat tat aaa gtt gtt aaa tat gaa agg atc aaa     1057
Leu Glu Gly Cys Ile His Tyr Lys Val Val Lys Tyr Glu Arg Ile Lys
            340                 345                 350 ttt ttg gtg att gcc tta aag aat gct gtg gaa ata tat gct tgg gct     1105
Phe Leu Val Ile Ala Leu Lys Asn Ala Val Glu Ile Tyr Ala Trp Ala
            355                 360                 365 cct aaa ccg tat cat aaa ttc atg gca ttt aag tct ttt gca gat ctc     1153
Pro Lys Pro Tyr His Lys Phe Met Ala Phe Lys Ser Phe Ala Asp Leu
        370                 375                 380 cag cac aag cct ctg cta gtt gat ctc acg gta gaa gaa ggt caa aga     1201
Gln His Lys Pro Leu Leu Val Asp Leu Thr Val Glu Glu Gly Gln Arg
385                 390                 395                 400 tta aag gtt att ttt ggt tca cac act ggt ttc cat gta att gat gtt     1249
Leu Lys Val Ile Phe Gly Ser His Thr Gly Phe His Val Ile Asp Val
                405                 410                 415 gat tca gga aac tct tat gat atc tac ata cca tct cat att cag ggc     1297
Asp Ser Gly Asn Ser Tyr Asp Ile Tyr Ile Pro Ser His Ile Gln Gly
            420                 425                 430 aat atc act cct cat gct att gtc atc ttg cct aaa                     1333
Asn Ile Thr Pro His Ala Ile Val Ile Leu Pro Lys
            435                 440

<210> SEQ ID NO 14
<211> LENGTH: 444
<212> TYPE: PRT
<213> ORGANISM: Homo sapiens

<400> SEQUENCE: 14
```

-continued

```
Thr Ala Leu Ala Lys Glu Leu Arg Glu Leu Arg Ile Glu Glu Thr Asn
 1               5                  10                 15

Arg Pro Met Lys Lys Val Thr Asp Tyr Ser Ser Ser Glu Glu Ser
            20                  25                  30

Glu Ser Ser Glu Glu Glu Glu Asp Gly Glu Ser Glu Thr His Asp
         35                  40                  45

Gly Thr Val Ala Val Ser Asp Ile Pro Arg Leu Ile Pro Thr Gly Ala
     50                  55                  60

Pro Gly Ser Asn Glu Gln Tyr Asn Val Gly Met Val Gly Thr His Gly
 65                  70                  75                  80

Leu Glu Thr Ser His Ala Asp Ser Phe Ser Gly Ser Ile Ser Arg Glu
                 85                  90                  95

Gly Thr Leu Met Ile Arg Glu Thr Ser Gly Glu Lys Lys Arg Ser Gly
                100                 105                 110

His Ser Asp Ser Asn Gly Phe Ala Gly His Ile Asn Leu Pro Asp Leu
            115                 120                 125

Val Gln Gln Ser His Ser Pro Ala Gly Thr Pro Thr Glu Gly Leu Gly
130                 135                 140

Arg Val Ser Thr His Ser Gln Glu Met Asp Ser Gly Thr Glu Tyr Gly
145                 150                 155                 160

Met Gly Ser Ser Thr Lys Ala Ser Phe Thr Pro Phe Val Asp Pro Arg
                165                 170                 175

Val Tyr Gln Thr Ser Pro Thr Asp Glu Asp Glu Glu Asp Glu Glu Ser
            180                 185                 190

Ser Ala Ala Ala Leu Phe Thr Ser Glu Leu Leu Arg Gln Glu Gln Ala
            195                 200                 205

Lys Leu Asn Glu Ala Arg Lys Ile Ser Val Val Asn Val Asn Pro Thr
210                 215                 220

Asn Ile Arg Pro His Ser Asp Thr Pro Glu Ile Arg Lys Tyr Lys Lys
225                 230                 235                 240

Arg Phe Asn Ser Glu Ile Leu Cys Ala Ala Leu Trp Gly Val Asn Leu
            245                 250                 255

Leu Val Gly Thr Glu Asn Gly Leu Met Leu Leu Asp Arg Ser Gly Gln
            260                 265                 270

Gly Lys Val Tyr Asn Leu Ile Asn Arg Arg Arg Phe Gln Gln Met Asp
        275                 280                 285

Val Leu Glu Gly Leu Asn Val Leu Val Thr Ile Ser Gly Lys Lys Asn
290                 295                 300

Lys Leu Arg Val Tyr Tyr Leu Ser Trp Leu Arg Asn Arg Ile Leu His
305                 310                 315                 320

Asn Asp Pro Glu Val Glu Lys Lys Gln Gly Trp Ile Thr Val Gly Asp
                325                 330                 335

Leu Glu Gly Cys Ile His Tyr Lys Val Val Lys Tyr Glu Arg Ile Lys
            340                 345                 350

Phe Leu Val Ile Ala Leu Lys Asn Ala Val Glu Ile Tyr Ala Trp Ala
            355                 360                 365

Pro Lys Pro Tyr His Lys Phe Met Ala Phe Lys Ser Phe Ala Asp Leu
370                 375                 380

Gln His Lys Pro Leu Leu Val Asp Leu Thr Val Glu Glu Gly Gln Arg
385                 390                 395                 400

Leu Lys Val Ile Phe Gly Ser His Thr Gly Phe His Val Ile Asp Val
                405                 410                 415

Asp Ser Gly Asn Ser Tyr Asp Ile Tyr Ile Pro Ser His Ile Gln Gly
```

```
                      420                 425                 430
Asn Ile Thr Pro His Ala Ile Val Ile Leu Pro Lys
            435                 440

<210> SEQ ID NO 15
<211> LENGTH: 1332
<212> TYPE: DNA
<213> ORGANISM: Homo sapiens
<220> FEATURE:
<221> NAME/KEY: CDS
<222> LOCATION: (1)..(1332)

<400> SEQUENCE: 15 acg gca tta gcc aaa gaa cta aga gaa ctc cgg att gaa gaa aca aac        48
Thr Ala Leu Ala Lys Glu Leu Arg Glu Leu Arg Ile Glu Glu Thr Asn
  1               5                  10                  15 cgc cca atg aag aag gtg act gat tac tcc tcc tcc agt gag gag tca        96
Arg Pro Met Lys Lys Val Thr Asp Tyr Ser Ser Ser Ser Glu Glu Ser
             20                  25                  30 gaa agt agc gag gaa gag gag gaa gat gga gag agc gag acc cat gat       144
Glu Ser Ser Glu Glu Glu Glu Glu Asp Gly Glu Ser Glu Thr His Asp
         35                  40                  45 ggg aca gtg gct gtc agc gac ata ccc aga ctg ata cca aca gga gct       192
Gly Thr Val Ala Val Ser Asp Ile Pro Arg Leu Ile Pro Thr Gly Ala
     50                  55                  60 cca ggc agc aac gag cag tac aat gtg gga atg gtg ggg acg cat ggg       240
Pro Gly Ser Asn Glu Gln Tyr Asn Val Gly Met Val Gly Thr His Gly
 65                  70                  75                  80 ctg gag acc tct cat gcg gac agt ttc agc ggc agt att tca aga gaa       288
Leu Glu Thr Ser His Ala Asp Ser Phe Ser Gly Ser Ile Ser Arg Glu
                 85                  90                  95 gga acc ttg atg att aga gag acg tct gga gag aag aag cga tct ggc       336
Gly Thr Leu Met Ile Arg Glu Thr Ser Gly Glu Lys Lys Arg Ser Gly
            100                 105                 110 cac agt gac agc aat ggc ttt gct ggc cac atc aac ctc cct gac ctg       384
His Ser Asp Ser Asn Gly Phe Ala Gly His Ile Asn Leu Pro Asp Leu
        115                 120                 125 gtg cag cag agc cat tct cca gct gga acc ccg act gag gga ctg ggg       432
Val Gln Gln Ser His Ser Pro Ala Gly Thr Pro Thr Glu Gly Leu Gly
    130                 135                 140 cgc gtc tca acc cat tcc cag gag atg gac tct ggg act gaa tat ggc       480
Arg Val Ser Thr His Ser Gln Glu Met Asp Ser Gly Thr Glu Tyr Gly
145                 150                 155                 160 atg ggg agc agc acc aaa gcc tcc ttc acc ccc ttt gtg gac ccc aga       528
Met Gly Ser Ser Thr Lys Ala Ser Phe Thr Pro Phe Val Asp Pro Arg
                165                 170                 175 gta tac cag acg tct ccc act gat gaa gat gaa gag gat gag gaa tca       576
Val Tyr Gln Thr Ser Pro Thr Asp Glu Asp Glu Glu Asp Glu Glu Ser
            180                 185                 190 tca gcc gca gct ctg ttt act agc gaa ctt ctt agg caa gaa cag gcc       624
Ser Ala Ala Ala Leu Phe Thr Ser Glu Leu Leu Arg Gln Glu Gln Ala
        195                 200                 205 aaa ctc aat gaa gca aga aag att tcg gtg gta aat gta aac cca acc       672
Lys Leu Asn Glu Ala Arg Lys Ile Ser Val Val Asn Val Asn Pro Thr
    210                 215                 220 aac att cgg cct cat agc gac aca cca gaa atc aga aaa tac aag aaa       720
Asn Ile Arg Pro His Ser Asp Thr Pro Glu Ile Arg Lys Tyr Lys Lys
225                 230                 235                 240 cga ttc aac tca gaa ata ctt tgt gca gct ctg tgg ggt gta aac ctt       768
Arg Phe Asn Ser Glu Ile Leu Cys Ala Ala Leu Trp Gly Val Asn Leu
                245                 250                 255
```

-continued

```
ctg gtg ggg act gaa aat ggc ctg atg ctt ttg gac cga agt ggg caa       816
Leu Val Gly Thr Glu Asn Gly Leu Met Leu Leu Asp Arg Ser Gly Gln
            260                 265                 270 ggc aaa gtc tat aat ctg atc aac cgg agg cga ttt cag cag atg gat       864
Gly Lys Val Tyr Asn Leu Ile Asn Arg Arg Arg Phe Gln Gln Met Asp
        275                 280                 285 gtg cta gag gga ctg aat gtc ctt gtg aca att tca gga aag aag aat       912
Val Leu Glu Gly Leu Asn Val Leu Val Thr Ile Ser Gly Lys Lys Asn
    290                 295                 300 aag cta cga gtt tac tat ctt tca tgg tta aga aac aga ata cta cat       960
Lys Leu Arg Val Tyr Tyr Leu Ser Trp Leu Arg Asn Arg Ile Leu His
305                 310                 315                 320 aat gac cca gaa gta gaa aag aaa caa ggc tgg atc act gtt ggg gac      1008
Asn Asp Pro Glu Val Glu Lys Lys Gln Gly Trp Ile Thr Val Gly Asp
                325                 330                 335 ttg gaa ggc tgt ata cat tat aaa gtt gtt aaa tat gaa agg atc aaa      1056
Leu Glu Gly Cys Ile His Tyr Lys Val Val Lys Tyr Glu Arg Ile Lys
            340                 345                 350 ttt ttg gtg att gcc tta aag aat gct gtg gaa ata tat gct tgg gct      1104
Phe Leu Val Ile Ala Leu Lys Asn Ala Val Glu Ile Tyr Ala Trp Ala
        355                 360                 365 cct aaa ccg tat cat aaa ttc atg gca ttt aag tct ttt gca gat ctc      1152
Pro Lys Pro Tyr His Lys Phe Met Ala Phe Lys Ser Phe Ala Asp Leu
    370                 375                 380 cag cac aag cct ctg cta gtt gat ctc acg gta gaa gaa ggt caa aga      1200
Gln His Lys Pro Leu Leu Val Asp Leu Thr Val Glu Glu Gly Gln Arg
385                 390                 395                 400 tta aag gtt att ttt ggt tca cac act ggt ttc cat gta att gat gtt      1248
Leu Lys Val Ile Phe Gly Ser His Thr Gly Phe His Val Ile Asp Val
                405                 410                 415 gat tca gga aac tct tat gat atc tac ata cca tct cat att cag ggc      1296
Asp Ser Gly Asn Ser Tyr Asp Ile Tyr Ile Pro Ser His Ile Gln Gly
            420                 425                 430 aat atc act cct cat gct att gtc atc ttg cct aaa                      1332
Asn Ile Thr Pro His Ala Ile Val Ile Leu Pro Lys
        435                 440
```

CSAPK-1 PROTEIN AND USES THEREFOR

RELATED APPLICATIONS

This application is a divisional application of Ser. No. 09/163,115 filed on Sep. 29, 1998, pending incorporated herein by reference which claims priority to U.S. provisional Application No. 60/099,657, filed on Sep. 9, 1998, incorporated herein in its entirety by this reference.

BACKGROUND OF THE INVENTION

Phosphate tightly associated with protein has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated proteins implies the existence of one or more protein kinases capable of phosphorylating amino acid residues on proteins, and also of protein phosphatases capable of hydrolyzing phosphorylated amino acid residues on proteins.

Protein kinases play critical roles in the regulation of biochemical and morphological changes associated with cellular growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721). Protein kinases can be divided into two main groups based on either amino acid sequence similarity or specificity for either serine/threonine or tyrosine residues. A small number of dual-specificity kinases are structurally like the serine/threonine-specific group. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) *Science* 241: 42–52).

SUMMARY OF THE INVENTION

The present invention is based, at least in part, on the discovery of novel nucleic acid molecules and proteins encoded by such nucleic acid molecules, referred to herein as "Cardiovascular System Associated Protein Kinase" ("CSAPK") proteins. The CSAPK nucleic acid and protein molecules of the present invention are useful as modulating agents in regulating a variety of cellular processes, e.g., cardiac cellular processes. Accordingly, in one aspect, this invention provides isolated nucleic acid molecules encoding CSAPK proteins or biologically active portions thereof, as well as nucleic acid fragments suitable as primers or hybridization probes for the detection of CSAPK-encoding nucleic acids.

In one embodiment, a CSAPK nucleic acid molecule of the invention is at least 60%, 62%, 65%, 70%, 75%, 80%, 85%, 90%, 95%, 98% or more homologous to a nucleotide sequence (e.g., to the entire length of the nucleotide sequence) including SEQ ID NO:1, SEQ ID NO:3, or a complement thereof. In another embodiment, a CSAPK nucleic acid molecule is 50%, 54%, 55%, 60%, 65%, 70%, 75%, 80%, 85%, 86%, 90%, 95%, 98% homologous to a nucleotide sequence including SEQ ID NO:4, SEQ ID NO:6, or a complement thereof. In yet another embodiment, a CSAPK nucleic acid molecule is 60%, 65%, 70%, 75%, 80%, 85%, 90%, 95%, 97%, 98% homologous to a nucleotide sequence including SEQ ID NO:7, SEQ ID NO:9, or a complement thereof. In yet another embodiment, a CSAPK nucleic acid molecule is 60%, 65%, 70%, 73%, 75%, 80%, 85%, 86%, 90%, 95%, 98% homologous to a nucleotide sequence including SEQ ID NO:10, SEQ ID NO:12, or a complement thereof. In a further embodiment, a CSAPK nucleic acid molecule is 60%, 65%, 70%, 75%, 78%, 80%, 85%, 90%, 95%, 98% homologous to a nucleotide sequence including SEQ ID NO:13, SEQ ID NO:15, or a complement thereof.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1–296 of SEQ ID NO:1. In yet another embodiment, the nucleic acid molecule includes SEQ ID NO:3 and nucleotides 1202–4137 of SEQ ID NO:1. In another preferred embodiment, the nucleic acid molecule has the nucleotide sequence shown in SEQ ID NO:1 or 3. In another preferred embodiment, the nucleic acid molecule comprises a fragment of at least 509 nucleotides of the nucleotide sequence of SEQ ID NO:1, SEQ ID NO:3, or a complement thereof.

In another preferred embodiment, the isolated nucleic acid molecule includes the nucleotide sequence shown SEQ ID NO:4 or 6, or a complement thereof. In another embodiment, the nucleic acid molecule includes SEQ ID NO:6 and nucleotides 1–46 of SEQ ID NO:4. In yet another embodiment, the nucleic acid molecule includes SEQ ID NO:6 and nucleotides 1411–2120 of SEQ ID NO:4. In another preferred embodiment, the nucleic acid molecule has the nucleotide sequence shown in SEQ ID NO:4 or 6.

In another preferred embodiment, the isolated nucleic acid molecule includes the nucleotide sequence shown SEQ ID NO:7 or 9, or a complement thereof. In another embodiment, the nucleic acid molecule includes SEQ ID NO:9 and nucleotides 1–50 of SEQ ID NO:7. In yet another embodiment, the nucleic acid molecule includes SEQ ID NO:9 and nucleotides 1793–2454 of SEQ ID NO:7. In another preferred embodiment, the nucleic acid molecule has the nucleotide sequence shown in SEQ ID NO:7 or 9.

In another preferred embodiment, the isolated nucleic acid molecule includes the nucleotide sequence shown SEQ ID NO:10 or 12, or a complement thereof. In another embodiment, the nucleic acid molecule includes SEQ ID NO:12 and nucleotides 1–274 of SEQ ID NO:10. In yet another embodiment, the nucleic acid molecule includes SEQ ID NO:12 and nucleotides 755–1864of SEQ ID NO:10. In another preferred embodiment, the nucleic acid molecule has the nucleotide sequence shown in SEQ ID NO:10 or 12.

In another preferred embodiment, the isolated nucleic acid molecule includes the nucleotide sequence shown in SEQ ID NO:13 or 15, or a complement thereof. In yet another preferred embodiment, the nucleic acid molecule has the nucleotide sequence shown in SEQ ID NO:13 or 15.

In another embodiment, a CSAPK nucleic acid molecule includes a nucleotide sequence encoding a protein having an amino acid sequence sufficiently homologous to the amino acid sequence of SEQ ID NO:2, SEQ ID NO:5, SEQ ID 8, SEQ ID NO:11, or SEQ ID NO:14. In a preferred embodiment, a CSAPK nucleic acid molecule includes a nucleotide sequence encoding a protein having an amino acid sequence at least 50%, 55%, 60%, 65%, 70%, 75%, 80%, 81%, 85%, 90%, 95%, 98% or more homologous to an a acid sequence including SEQ ID NO:2 (e.g., the entire amino acid sequence of SEQ ID NO:2). In another preferred embodiment, a CSAPK nucleic acid molecule includes a nucleotide sequence encoding a protein having an amino acid sequence at least 42%, 45%, 50%, 55%, 60%, 65%, 70%, 75%, 80%, 85%, 90%, 95%, 98% or more homologous amino acid sequence including SEQ ID NO:5 (e.g., the entire amino acid sequence of SEQ ID NO:5). In yet another preferred embodiment, a CSAPK nucleic acid molecule includes a nucleotide sequence encoding a protein having an amino acid sequence at least 41%, 45%, 50%, 55%, 60%, 65%, 70%, 75%, 80%, 85%, 90%,95%,98% or more homologous to an amino acid sequence including SEQ ID NO:8 (e.g., the entire amino acid sequence of SEQ ID NO:8). In a further preferred embodiment, a CSAPK nucleic acid molecule includes a nucleotide sequence encoding a protein having an amino acid sequence at least 59%, 60%, 65%, 70%, 75%, 80%, 85%, 90%, 95%, 98% or more homologous to an aminoacid sequence including SEQ ID NO:11 (e.g., the entire amino acid sequence of SEQ ID NO:11). In another preferred embodiment, a CSAPK nucleic acid molecule includes a nucleotide sequence encoding a protein having an amino acid sequence at least 60%, 65%, 70%, 75%, 80%, 85%, 90%, 95%, 98% or more homologous to an amino acid sequence including SEQ ID NO:14 (e.g., the entire amino acid sequence of SEQ ID NO:14).

In another preferred embodiment, an isolated nucleic acid molecule encodes the amino acid sequence of a human CSAPK. In yet another preferred embodiment, the nucleic acid molecule includes a nucleotide sequence encoding a protein which includes the amino acid sequence of SEQ ID NO:2, SEQ ID NO:5, SEQ ID 8, SEQ ID NO:11, or SEQ ID NO:14. In yet another preferred embodiment, the nucleic acid molecule includes a nucleotide sequence encoding a protein having the amino acid sequence of SEQ ID NO:2, SEQ ID NO:5, SEQ ID 8, SEQ ID NO:11, or SEQ ID NO:14.

Another embodiment of the invention features nucleic acid molecules, preferably CSAPK nucleic acid molecules, which specifically detect CSAPK nucleic acid molecules relative to nucleic acid molecules encoding non-CSAPK proteins. For example, in one embodiment, such a nucleic acid molecule is at least 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO:1, SEQ ID NO:4, SEQ ID 7, SEQ ID NO:10, SEQ ID NO:13, or a complement thereof.

In other preferred embodiments, the nucleic acid molecule encodes a naturally occurring allelic variant of a polypeptide which includes the amino acid sequence of SEQ ID NO:2, wherein the nucleic acid molecule hybridizes to a nucleic acid molecule which includes SEQ ID NO:1 or SEQ ID NO:3 under stringent conditions. In other preferred embodiments, the nucleic acid molecule encodes a naturally occurring allelic variant of a polypeptide which includes the amino acid sequence of SEQ ID NO:5, wherein the nucleic acid molecule hybridizes to a nucleic acid molecule which includes SEQ ID NO:4 or SEQ ID NO:6 under stringent conditions. In other preferred embodiments, the nucleic acid molecule encodes a naturally occurring allelic variant of a polypeptide which includes the amino acid sequence of SEQ ID NO:8, wherein the nucleic acid molecule hybridizes to a nucleic acid molecule which includes SEQ ID NO:7 or SEQ ID NO:9 under stringent conditions. In other preferred embodiments, the nucleic acid molecule encodes a naturally occurring allelic variant of a polypeptide which includes the amino acid sequence of SEQ ID NO:11, wherein the nucleic acid molecule hybridizes to a nucleic acid molecule which includes SEQ ID NO:10 or SEQ ID NO:12 under stringent conditions. In other preferred embodiments, the nucleic acid molecule encodes a naturally occurring allelic variant of a polypeptide which includes the amino acid sequence of SEQ ID NO:14, wherein the nucleic acid molecule hybridizes to a nucleic acid molecule which includes SEQ ID NO:13 or SEQ ID NO:15 under stringent conditions.

Another embodiment of the invention provides an isolated nucleic acid molecule which is antisense to a CSAPK nucleic acid molecule, e.g., the coding strand of a CSAPK nucleic acid molecule.

Another aspect of the invention provides a vector comprising a CSAPK nucleic acid molecule. In certain embodiments, the vector is a recombinant expression vector. In another embodiment, the invention provides a host cell containing a vector of the invention. The invention also provides a method for producing a protein, preferably a CSAPK protein, by culturing in a suitable medium, a host cell, e.g., a mammalian host cell such as a non-human mammalian cell, of the invention containing a recombinant expression vector, such that the protein is produced.

Another aspect of this invention features isolated or recombinant CSAPK proteins and polypeptides. In one embodiment, the isolated protein, preferably a CSAPK-1 protein, includes at least one Ser/Thr kinase domain, and at least one ATP-binding site. In another embodiment, the isolated protein, preferably a CSAPK-1 protein, includes at least one Ser/Thr kinase domain, and at least one ATP-binding site and has an amino acid sequence which is at least 51%, 55%, 60%, 65%, 70%, 75%, 80%, 81%, 85%, 90%, 95%, 99% or more homologous to an amino acid sequence including SEQ ID NO:2. In yet another embodiment, the isolated protein, preferably a CSAPK-1 protein, includes at least one Ser/Thr kinase domain, and at least one ATP-binding site and is expressed and/or functions in cells of the cardiovascular system. In an even further embodiment, the isolated protein, preferably a CSAPK-1 protein, includes at least one Ser/Thr kinase domain, and at least one ATP-binding site and plays a role in signalling pathways associated with cellular growth, e.g., signalling pathways associated with cell cycle regulation. In another embodiment, the isolated protein, preferably a CSAPK-1 protein, includes at least one Ser/Thr kinase domain, and at least one ATP-binding site and is encoded by a nucleic acid molecule having a nucleotide sequence which hybridizes under stringent hybridization conditions to a nucleic acid molecule comprising the nucleotide sequence of SEQ ID NO:1 or SEQ ID NO:3.

In another embodiment, the isolated protein, preferably a CSAPK-2 protein, includes at least one dual specificity kinase catalytic domain and at least one ATP-binding site. In another embodiment, the isolated protein, preferably a CSAPK-2 protein, includes at least one dual specificity kinase catalytic domain, at least one leucine zipper- basic region, and at least one ATP-binding site. In another embodiment, the isolated protein, preferably a CSAPK-2 protein, includes at least one dual specificity kinase catalytic domain and at least one ATP-binding site and has an amino acid sequence which is at least 42%, 45%, 50%, 55%, 60%, 65%, 70%, 75%, 80%, 85%, 90%, 95%, 98%, more homologous to an amino acid sequence including SEQ ID NO:5. In yet another embodiment, the isolated protein, preferably a CSAPK-2 protein, includes at least one dual specificity kinase catalytic domain, and at least one ATP-binding site and is expressed and/or functions in cells of the cardiovascular system. In an even further embodiment, the isolated protein, preferably a CSAPK-2 protein, includes at least one dual specificity kinase catalytic domain, and at least one ATP-binding site and plays a role in signalling pathways associated with cellular growth, e.g., signalling pathways associated with cell cycle regulation. In another embodiment, the isolated protein, preferably a CSAPK-2 protein, includes at least one dual specificity kinase catalytic domain, and at least one ATP-binding site and is encoded by a nucleic acid molecule having a nucleotide sequence which hybridizes under stringent hybridization conditions to a nucleic acid molecule comprising the nucleotide sequence of SEQ ID NO:4 or SEQ ID NO:6.

In yet another embodiment, the isolated protein, preferably a CSAPK-3 protein, includes at least one Ser/Thr kinase domain, and at least one ATP-binding site. In another embodiment, the isolated protein, preferably a CSAPK-3 protein, includes at least one Ser/Thr kinase domain, and at least one ATP-binding site and has an amino acid sequence which is at least 41%, 45%, 50%, 55%, 60%, 65%, 70%, 75%, 80%, 85%, 90%, 95%, 98% or more homologous to an amino acid sequence including SEQ ID NO:8. In yet another embodiment, the isolated protein, preferably a CSAPK-3 protein, includes at least one Ser/Thr kinase domain, and at least one ATP-binding site and is expressed and/or functions in cells of the cardiovascular system. In an even further embodiment, the isolated protein, preferably a CSAPK-3 protein, includes at least one Ser/Thr kinase domain, and at least one ATP-binding site and plays a role in signalling pathways associated with cellular growth, e.g., signalling pathways associated with cell cycle regulation. In another embodiment, the isolated protein, preferably a CSAPK-3 protein, includes at least one Ser/Thr kinase domain, and at least one ATP-binding site and is encoded by a nucleic acid molecule having a nucleotide sequence which hybridizes under stringent hybridization conditions to a nucleic acid molecule comprising the nucleotide sequence of SEQ ID NO:7 or SEQ ID NO:9.

In another embodiment, the isolated protein, preferably a CSAPK-4 protein, includes at least one Ser/Thr kinase domain, and at least one ATP-binding site. In another embodiment, the isolated protein, preferably a CSAPK-4 protein, includes at least one Ser/Thr kinase domain, and at least one ATP-binding site and has an amino acid sequence which is at least 59%, 60%, 65%, 70%, 75%, 80%, 85%, 90%, 95%, 98% or more homologous to an amino acid sequence including SEQ ID NO:11. In yet another embodiment, the isolated protein, preferably a CSAPK-4 protein, includes at least one Ser/Thr kinase domain, and at least one ATP-binding site and is expressed and/or functions in cells of the cardiovascular system. In an even further embodiment, the isolated protein, preferably a CSAPK-4 protein, includes at least one Ser/Thr kinase domain, and at least one ATP-binding site and plays a role in signalling pathways associated with cellular growth, e.g., signalling pathways associated with cell cycle regulation. In another embodiment, the isolated protein, preferably a CSAPK-4 protein, includes at least one Ser/Thr kinase domain, and at least one ATP-binding site and is encoded by a nucleic acid molecule having a nucleotide sequence which hybridizes under stringent hybridization conditions to a nucleic acid molecule comprising the nucleotide sequence of SEQ ID NO:10 or SEQ ID NO:12.

In another embodiment, the isolated protein, preferably a human CSAPK-5 protein, includes at least one Ser/Thr kinase domain, and at least one ATP-binding site. In yet another embodiment, the isolated protein, preferably a human CSAPK-5 protein, includes at least one Ser/Thr kinase domain, and at least one ATP-binding site and has an amino acid sequence which is at least 60%, 65%, 70%, 75%, 80%, 85%, 90%, 95%, 98% or more homologous to an amino acid sequence including SEQ ID NO:14. In yet another embodiment, the isolated protein, preferably a human CSAPK-5 protein, includes at least one Ser/Thr kinase domain, and at least one ATP-binding site and is expressed and/or functions in cells of the cardiovascular system. In an even further embodiment, the isolated protein, preferably a human CSAPK-5 protein, includes at least one Ser/Thr kinase domain, and at least one ATP-binding site and plays a role in signalling pathways associated with cellular growth, e.g., signalling pathways associated with cell cycle regulation. In another embodiment, the isolated protein, preferably a human CSAPK-5 protein, includes at least one Ser/Thr kinase domain, and at least one ATP-binding site and is able to interact with Nck (described in Lehman et al. (1990) Nucleic Acids Res. 18:1048). In another embodiment, the isolated protein, preferably a human CSAPK-5 protein, includes at least one Ser/Thr kinase domain, and at least one ATP-binding site and is encoded by a nucleic acid molecule having a nucleotide sequence which hybridizes under stringent hybridization conditions to a nucleic acid molecule comprising the nucleotide sequence of SEQ ID NO:13 or SEQ ID NO:15.

In another embodiment, the isolated protein, preferably a CSAPK protein, has an amino acid sequence sufficiently homologous to the amino acid sequence of SEQ ID NO:2, SEQ ID NO:5, SEQ ID 8, SEQ ID NO:11, or SEQ ID NO:14. In a preferred embodiment, the protein, preferably a CSAPK protein, has an amino acid sequence at least about 41%,42%,45%, 50%, 55%, 59%, 60%, 65%, 70%, 75%, 80%, 81%, 85%, 90%, 95%, 98% or more homologous to an amino acid sequence including SEQ ID NO:2, SEQ ID NO:5, SEQ ID 8, SEQ ID NO:11, or SEQ ID NO:14 (e.g., the entire amino acid sequence of SEQ ID NO:2, SEQ ID NO:5, SEQ ID 8, SEQ ID NO:11, or SEQ ID NO:14). In another embodiment, the invention features fragments of the proteins having the amino acid sequence of SEQ ID NO:2, SEQ ID NO:5, SEQ ID 8, SEQ ID NO:11, or SEQ ID NO: 14, wherein the fragment comprises at least 15 amino acids (e.g., contiguous amino acids) of the amino acid sequence of SEQ ID NO:2, SEQ ID NO:5, SEQ ID 8, SEQ ID NO:11, or SEQ ID NO:14, respectively. In another embodiment, the protein, preferably a CSAPK protein, has the amino acid sequence of SEQ ID NO:2, SEQ ID NO:5, SEQ ID 8, SEQ ID NO:11, or SEQ ID NO:14.

Another embodiment of the invention features an isolated protein, preferably a CSAPK protein, which is encoded by a nucleic acid molecule having a nucleotide sequence at least about 50%, 54%, 55%, 60%, 62%, 65%, 70%, 75%, 78%, 80%, 85%, 86%, 90%, 95%, 97%, 98% or more homologous to a nucleotide sequence (e.g., to the entire length of the nucleotide sequence) including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, or a complement thereof. This invention further features an isolated protein, preferably a CSAPK protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, or a complement thereof.

The proteins of the present invention or biologically active portions thereof, can be operatively linked to a non-CSAPK polypeptide (e.g., heterologous amino acid sequences) to form fusion proteins. The invention further features antibodies, such as monoclonal or polyclonal antibodies, that specifically bind proteins of the invention, preferably CSAPK proteins. In addition, the CSAPK proteins or biologically active portions thereof can be incorporated into pharmaceutical compositions, which optionally include pharmaceutically acceptable carriers.

In another aspect, the present invention provides a method for detecting the presence of a CSAPK nucleic acid molecule, protein or polypeptide in a biological sample by contacting the biological sample with an agent capable of detecting a CSAPK nucleic acid molecule, protein or polypeptide such that the presence of a CSAPK nucleic acid molecule, protein or polypeptide is detected in the biological sample.

In another aspect, the present invention provides a method for detecting the presence of CSAPK activity in a biological sample by contacting the biological sample with an agent capable of detecting an indicator of CSAPK activity such that the presence of CSAPK activity is detected in the biological sample.

In another aspect, the invention provides a method for modulating CSAPK activity comprising contacting a cell capable of expressing CSAPK with an agent that modulates CSAPK activity such that CSAPK activity in the cell is modulated. In one embodiment, the agent inhibits CSAPK activity. In another embodiment, the agent stimulates CSAPK activity. In one embodiment, the agent is an antibody that specifically binds to a CSAPK protein. In another embodiment, the agent modulates expression of CSAPK by modulating transcription of a CSAPK gene or translation of a CSAPK mRNA. In yet another embodiment, the agent is a nucleic acid molecule having a nucleotide sequence that is antisense to the coding strand of a CSAPK mRNA or a CSAPK gene.

In one embodiment, the methods of the present invention are used to treat a subject having a disorder characterized by aberrant CSAPK protein or nucleic acid expression or activity by administering an agent which is a CSAPK modulator to the subject. In one embodiment, the CSAPK modulator is a CSAPK protein. In another embodiment the CSAPK modulator is a CSAPK nucleic acid molecule. In yet another embodiment, the CSAPK modulator is a peptide, peptidomimetic, or other small molecule. In a preferred embodiment, the disorder characterized by aberrant CSAPK protein or nucleic acid expression is a cellular growth related disorder, e.g., a cardiovascular disorder.

The present invention also provides a diagnostic assay for identifying the presence or absence of a genetic alteration characterized by at least one of (i) aberrant modification or mutation of a gene encoding a CSAPK protein; (ii) misregulation of the gene; and (iii) aberrant post-translational modification of a CSAPK protein, wherein a wild-type form of the gene encodes a protein with a CSAPK activity.

In another aspect the invention provides a method for identifying a compound that binds to or modulates the activity of a CSAPK protein, by providing an indicator composition comprising a CSAPK protein having CSAPK activity, contacting the indicator composition with a test compound, and determining the effect of the test compound on CSAPK activity in the indicator composition to identify a compound that modulates the activity of a CSAPK protein.

Other features and advantages of the invention will be apparent from the following detailed description and claims.

BRIEF DESCRIPTION OF THE DRAWINGS

FIG. 1 depicts the cDNA sequence and predicted amino acid sequence of human CSAPK-1. The nucleotide sequence corresponds to nucleic acids 1 to 4137 of SEQ ID NO:1. The amino acid sequence corresponds to amino acids 1 to 302 of SEQ ID NO:2. The coding region without the 5' and 3' untranslated regions of the human CSAPK-1 gene is shown in SEQ ID NO:3.

FIG. 2 depicts the cDNA sequence and predicted amino acid sequence of human CSAPK-2. The nucleotide sequence corresponds to nucleic acids 1 to 2120 of SEQ ID NO:4. The amino acid sequence corresponds to amino acids 1 to 455 of SEQ ID NO:5. The coding region without the 5' and 3' untranslated regions of the human CSAPK-2 gene is shown in SEQ ID NO:6.

FIG. 3 depicts the cDNA sequence and predicted amino acid sequence of human CSAPK-3. The nucleotide sequence corresponds to nucleic acids 1 to 2454 of SEQ ID NO:7. The amino acid sequence corresponds to amino acids 1 to 581 of SEQ ID NO:8. The coding region without the 5' and 3' untranslated regions of the human CSAPK-3 gene is shown in SEQ ID NO:9.

FIG. 4 depicts the cDNA sequence and predicted amino acid sequence of human CSAPK-4. The nucleotide sequence corresponds to nucleic acids 1 to 1864 of SEQ ID NO:10. The amino acid sequence corresponds to amino acids 1 to 160 of SEQ ID NO:11. The coding region without the 5' and 3' untranslated regions of the human CSAPK-4 gene is shown in SEQ ID NO:12.

FIG. 5 depicts the cDNA sequence and predicted amino acid sequence of human CSAPK-5. The nucleotide sequence corresponds to nucleic acids 1 to 1333 of SEQ ID NO:13. The amino acid sequence corresponds to amino acids 1 to 444 of SEQ ID NO:14. The coding region without the 5' and 3' untranslated regions of the human CSAPK-5 gene is shown in SEQ ID NO:15.

DETAILED DESCRIPTION OF THE INVENTION

The present invention is based, at least in part, on the discovery of novel molecules, referred to herein as "Cardiovascular System Associated Protein Kinase" or "CSAPK" nucleic acid and polypeptide molecules, which play a role in or function in signalling pathways associated with cellular growth. In one embodiment, the CSAPK molecules modulate the activity of one or more proteins involved in cellular growth or differentiation, e.g., cardiac cell growth or differentiation. In another embodiment, the CSAPK molecules of the present invention are capable of modulating the phosphorylation state of a CSAPK molecule or one or more proteins involved in cellular growth or differentiation, e.g., cardiac cell growth or differentiation.

In a preferred embodiment, the CSAPK molecules are protein kinases which are expressed and/or function in cells of the cardiovascular system, e.g., cells of the heart, the blood vessels, and/or the blood.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/theonine and tyrosine residues, e.g., the dual specificity kinases. As referred to herein, protein kinases preferably include a catalytic domain of about 200–400 amino acid residues in length, preferably about 200–300 amino acid residues in length, or more preferably about 250–300 amino acid residues in length, which includes preferably 5–20, more preferably 5–15, or preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42–52) the contents of which are incorporated herein by reference). These subdomains are also described in further detail herein.

Protein kinases play a role in signalling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. Thus, the CSAPK molecules of the present invention may be involved in: 1) the regulation of transmission of signals from cellular receptors, e.g., cardiac cell growth factor receptors; 2) the modulation of the entry of cells, e.g., cardiac precursor cells, into mitosis; 3) the modulation of cellular differentiation; 4) the modulation of cell death; and 5) the regulation of cytoskeleton function, e.g., actin bundling.

Inhibition or over stimulation of the activity of protein kinases involved in signaling pathways associated with cellular growth can lead to perturbed cellular growth, which can in turn lead to cellular growth related disorders. As used herein, a "cellular growth related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., melanoma, prostate cancer, cervical cancer, breast cancer, colon cancer, or sarcoma.

The present invention is based, at least in part, on the discovery of novel molecules, referred to herein as CSAPK protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

One embodiment of the invention features CSAPK nucleic acid molecules, preferably human CSAPK molecules, e.g., CSAPK-1, CSAPK-2, CSAPK-3, CSAPK-4, and CSAPK-5, which were identified from cDNA libraries made from hearts of patients with congestive heart failure (CHF) of ischemic and idiopathic origin. The CSAPK nucleic acid and protein molecules of the invention are described in further detail in the following subsections.

A. The CSAPK-1 Nucleic Acid and Protein Molecules

In one embodiment, the isolated proteins of the present invention, preferably CSAPK-1 proteins, are identified based on the presence of at least one "Ser/Thr kinase site" and at least one "ATP-binding region." As used herein, the term "Ser/Thr kinase site" includes an amino acid sequence of about 200–400 amino acid residues in length, preferably 200–300 amino acid residues in length, and more preferably 250–300 amino acid residues in length, which is conserved in kinases which phosphorylate serine and threonine residues and found in the catalytic domain of Ser/Thr kinases. Preferably, the Ser/Thr kinase site includes the following amino acid consensus sequence $X_{9-g}$-X-G-$X_4$-V-$X_{12}$-K-$X_{(10-19)}$-E-$X_{66}$-h-$X_8$-h-r-D-X-K-$X_2$-N-$X_{17}$-K-$X_2$-D-f-g-$X_{21}$-p-$X_{13}$-w-$X_3$-g-$X_{55}$-R-$X_{14}$-h-$X_3$ (SEQ ID NO:17) (where invariant residues are indicated by upper case letters and nearly invariant residues are indicated by lower case letters). The nearly invariant residues are usually found in most Ser/Thr kinase sites, but can be replaced by other amino acids which, preferably, have similar characteristics. For example, a nearly invariant hydrophobic amino acid in the above amino acid consensus sequence would most likely be replaced by another hydrophobic amino acid. Ser/Thr kinase domains are described in, for example, Levin D. E. et al. (1990) *Proc. Natl. Acad Sci.* USA 87:8272–76, the contents of which are incorporated herein by reference.

As used herein, the term "ATP-binding region" includes an amino acid sequence of about 20–40, preferably 20–30, and more preferably 25–30 amino acid residues in length, present in enzymes which activate their substrates by phosphorylation, and involved in binding adenosine triphosphate (ATP). ATP-binding regions preferably include the following amino acid consensus sequence: G-X-G-X-X-G-X(15–23)-K(SEQ ID NO:18). ATP-binding regions are described in, for example, Samuel K. P. et al. (1987) *FEBS Let.* 218(1): 81–86, the contents of which are incorporated herein by reference. Amino acid residues 40 to 63 of CSAPK-1 comprise an ATP-binding region.

Isolated proteins of the present invention, preferably CSAPK-1 proteins, have an amino acid sequence sufficiently homologous to the amino acid sequence of SEQ ID NO:2 or are encoded by a nucleotide sequence sufficiently homologous to SEQ ID NO:1 or SEQ ID NO:3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein a "CSAPK-1 activity", "biological activity of CSAPK-1" or "functional activity of CSAPK-1" refers to an activity exerted by a CSPAK-1 protein, polypeptide or nucleic acid molecule on a CSPAK-1 responsive cell or a CSAPK-1 protein substrate, as determined in vivo, or in vitro, according to standard techniques. The biological activity of CSAPK-1 is described herein.

Accordingly, another embodiment of the invention features isolated CSAPK-1 proteins and polypeptides having a CSAPK-1 activity. Preferred proteins are CSAPK-1 proteins having at least one Ser/Thr kinase site and at least one ATP-binding region and, preferably, a CSAPK-1 activity. Additional preferred proteins have at least one Ser/Thr kinase site and at least one ATP-binding region and are, preferably, encoded by a nucleic acid molecule having a nucleotide sequence which hybridizes under stringent hybridization conditions to a nucleic acid molecule comprising the nucleotide sequence of SEQ ID NO:1 or SEQ ID NO:3.

The nucleotide sequence of the isolated human CSAPK-1 cDNA and the predicted amino acid sequence of the human CSAPK-1 polypeptide are shown in FIG. 1 and in SEQ ID NOs:1 and 2, respectively. A plasmid containing the nucleotide sequence encoding human CSAPK-1 was deposited with American Type Culture Collection (ATCC), 10801 University Boulevard, Manassas, Va. 20110-2209, on Oct. 27, 1998 and assigned Accession Number 203308. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The CSAPK-1 gene, which is approximately 4137 nucleotides in length, encodes a protein having a molecular weight of approximately 34.7 kD and which is approximately 302 amino acid residues in length. The CSAPK-1 gene is expressed predominantly in heart, skeletal muscle, or the placenta.

B. The CSAPK-2 Nucleic Acid and Protein Molecules

In another embodiment, the isolated proteins of the present invention, preferably CSAPK-2 proteins, are identified based on the presence of at least one dual specificity kinase catalytic domain and at least one ATP-binding region. In yet a further embodiment, the isolated proteins of the present invention, preferably CSAPK-2 proteins, are identified based on the presence of at least one dual specificity kinase catalytic domain, at least one ATP-binding region, and at least one leucine zipper region.

As used herein, the term "dual specificity kinase catalytic domain" includes an amino acid sequence of 200–400 amino acid residues in length, preferably 200–300 amino acid residues in length, and more preferably 250–300 amino acid residues in length, which includes a kinase catalytic domain whose primary sequence is a hybrid between a serine/threonine kinase catalytic domain and a tyrosine kinase catalytic domain. Kinases containing the dual specificity kinase catalytic domain are capable of phosphorylating both serine/threonine and tyrosine residues. Preferably, a dual specificity kinase catalytic domain includes the following amino acid consensus sequence $X_9$-G-X-G-$X_2$-G-X-V-$X_{12}$-K-$X_{(10-19)}$-E-$X_{34}$-G-$X_{40}$-H-R-D-X-K-$X_2$-N-$X_{17}$-K-$X_2$-D-F-G-$X_{19}$-W-X-A-P-E-$X_{13}$ -W-$X_7$-E-$X_6$-P-$X_{36}$-C-W-$X_6$-R-P-X-F-$X_{14}$ (SEQ ID NO:19). Dual specificity kinase catalytic domains are described in, for example, Holzman L. B. et al. (1994) *J. Biol. Chem.* 269:30808–817, the contents of which are incorporated herein by reference. Amino acid residues 31–277 of the CSAPK-2 protein comprise a dual specificity kinase catalytic domain.

As used herein, the term "leucine zipper region" includes a protein domain which contains either leucine or isoleucine residues in every seventh position over a stretch of at least 20–30 amino acid residues, more preferably at least 20–25 amino acid residues, and most preferably at least 22 amino acid residues. Typically, the leucine zipper domain is rich in charged residues and forms a helical structure with a hydrophobic ridge of leucines or isoleucines down one face of the helix. The leucine zipper promotes dimerization through hydrophobic interactions between the leucine residues. Leucine zipper domains are described in, for example, Landschultz et al. (1988) *Science* 240: 1759–1764, the contents of which are incorporated herein by reference. Amino acid residues 294 to 322 of the CSAPK-2 protein comprise a leucine zipper region. Optionally, the leucine zipper region is found adjacent to a basic region. As used herein, the term "basic region" includes an amino acid sequence of 5–30, preferably 5–20, more preferably 5–15 amino acid residues in length, which is composed of a series of basic and hydrophobic amino acid residues, at either the N-terminus or the C-terminus of the leucine zipper region. For example, a 15 amino acid basic domain can contain at least 6, 8, or 10 basic residues and/or at least 1, 2, or 4 hydrophobic residues. Amino acid residues 407–421 of the CSAPK-2 protein comprise a basic region.

Isolated proteins of the present invention, preferably CSAPK-2 proteins, have an amino acid sequence sufficiently homologous to the amino acid sequence of SEQ ID NO:5 or are encoded by a nucleotide sequence sufficiently homologous to SEQ ID NO:4 or SEQ ID NO:6.

As used interchangeably herein a "CSAPK-2 activity", "biological activity of CSAPK-2" or "functional activity of CSAPK-2", refers to an activity exerted by a CSAPK-2 protein, polypeptide or nucleic acid molecule on a CSAPK-2 responsive cell or a CSAPK-2 protein substrate, as determined in vivo, or in vitro, according to standard techniques. The biological activity of CSAPK-2 is described herein.

Accordingly, another embodiment of the invention features isolated CSAPK-2 proteins and polypeptides having a CSAPK-2 activity. Preferred proteins are CSAPK-2 proteins having at least one dual specificity kinase catalytic domain and at least one ATP-binding region. Yet further preferred CSAPK-2 proteins have at least one dual specificity kinase catalytic domain, at least one ATP-binding region, and at least one leucine zipper region. Preferred proteins have at least one dual specificity kinase catalytic domain, at least one ATP-binding region and, preferably, a CSAPK-2 activity. Additional preferred proteins have at least one dual specificity kinase catalytic domain, at least one ATP-binding region and are, preferably, encoded by a nucleic acid molecule having a nucleotide sequence which hybridizes under stringent hybridization conditions to a nucleic acid molecule comprising the nucleotide sequence of SEQ ID NO:4 or SEQ ID NO:6.

The nucleotide sequence of the isolated human CSAPK-2 cDNA and the predicted amino acid sequence of the human CSAPK-2 polypeptide are shown in FIG. 2 and in SEQ ID NOs:4 and 5, respectively. A plasmid containing the nucleotide sequence encoding human CSAPK-2 was deposited with American Type Culture Collection (ATCC), 10801 University Boulevard, Manassas, Va. 20110-2209, on Oct. 27,1998 and assigned Accession Number 203306. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The CSAPK-2 gene, which is approximately 2120 nucleotides in length, encodes a protein having a molecular weight of approximately 52.3 kD and which is approximately 455 amino acid residues in length. The CSAPK-2 gene is expressed predominantly in muscle, e.g., skeletal or cardiac muscle.

C. The CSAPK-3 Nucleic Acid and Protein Molecules

In another embodiment, the isolated proteins of the present invention, preferably CSAPK-3 proteins, are identified based on the presence of at least one Ser/Thr kinase site and at least one ATP-binding region. The Ser/Thr kinase site and the ATP-binding region are described herein. Amino acid residues 5–164 of the CSAPK-3 protein comprise a Ser/Thr kinase domain.

Isolated proteins of the present invention, preferably CSAPK-3 proteins, have an amino acid sequence sufficiently homologous to the amino acid sequence of SEQ ID NO:8 or are encoded by a nucleotide sequence sufficiently homologous to SEQ ID NO:7 or SEQ ID NO:9.

As used interchangeably herein a "CSAPK-3 activity", "biological activity of CSAPK-3" or "functional activity of CSAPK-3", refers to an activity exerted by a CSAPK-3 protein, polypeptide or nucleic acid molecule on a CSAPK-3 responsive cell or a CSAPK-3 protein substrate as determined in vivo, or in vitro, according to standard techniques. The biological activity of CSAPK-3 is described herein.

Accordingly, another embodiment of the invention features isolated CSAPK-3 proteins and polypeptides having a CSAPK-3 activity. Preferred proteins are CSAPK-3 proteins having at least one Ser/Thr kinase site and at least one ATP-binding region. Additional preferred proteins have at least one Ser/Thr kinase site, at least one ATP-binding region, and, preferably a CSAPK-3 activity. Additional preferred proteins have at least one Ser/Thr kinase site and at least one ATP-binding region and are, preferably, encoded by a nucleic acid molecule having a nucleotide sequence which hybridizes under stringent hybridization conditions to a nucleic acid molecule comprising the nucleotide sequence of SEQ ID NO:7 or SEQ ID NO:9.

The nucleotide sequence of the isolated human CSAPK-3 cDNA and the predicted amino acid sequence of the human CSAPK-3 polypeptide are shown in FIG. 3 and in SEQ ID NOs:7 and 8, respectively. A plasmid containing the nucleotide sequence encoding human CSAPK-3 was deposited with American Type Culture Collection (ATCC), 10801 University Boulevard, Manassas, Va. 20110-2209, on Oct. 27,1998 and assigned Accession Number 203309. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The CSAPK-3 gene, which is approximately 2454 nucleotides in length, encodes a protein having a molecular weight of approximately 66.8 kD and which is approximately 581 amino acid residues in length. The CSAPK-3 gene is expressed predominantly in heart, skeletal muscle, brain, placenta, lung, liver, kidney, and pancreas.

D. The CSAPK-4 Nucleic Acid and Protein Molecules

In another embodiment, the isolated proteins of the present invention, preferably CSAPK-4 proteins, are identified based on the presence of at least one Ser/Thr kinase site and at least one ATP-binding region. The Ser/Thr kinase site and the ATP-binding region are described herein. Amino acid residues 11 to 75 of the CSAPK-4 protein comprise a Ser/Thr kinase domain.

Isolated proteins of the present invention, preferably CSAPK-4 proteins, have an amino acid sequence sufficiently homologous to the amino acid sequence of SEQ ID NO:11 or are encoded by a nucleotide sequence sufficiently homologous to SEQ ID NO:10 or SEQ ID NO:12.

As used interchangeably herein a "CSAPK-4 activity", "biological activity of CSAPK-4" or "functional activity of CSAPK-4", refers to an activity exerted by a CSAPK-4 protein, polypeptide or nucleic acid molecule on a CSAPK-4 responsive cell or a CSAPK-4 protein substrate as determined in vivo, or in vitro, according to standard techniques. The biological activity of CSAPK-4 is described herein.

Accordingly, another embodiment of the invention features isolated CSAPK-4 proteins and polypeptides having a CSAPK-4 activity. Preferred proteins are CSAPK-4 proteins having at least one Ser/Thr kinase site and at least one ATP-binding region. Additional preferred proteins have at least one Ser/Thr kinase site, at least one ATP-binding region, and, preferably a CSAPK-4 activity. Additional preferred proteins have at least one Ser/Thr kinase site and at least one ATP-binding region and are, preferably, encoded by a nucleic acid molecule having a nucleotide sequence which hybridizes under stringent hybridization conditions to a nucleic acid molecule comprising the nucleotide sequence of SEQ ID NO:10 or SEQ ID NO:12.

The nucleotide sequence of the isolated human CSAPK-4 cDNA and the predicted amino acid sequence of the human CSAPK-4 polypeptide are shown in FIG. 4 and in SEQ ID NOs: 10 and 11, respectively. A plasmid containing the nucleotide sequence 15 encoding human CSAPK-4 was deposited with American Type Culture Collection (ATCC), 10801 University Boulevard, Manassas, Va. 20110-2209, on Oct. 27,1998 and assigned Accession Number 203307. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The human CSAPK-4 gene, which is approximately 1864 nucleotides in length, encodes a protein having a molecular weight of approximately 18.4 kD and which is approximately 160 amino acid residues in length. The CSAPK-4 gene is expressed predominantly in skeletal muscle.

E. The CSAPK-5 Nucleic Acid and Protein Molecules

In another embodiment, the isolated proteins of the present invention, preferably CSAPK-5 proteins, are identified based on the presence of at least one Ser/Thr kinase site and at least one ATP-binding region. In yet another embodiment, the isolated proteins of the present invention, preferably CSAPK-5 proteins, are identified based on the presence of at least one Ser/Thr kinase site, and at least one ATP-binding region.

Isolated proteins of the present invention, preferably CSAPK-5 proteins, have an amino acid sequence sufficiently homologous to the amino acid sequence of SEQ ID NO:14 or are encoded by a nucleotide sequence sufficiently homologous to SEQ ID NO:13 or SEQ ID NO:15.

As used interchangeably herein a "CSAPK-5 activity", "biological activity of CSAPK-5" or "functional activity of CSAPK-5", refers to an activity exerted by a CSAPK-5 protein, polypeptide or nucleic acid molecule on a CSAPK-5 responsive cell or a CSAPK-5 protein substrate as determined in vivo, or in vitro, according to standard techniques. The biological activity of CSAPK-5 is described herein.

Accordingly, another embodiment of the invention features isolated CSAPK-5 proteins and polypeptides having a CSAPK-5 activity. Preferred proteins are CSAPK-5 proteins having at least one Ser/Thr kinase site and at least one ATP-binding region. Additional preferred proteins have at least one Ser/Thr kinase site, at least one ATP-binding region, and, preferably a CSAPK-5 activity. Additional preferred proteins have at least one Ser/Thr kinase site and at least one ATP-binding region and are, preferably, encoded by a nucleic acid molecule having a nucleotide sequence which hybridizes under stringent hybridization conditions to a nucleic acid molecule comprising the nucleotide sequence of SEQ ID NO:13 or SEQ ID NO:15.

The nucleotide sequence of the isolated human CSAPK-5 cDNA and the predicted amino acid sequence of the human CSAPK-5 polypeptide are shown in FIG. 5 and in SEQ ID NOs: 13 and 14, respectively. A plasmid containing the nucleotide sequence encoding human CSAPK-1 was deposited with American Type Culture Collection (ATCC), 10801 University Boulevard, Manassas, Va. 20110-2209, on Oct. 27,1998 and assigned Accession Number 203305. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. § 112.

The human CSAPK-5 gene, which is approximately 1333 nucleotides in length, encodes a protein having a molecular weight of approximately 51 kD and which is approximately 444 amino acid residues in length.

Various aspects of the invention are described in further detail in the following subsections:

I. Isolated Nucleic Acid Molecules

One aspect of the invention pertains to isolated nucleic acid molecules that encode CSAPK proteins or biologically active portions thereof, as well as nucleic acid fragments sufficient for use as hybridization probes to identify CSAPK-encoding nucleic acids (e.g., CSAPK mRNA) and fragments for use as PCR primers for the amplification or mutation of CSAPK nucleic acid molecules. As used herein, the term "nucleic acid molecule" is intended to include DNA molecules (e.g., cDNA or genomic DNA) and RNA molecules e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CSAPK nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, or a portion thereof, can be isolated using standard molecular biology techniques and the sequence information provided herein. For example, using all or portion of the nucleic acid sequence of SEQ ID NO:1, or the nucleotide sequence of SEQ ID NO:3, as a hybridization probe, CSAPK nucleic acid molecules can be isolated using standard hybridization and cloning techniques (e.g., as described in Sambrook, J., Fritsh, E. F., and Maniatis, *T. Molecular Cloning. A Laboratory Manual. 2nd, ed, Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15 can be isolated by the polymerase chain reaction (PCR) using synthetic oligonucleotide primers designed based upon the sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CSAPK nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the partial human CSAPK-1 cDNA. This cDNA comprises sequences encoding the human CSAPK-1 protein (i.e., "the coding region", from nucleotides 297–1202), as well as 5' untranslated sequences (nucleotides 1–296) and 3' untranslated sequences (nucleotides 1203–4137). Alternatively, the nucleic acid molecule can comprise only the coding region og SEQ ID NO:1 (e.g., nucleotides 297–1202, corresponding to SEQ ID NO:3).

In a preferred embodiment, an isolated nucleic acid molecule of the invention comprises the nucleotide sequence shown in SEQ ID NO:4. The sequence of SEQ ID NO:4 corresponds to the partial human CSAPK-2 cDNA. This cDNA comprises sequences encoding the partial human CSAPK-2 protein (i.e., "the coding region", from nucleotides 47–1411), as well as 5' untranslated sequences (nucleotides 1–46) and 3' untranslated sequences (nucleotides 1412–2120). Alternatively, the nucleic acid molecule can comprise only the coding region of SEQ ID NO:4 (e.g., nucleotides 47–1411, corresponding to SEQ ID NO:6).

In a preferred embodiment, an isolated nucleic acid molecule of the invention comprises the nucleotide sequence shown in SEQ ID NO:7. The sequence of SEQ ID NO:7 corresponds to the partial human CSAPK-3 cDNA. This cDNA comprises sequences encoding the partial human CSAPK-3 protein (i.e., "the coding region", from nucleotides 51–1793), as well as 5' untranslated sequences (nucleotides 1–50) and 3' untranslated sequences (nucleotides 1794–2454). Alternatively, the nucleic acid molecule can comprise only the coding region of SEQ ID NO:7 (e.g., nucleotides 51–1793, corresponding to SEQ ID NO:9).

In a preferred embodiment, an isolated nucleic acid molecule of the invention comprises the nucleotide sequence shown in SEQ ID NO:10. The sequence of SEQ ID NO:10 corresponds to the partial human CSAPK4 cDNA. This cDNA comprises sequences encoding the partial human CSAPK-4 protein (i.e., "the coding region", from nucleotides 275–754), as well as 5' untranslated sequences (nucleotides 1–274) and 3' untranslated sequences (nucleotides 755–1864). Alternatively, the nucleic acid molecule can comprise only the coding region of SEQ ID NO:10 (e.g., nucleotides 275–754, corresponding to SEQ ID NO:12).

In a preferred embodiment, an isolated nucleic acid molecule of the invention comprises the nucleotide sequence shown in SEQ ID NO:13. The sequence of SEQ ID NO:13 corresponds to the partial human CSAPK-5 cDNA. This cDNA comprises sequences encoding the partial human CSAPK-5 protein (i.e., "the coding region", from nucleotides 2–1333).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, or a portion of any of these nucleotide sequences. A nucleic acid molecule which is complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, respectively, such that it can hybridize to the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, respectively, thereby forming a stable duplex.

In still another preferred embodiment, an isolated nucleic acid molecule of the present invention comprises a nucleotide sequence which is at least about 50%, 54%, 55%, 60%,62%,65%,70%,75%,78%, 80%, 85%, 86%, 90%,95%, 97%, 98% or more homologous to the nucleotide sequence (e.g., to the entire length of the nucleotide sequence) shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, or a portion of any of these nucleotide sequences.

Moreover, the nucleic acid molecule of the invention can comprise only a portion of the nucleic acid sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, for example a fragment which can be used as a probe or primer or a fragment encoding a biologically active portion of a CSAPK protein. The nucleotide sequence determined from the cloning of the CSAPK gene allows for the generation of probes and primers designed for use in identifying and/or cloning other CSAPK family members, as well as CSAPK homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, of an anti-sense sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, or of a naturally occurring allelic variant or mutant of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15. In an exemplary embodiment, a nucleic acid molecule of the present invention comprises a nucleotide sequence which is at least 350, 400, 450, 500, 550, 600, 650, 700, 750, or 800 nucleotides in length and hybridizes under stringent hybridization conditions to a nucleic acid molecule of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15.

Probes based on the CSAPK nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a CSAPK protein, such as by measuring a level of a CSAPK-encoding nucleic acid in a sample of cells from a subject e.g., detecting CSAPK mRNA levels or determining whether a genomic CSAPK gene has been mutated or deleted.

A nucleic acid fragment encoding a "biologically-active portion of a CSAPK protein" can be prepared by isolating a portion of the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, which encodes a polypeptide having a CSAPK biological activity (the biological activities of the CSAPK proteins are described herein), expressing the encoded portion of the CSAPK protein (e.g., by recombinant expression in vitro) and assessing the activity of the encoded portion of the CSAPK protein.

The invention further encompasses nucleic acid molecules that differ from the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, due to the degeneracy of the genetic code and, thus, encode the same CSAPK proteins as those encoded by the nucleotide sequence shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15. In another embodiment, an isolated nucleic acid molecule of the invention has a nucleotide sequence encoding a protein having an amino acid sequence shown in SEQ ID NO:2, SEQ ID NO:5, SEQ ID NO:8, SEQ ID NO: 11, or SEQ ID NO:14.

In addition to the CSAPK nucleotide sequences shown in SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, it will be appreciated by those skilled in the art that DNA sequence polymorphisms that lead to changes in the amino acid sequences of the CSAPK proteins may exist within a population (e.g., the human population). Such genetic polymorphism in the CSAPK genes may exist among individuals within a population due to natural allelic variation. As used herein, the terms "gene" and "recombinant gene" refer to nucleic acid molecules which include an open reading frame encoding an CSAPK protein, preferably a mammalian CSAPK protein, and can further include non-coding regulatory sequences, and introns. Such natural allelic variations include both functional and non-functional CSAPK proteins and can typically result in 1–5% variance in the nucleotide sequence of a CSAPK gene. Any and all such nucleotide variations and resulting amino acid polymorphisms in CSAPK genes that are the result of natural allelic variation and that do not alter the functional activity of a CSAPK protein are intended to be within the scope of the invention.

Moreover, nucleic acid molecules encoding other CSAPK family members and, thus, which have a nucleotide sequence which differs from the CSAPK sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15 are intended to be within the scope of the invention. For example, another CSAPK cDNA can be identified based on the nucleotide sequence of human CSAPK. Moreover, nucleic acid molecules encoding CSAPK proteins from different species, and thus which have a nucleotide sequence which differs from the CSAPK sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15 are intended to be within the scope of the invention. For example, a mouse CSAPK cDNA can be identified based on the nucleotide sequence of a human CSAPK.

Nucleic acid molecules corresponding to natural allelic variants and homologues of the CSAPK cDNAs of the invention can be isolated based on their homology to the CSAPK nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15. In other embodiment, the nucleic acid is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at to least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes 15 in 0.2× SSC, 0.1% SDS at 50–65° C. Preferably, an isolated nucleic acid molecule of the invention that hybridizes under stringent conditions to the sequence of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CSAPK sequences that may exist in the population, the skilled artisan will further appreciate that changes can be introduced by mutation into the nucleotide sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15, thereby leading to changes in the amino acid sequence of the encoded CSAPK proteins, without altering the functional ability of the CSAPK proteins. For example, nucleotide substitutions leading to amino acid substitutions at "non-essential" amino acid residues can be made in the sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15. A "non-essential" amino acid residue is a residue that can be altered from the wild-type sequence of CSAPK (e.g., the sequence of SEQ ID NO:2, SEQ ID NO:5, SEQ ID NO:8, SEQ ID NO: 11, or SEQ ID NO:14) without altering the biological activity, whereas an "essential" amino acid residue is required for biological activity. For example, amino acid residues that are conserved among the CSAPK proteins of the present invention, are predicted to be particularly unamenable to alteration. Furthermore, additional amino acid residues that are conserved between the CSAPK proteins of the present invention and other CSAPK family members are not likely to be amenable to alteration.

Accordingly, another aspect of the invention pertains to nucleic acid molecules encoding CSAPK proteins that contain changes in amino acid residues that are not essential for activity. Such CSAPK proteins differ in amino acid sequence from SEQ ID NO:2, SEQ ID NO:5, SEQ ID NO:8, SEQ ID NO:11, or SEQ ID NO:14, yet retain biological activity. In one embodiment, the isolated nucleic acid molecule comprises a nucleotide sequence encoding a protein, wherein the protein comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:2, SEQ ID NO:5, SEQ ID NO:8, SEQ ID NO: 11, or SEQ ID NO:14 (e.g., the entire amino acid sequence of SEQ ID NO:2, SEQ ID NO:5, SEQ ID NO:8, SEQ ID NO: 11, or SEQ ID NO:14).

An isolated nucleic acid molecule encoding a CSAPK protein homologous to the protein of SEQ ID NO:2, SEQ ID NO:5, SEQ ID NO:8, SEQ ID NO:11, or SEQ ID NO:14 can be created by introducing one or more nucleotide substitutions, additions or deletions into the nucleotide sequence of SEQ ID NO:1, SEQ ID NO:4, SEQ ID NO:7, SEQ ID NO:10, or SEQ ID NO:15, respectively, such that one or more amino acid substitutions, additions or deletions are introduced into the encoded protein. Mutations can be introduced into SEQ ID NO:1, SEQ ID NO:4, SEQ ID NO:7, SEQ ID NO:10, or SEQ ID NO:15 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutimic acid) uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a CSAPK protein is preferably replaced with another amino acid residue from the same side chain family. Alternatively, in another embodiment, mutations can be introduced randomly along all or part of a CSAPK coding sequence, such as by saturation mutagenesis, and the resultant mutants can be screened for CSAPK biological activity to identify mutants that retain activity. Following mutagenesis of SEQ ID NO:1, SEQ ID NO:4, SEQ ID NO:7, SEQ ID NO:10, or SEQ ID NO:15, the encoded protein can be expressed recombinantly and the activity of the protein can be determined.

In a preferred embodiment, a mutant CSAPK protein can be assayed for the ability to: 1) regulate trasmission of signals from cellular receptors, e.g., cardiac cell growth factor receptors; 2) control entry of cells, e.g., cardiac cells, into mitosis; 3) modulate cellular differentiation; 4) modulate cell death; or 5) regulate cytoskeleton function, e.g., actin bundling.

In addition to the nucleic acid molecules encoding CSAPK proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CSAPK coding strand, or only to a portion thereof. In one embodiment, an antisense nucleic acid molecule is antisense to a "coding region" of the coding strand of a nucleotide sequence encoding CSAPK. The term "coding region" refers to the region of the nucleotide sequence comprising codons which are translated into amino acid residues (e.g., the coding region of human CSAPK-1 corresponds to SEQ ID NO:3). In another embodiment, the antisense nucleic acid molecule is antisense to a "noncoding region" of the coding strand of a nucleotide sequence encoding CSAPK. The term "noncoding region" refers to 5' and 3' sequences which flank the coding region that are not translated into amino acids (i.e., also referred to as 5' and 3' untranslated regions).

Given the coding strand sequences encoding CSAPK disclosed herein (e.g., SEQ ID NO:3, SEQ ID NO:6, SEQ ID NO:9, SEQ ID NO:12, or SEQ ID NO:15), antisense nucleic acids of the invention can be designed according to the rules of Watson and Crick base pairing. The antisense nucleic acid molecule can be complementary to the entire coding region of CSAPK mRNA, but more preferably is an oligonucleotide which is antisense to only a portion of the coding or noncoding region of CSAPK mRNA. For example, the antisense oligonucleotide can be complementary to the region surrounding the translation start site of CSAPK mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethyl aminomethyl-2-thiouridine, 5-carboxymethylamino methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CSAPK protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An (α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CSAPK mRNA transcripts to thereby inhibit translation of CSAPK mRNA. A ribozyme having specificity for a CSAPK-encoding nucleic acid can be designed based upon the nucleotide sequence of a CSAPK cDNA disclosed herein (i.e., SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15). For example, a derivative of a Tetrahymena L- 19 IVS RNA can be constructed in which the nucleotide sequence of the active site is complementary to the nucleotide sequence to be cleaved in a CSAPK-encoding mRNA. See, e.g., Cech et al. U.S. Pat. No. 4,987,071; and Cech et al. U.S. Pat. No. 5,116,742. Alternatively, CSAPK mRNA can be used to select a catalytic RNA having a specific ribonuclease activity from a pool of RNA molecules. See, e.g., Bartel, D. and Szostak, J. W. (1993) Science 261:1411–1418.

Alternatively, CSAPK gene expression can be inhibited by targeting nucleotide sequences complementary to the regulatory region of the CSAPK (e.g., the CSAPK promoter and/or enhancers) to form triple helical structures that prevent transcription of the CSAPK gene in target cells. See generally, Helene, C. (1991) Anticancer Drug Des. 6(6):569–84; Helene, C. et al. (1992) Ann. N. Y. Acad Sci. 660:27–36; and Maher, L. J. (1992) Bioassays 14(12):807–15.

In yet another embodiment, the CSAPK nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of CSAPK nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of CSAPK nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of CSAPK can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of CSAPK nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) Nucleic Acids Res. 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) Nucleic Acid Res. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. US. 86:6553–6556; Lemaitre et al. (1987) Proc. Natl. Acad. Sci. USA 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) Bio-Techniques 6:958–976) or intercalating agents. (See, e.g., Zon (1988) Pharm. Res. 5:539–549). To this end, the oligonucleotide may be conjugated to another molecule, (e.g., a peptide, hybridization triggered cross-to linking agent, transport agent, or hybridization-triggered cleavage agent).

II. Isolated CSAPK Proteins and Anti-CSAPK Antibodies

One aspect of the invention pertains to isolated CSAPK proteins, and biologically active portions thereof, as well as polypeptide fragments suitable for use as immunogens to raise anti-CSAPK antibodies. In one embodiment, native CSAPK proteins can be isolated from cells or tissue sources by an appropriate purification scheme using standard protein purification techniques. In another embodiment, CSAPK proteins are produced by recombinant DNA techniques. Alternative to recombinant expression, a CSAPK protein or polypeptide can be synthesized chemically using standard peptide synthesis techniques.

An "isolated" or "purified" protein or biologically active portion thereof is substantially free of cellular material or other contaminating proteins from the cell or tissue source from which the CSAPK protein is derived, or substantially free from chemical precursors or other chemicals when chemically synthesized. The language "substantially free of cellular material" includes preparations of CSAPK protein in which the protein is separated from cellular components of the cells from which it is isolated or recombinantly produced. In one embodiment, the language "substantially free of cellular material" includes preparations of CSAPK protein having less than about 30% (by dry weight) of non-CSAPK protein (also referred to herein as a "contaminating protein"), more preferably less than about 20% of non-CSAPK protein, still more preferably less than about 10% of non-CSAPK protein, and most preferably less than about 5% non-CSAPK protein. When the CSAPK protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CSAPK protein in which the protein is separated from chemical precursors or other chemicals which are involved in the synthesis of the protein. In one embodiment, the language "substantially free of chemical precursors or other chemicals" includes preparations of CSAPK protein having less than about 30% (by dry weight) of chemical precursors or non-CSAPK chemicals, more preferably less than about 20% chemical precursors or non-CSAPK chemicals, still more preferably less than about 10% chemical precursors or non-CSAPK chemicals, and most preferably less than about 5% chemical precursors or non-CSAPK chemicals.

Biologically active portions of a CSAPK protein include peptides comprising amino acid sequences sufficiently homologous to or derived from the amino acid sequence of the CSAPK protein, e.g., the amino acid sequence shown in SEQ ID NO:2, SEQ ID NO:5, SEQ ID NO:8, SEQ ID NO: 11, or SEQ ID NO:14, which include less amino acids than the full length CSAPK proteins, and exhibit at least one activity of a CSAPK protein.

Typically, biologically active portions comprise a domain or motif with at least one activity of the CSAPK protein. A biologically active portion of a CSAPK protein can be a polypeptide which is, for example, at least 10, 25, 50, 100 or more amino acids in length.

In a preferred embodiment, the CSAPK protein has an amino acid sequence shown in SEQ ID NO:2, SEQ ID NO:5, SEQ ID NO:g, SEQ ID NO:11, or SEQ ID NO:14. In other embodiments, the CSAPK protein is substantially homologous to SEQ ID NO:2, SEQ ID NO:5, SEQ ID NO:8, SEQ ID NO: 11, or SEQ ID NO:14, and retains the functional activity of the protein of SEQ ID NO:2, SEQ ID NO:5, SEQ ID NO:8, SEQ ID NO: 11, or SEQ ID NO:14, yet differs in amino acid sequence due to natural allelic variation or mutagenesis, as described in detail in subsection I above. Accordingly, in another embodiment, the CSAPK protein is a protein which comprises an amino acid sequence at least about 41%, 42%, 45%, 50%, 55%, 59%, 60%, 65%, 70%, 75%, 80%, 81%, 85%, 90%, 95%, 98% or more homologous to the amino acid sequence of SEQ ID NO:2, SEQ ID NO:5, SEQ ID NO:8, SEQ ID NO:11, or SEQ ID NO:14 (e.g., the entire amino acid sequence of SEQ ID NO:2, SEQ ID NO:5, SEQ ID NO:8, SEQ ID NO:11, or SEQ ID NO:14).

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the CSAPK amino acid sequence of SEQ ID NO:2, 5, 8, 11, or 14 having 177 amino acid residues, at least 80, preferably at least 100, more preferably at least 120, even more preferably at least 140, and even more preferably at least 150, 160 or 170 amino acid residues are aligned).

The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score =100, wordlength =12 to obtain nucleotide sequences homologous to CSAPK nucleic acid molecules of the invention. BLAST protein searches can be performed with the XBLAST program, score =50, wordlength =3 to obtain amino acid sequences homologous to CSAPK protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides CSAPK chimeric or fusion proteins. As used herein, a CSAPK "chimeric protein" or "fusion protein" comprises a CSAPK polypeptide operatively linked to a non-CSAPK polypeptide. An "CSAPK polypeptide" refers to a polypeptide having an amino acid sequence corresponding to CSAPK, whereas a "non-CSAPK polypeptide" refers to a polypeptide having an amino acid sequence corresponding to a protein which is not substantially homologous to the CSAPK protein, e.g., a protein which is different from the CSAPK protein and which is derived from the same or a different organism.

Within a CSAPK fusion protein the CSAPK polypeptide can correspond to all or a portion of a CSAPK protein. In a preferred embodiment, a CSAPK fusion protein comprises at least one biologically active portion of a CSAPK protein. In another preferred embodiment, a CSAPK fusion protein comprises at least two biologically active portions of a CSAPK protein. Within the fusion protein, the term "operatively linked" is intended to indicate that the CSAPK polypeptide and the non-CSAPK polypeptide are fused in-frame to each other. The non-CSAPK polypeptide can be fused to the N-terminus or C-terminus of the CSAPK polypeptide.

For example, in one embodiment, the fusion protein is a GST-CSAPK fusion protein in which the CSAPK sequences are fused to the C-terminus of the GST sequences. Such fusion proteins can facilitate the purification of recombinant CSAPK.

In another embodiment, the fusion protein is a CSAPK protein containing a heterologous signal sequence at its N-terminus. In certain host cells (e.g., mammalian host cells), expression and/or secretion of CSAPK can be increased through use of a heterologous signal sequence.

The CSAPK fusion proteins of the invention can be incorporated into pharmaceutical compositions and administered to a subject in vivo. The CSAPK fusion proteins can be used to affect the bioavailability of a CSAPK substrate. Use of CSAPK fusion proteins may be useful therapeutically for the treatment of cellular growth related disorders, e.g., cardiovascular disorers. Moreover, the CSAPK-fusion proteins of the invention can be used as immunogens to produce anti-CSAPK antibodies in a subject, to purify CSAPK ligands and in screening assays to identify molecules which inhibit the interaction of CSAPK with a CSAPK substrate.

Preferably, a CSAPK chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A CSAPK-encoding nucleic acid can be cloned into such an expression vector such that the fusion moiety is linked in-frame to the CSAPK protein.

The present invention also pertains to variants of the CSAPK proteins which function as either CSAPK agonists (mimetics) or as CSAPK antagonists. Variants of the CSAPK proteins can be generated by mutagenesis, e.g., discrete point mutation or truncation of a CSAPK protein. An agonist of the CSAPK proteins can retain substantially the same, or a subset, of the biological activities of the naturally occurring form of a CSAPK protein. An antagonist of a CSAPK protein can inhibit one or more of the activities of the naturally occurring form of the CSAPK protein by, for example, competitively modulating a cardiovascular system activity of a CSAPK protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the CSAPK protein.

In one embodiment, variants of a CSAPK protein which function as either CSAPK agonists (mimetics) or as CSAPK antagonists can be identified by screening combinatorial libraries of mutants, e.g., truncation mutants, of a CSAPK protein for CSAPK protein agonist or antagonist activity. In one embodiment, a variegated library of CSAPK variants is generated by combinatorial mutagenesis at the nucleic acid level and is encoded by a variegated gene library. A variegated library of CSAPK variants can be produced by, for example, enzymatically ligating a mixture of synthetic oligonucleotides into gene sequences such that a degenerate set of potential CSAPK sequences is expressible as individual polypeptides, or alternatively, as a set of larger fusion proteins (e.g., for phage display) containing the set of CSAPK sequences therein. There are a variety of methods which can be used to produce libraries of potential CSAPK variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CSAPK sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CSAPK protein coding sequence can be used to generate a variegated population of CSAPK fragments for screening and subsequent selection of variants of a CSAPK protein. In one embodiment, a library of coding sequence fragments can be generated by treating a double stranded PCR fragment of a CSAPK coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CSAPK protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CSAPK proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify CSAPK variants (Arkin and Yourvan (1992) *Proc. Nati. Acad. Sci. USA* 89:7811–7815; Delgrave et al. (1 993) *Protein Engineering* 6(3):327–331).

In one embodiment, cell based assays can be exploited to analyze a variegated CSAPK library. For example, a library of expression vectors can be transfected into a cell line which ordinarily synthesizes and secretes CSAPK. The transfected cells are then cultured such that CSAPK and a particular mutant CSAPK are secreted and the effect of expression of the mutant on CSAPK activity in cell supernatants can be detected, e.g., by any of a number of enzymatic assays. Plasmid DNA can then be recovered from the cells which score for inhibition, or alternatively, potentiation of CSAPK activity, and the individual clones further characterized.

An isolated CSAPK protein, or a portion or fragment thereof, can be used as an immunogen to generate antibodies that bind CSAPK using standard techniques for polyclonal and monoclonal antibody preparation. A full-length CSAPK protein can be used or, alternatively, the invention provides antigenic peptide fragments of CSAPK for use as immunogens. The antigenic peptide of CSAPK comprises at least 8 amino acid residues of the amino acid sequence shown in SEQ ID NO:2, SEQ ID NO:5, SEQ ID NO:8, SEQ ID NO:11, or SEQ ID NO:14 and encompasses an epitope of CSAPK such that an antibody raised against the peptide forms a specific immune complex with CSAPK. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of CSAPK that are located on the surface of the protein, e.g., hydrophilic regions.

A CSAPK immunogen typically is used to prepare antibodies by immunizing a suitable subject, (e.g., rabbit, goat, mouse or other mammal) with the immunogen. An appropriate immunogenic preparation can contain, for example, recombinantly expressed CSAPK protein or a chemically synthesized CSAPK polypeptide. The preparation can further include an adjuvant, such as Freund's complete or incomplete adjuvant, or similar immunostimulatory agent. Immunization of a suitable subject with an immunogenic CSAPK preparation induces a polyclonal anti-CSAPK antibody response.

Accordingly, another aspect of the invention pertains to anti-CSAPK antibodies. The term "antibody" as used herein refers to immunoglobulin molecules and immunologically active portions of immunoglobulin molecules, i.e., molecules that contain an antigen binding site which specifically binds (immunoreacts with) an antigen, such as CSAPK. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CSAPK. The term "monoclonal antibody" or "monoclonal antibody composition", as used herein, refers to a population of antibody molecules that contain only one species of an antigen binding site capable of immunoreacting with a particular epitope of CSAPK. A monoclonal antibody composition thus typically displays a single binding affinity for a particular CSAPK protein with which it immunoreacts.

Polyclonal anti-CSAPK antibodies can be prepared as described above by immunizing a suitable subject with a CSAPK immunogen. The anti-CSAPK antibody titer in the immunized subject can be monitored over time by standard techniques, such as with an enzyme linked immunosorbent assay (ELISA) using immobilized CSAPK. If desired, the antibody molecules directed against CSAPK can be isolated from the mammal (e.g., from the blood) and further purified by well known techniques, such as protein A chromatography to obtain the IgG fraction. At an appropriate time after immunization, e.g., when the anti-CSAPK antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. NatL. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lemer (1981) *Yale J. Biol. Med*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a CSAPK immunogen as described above, and the culture supernatants of the resulting hybridoma cells are screened to identify a hybridoma producing a monoclonal antibody that binds CSAPK.

Any of the many well known protocols used for fusing lymphocytes and immortalized cell lines can be applied for the purpose of generating an anti-CSAPK monoclonal antibody (see, e.g., G. Galfre et al. (1977) *Nature* 266:55052; Gefter et al. *Somatic Cell Genet.*, cited supra; Lemer, *Yale J. Biol. Med*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG") . Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CSAPK, e.g., using a standard ELISA assay.

Alternative to preparing monoclonal antibody-secreting hybridomas, a monoclonal anti-CSAPK antibody can be identified and isolated by screening a recombinant combinatorial immunoglobulin library (e.g., an antibody phage display library) with CSAPK to thereby isolate immunoglobulin library members that bind CSAPK. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/2079 1; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) Bio/Technology 9:1373–1377; Hoogenboom et al. (1991) Nuc. Acid Res. 19:4133–4137; Barbas et al. (1991) *Proc. NatL. Acad Sci. USA* 88:7978–7982; and McCafferty et al. *Nature* (1990) 348:552–554.

Additionally, recombinant anti-CSAPK antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Nati Acad Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoayan et al. (1988) *Science* 239:1534; and Beidler et al. (1988) *J. Immunol.* 141:4053–4060.

An anti-CSAPK antibody (e.g., monoclonal antibody) can be used to isolate CSAPK by standard techniques, such as affinity chromatography or immunoprecipitation. An anti-C SAPK antibody can facilitate the purification of natural CSAPK from cells and of recombinantly produced CSAPK expressed in host cells. Moreover, an anti-CSAPK antibody can be used to detect CSAPK protein (e.g., in a cellular lysate or cell supernatant) in order to evaluate the abundance and pattern of expression of the CSAPK protein. Anti-CSAPK antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidinabiotin and avidin/biotin; examples of suitable fluorescent materials include umbelliferone, fluorescein, fluorescein isothiocyanate, rhodarmine, dichorotriazinylamine fluorescein, dansyl chloride or phycoerythrin; an example of a luminescent material includes luminol; examples of bioluminescent materials include luciferase, luciferin, and aequorin, and examples of suitable radioactive ma terial include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a CSAPK protein (or a portion there of). As used here in, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are c apable of autonomous replication in a host cell into which they are in troduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., CSAPK proteins, mutant forms of CSAPK proteins, fusion proteins, and the like).

The recombinant expression vectors of the invention can be designed for expression of CSAPK proteins in prokaryotic or eukaryotic cells. For example, CSAPK proteins can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded tlherein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in CSAPK activity assays, (e.g., direct assays or competitive assays described in detail below), or to generate antibodies specific for CSAPK proteins, for example. In a preferred embodiment, a CSAPK fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann etal., (1988) *Gene* 69:301–315) and pET 11d (Studieretal., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the CSAPK expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (In Vitrogen Corp, San Diego, Calif.).

Alternatively, CSAPK proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kauftnan et al. (1987) *EMBO J.* 6:187–195). When used in mammalian cells, the expression vector's control fumctions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CSAPK mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics, Vol.* 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CSAPK protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G4 18, hygromycin and methotrexate. Nucleic acid encoding a selectable marker can be introduced into a host cell on the same vector as that encoding a CSAPK protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CSAPK protein. Accordingly, the invention further provides methods for producing a CSAPK protein using the host cells of the invention. In one embodiment, the method comprises culturing the host cell of invention (into which a recombinant expression vector encoding a CSAPK protein has been introduced) in a suitable medium such that a CSAPK protein is produced. In another embodiment, the method further comprises isolating a CSAPK protein from the medium or the host cell.

The host cells of the invention can also be used to produce non-human transgenic animals. For example, in one embodiment, a host cell of the invention is a fertilized oocyte or an embryonic stem cell into which CSAPK-coding sequences have been introduced. Such host cells can then be used to create non-human transgenic animals in which exogenous CSAPK sequences have been introduced into their genome or homologous recombinant animals in which endogenous CSAPK sequences have been altered. Such animals are useful for studying the function and/or activity of a CSAPK and for identifying and/or evaluating modulators of CSAPK activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CSAPK gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a CSAPK-encoding nucleic acid into the male pronuclei of a fertilized oocyte, e.g., by microinjection, retroviral infection, and allowing the oocyte to develop in a pseudopregnant female foster animal. The CSAPK cDNA sequence of SEQ ID NO:1, SEQ ID NO:4, SEQ ID NO:7, SEQ ID NO:10, or SEQ ID NO:13 can be introduced as a transgene into the genome of a non-human animal. Alternatively, a nonhuman homologue of a human CSAPK gene, such as a mouse or rat CSAPK gene, can be used as a transgene. Alternatively, a CSAPK gene homologue, such as another CSAPK family member, can be isolated based on hybridization to the CSAPK cDNA sequences of SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, or SEQ ID NO:15 (described further in subsection I above) and used as a transgene. Intronic sequences and polyadenylation signals can also be included in the transgene to increase the efficiency of expression of the transgene. A tissue-specific regulatory sequence(s) can be operably linked to a CSAPK transgene to direct expression of a CSAPK protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of a CSAPK transgene in its genome and/or expression of CSAPK mRNA in tissues or cells of the animals. A transgenic founder animal can then be used to breed additional animals carrying the transgene. Moreover, transgenic animals carrying a transgene encoding a CSAPK protein can further be bred to other transgenic animals carrying other transgenes.

To create a homologous recombinant animal, a vector is prepared which contains at least a portion of a CSAPK gene into which a deletion, addition or substitution has been introduced to thereby alter, e.g., functionally disrupt, the CSAPK gene. The CSAPK gene can be a human gene (e.g., the SEQ ID NO:1, SEQ ID NO:4, SEQ ID NO:7, SEQ ID NO:10, or SEQ ID NO:13), but more preferably, is a non-human homologue of a human CSAPK gene (e.g., a cDNA isolated by stringent hybridization with the nucleotide sequence of SEQ ID NO:1, SEQ ID NO:4, SEQ ID NO:7, SEQ ID NO:10, or SEQ ID NO:13). For example, a mouse CSAPK gene can be used to construct a homologous recombination vector suitable for altering an endogenous CSAPK gene in the mouse genome. In a preferred embodiment, the vector is designed such that, upon homologous recombination, the endogenous CSAPK gene is functionally disrupted (i.e., no longer encodes a functional protein; also referred to as a "knock out" vector). Alternatively, the vector can be designed such that, upon homologous recombination, the endogenous CSAPK gene is mutated or otherwise altered but still encodes a functional protein (e.g., the upstream regulatory region can be altered to thereby alter the expression of the endogenous CSAPK protein). In the homologous recombination vector, the altered portion of the CSAPK gene is flanked at its 5' and 3' ends by additional nucleic acid sequence of the CSAPK gene to allow for homologous recombination to occur between the exogenous CSAPK gene carried by the vector and an endogenous CSAPK gene in an embryonic stem cell. The additional flanking CSAPK nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced CSAPK gene has homologously recombined with the endogenous CSAPK gene are selected (see, e.g., Li, E. et al. (1992) *Cell* 69:915). The selected cells are then injected into a blastocyst of an animal (e.g., a mouse) to formn aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then beimplanted into asuitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The CSAPK nucleic acid molecules, CSAPK proteins, and anti-CSAPK antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CSAPK protein or anti-CSAPK antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermnint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No 5,328,470) or by stereotactic injection (see e.g., Chen et al. (1994) Proc. Natl. Acad Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express CSAPK protein (e.g., via a recombinant expression vector in a host cell in gene therapy applications), to detect CSAPK mRNA (e.g., in a biological sample) or a genetic alteration in a CSAPK gene, and to modulate CSAPK activity, as described further below. The CSAPK proteins can be used to treat disorders characterized by insufficient or excessive production of a CSAPK substrate or production of CSAPK inhibitors. In addition, the CSAPK proteins can be used to screen for naturally occurring CSAPK substrates, to screen for drugs or compounds which modulate CSAPK activity, as well as to treat disorders characterized by insufficient or excessive production of CSAPK protein or production of CSAPK protein forms which have decreased or aberrant activity compared to CSAPK wild type protein. Moreover, the anti-CSAPK antibodies of the invention can be used to detect and isolate CSAPK proteins, regulate the bioavailability of CSAPK proteins, and modulate CSAPK activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to CSAPK proteins, have a stimulatory or inhibitory effect on, for example, CSAPK expression or CSAPK activity, or have a stimulatory or inhibitory effect on, for example, the expression or activity of a CSAPK substrate.

In one embodiment, the invention provides assays for screening candidate or test compounds which are substrates of a CSAPK protein or polypeptide or biologically active portion thereof. In another embodiment, the invention provides assays for screening candidate or test compounds which bind to or modulate the activity of a CSAPK protein or polypeptide or biologically active portion thereof, e.g., modulate the ability of CSAPK to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat No. 5,223, 409), spores (Ladner U.S. Pat. No. 409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici(1991) J. Mol. Biol. 222:301–310); (Ladner supra.).

In another embodiment, an assay is a cell-based assay comprising contacting a cell expressing a CSAPK target molecule (e.g., a CSAPK phosphorylation substrate) with a test compound and determining the ability of the test compound to modulate (e.g. stimulate or inhibit) the activity of the CSAPK target molecule. Determining the ability of the test compound to modulate the activity of a CSAPK target molecule can be accomplished, for example, by determining the ability of the CSAPK protein to bind to or interact with the CSAPK target molecule, or by determining the ability of the CSAPK protein to phosphorylate the CSAPK target molecule.

The ability of the CSAPK protein to phosphorylate a CSAPK target molecule can be determined by, for example, an in vitro kinase assay. Briefly, a CSAPK target molecule, e.g., an molecule, e.g., an irrnunoprecipitated CSAPK target molecule from a cell line expressing such a molecule, can be incubated with the CSAPK protein and radioactive ATP, e.g., [$\gamma$-32$_P$] ATP, in a buffer containing $MgCl_2$ and $MnCl_2$, e.g., 10 mM $MgCl_2$ and 5 mM $MnCl_2$. Following the incubation, the immunoprecipitated CSAPK target molecule can be separated by SDS-polyacrylamide gel electrophoresis under reducing conditions, transferred to a membrane, e.g., a PVDF membrane, and autoradiographed. The appearance of detectable bands on the autoradiograph indicates that the CSAPK substrate has been phosphorylated. Phosphoaminoacid analysis of the phosphorylated substrate can also be performed in order to determine which residues on the CSAPK substrate are phosphorylated. Briefly, the radio-phosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the CSAPK protein to bind to or interact with a CSAPK target molecule can be accomplished by determining direct binding. Determining the ability of the CSAPK protein to bind to or interact with a CSAPK target molecule can be accomplished, for example, by coupling the CSAPK protein with a radioisotope or enzymatic label such that binding of the CSAPK protein to a CSAPK target molecule can be determined by detecting the labeled CSAPK protein in a complex. For example, CSAPK molecules, e.g., CSAPK proteins, can be labeled with $^{125}$I, $^{35}$S, $^{14}$C, or $^3$H, either directly or indirectly, and the radioisotope detected by direct counting of radioemmission or by scintillation counting. Alternatively, CSAPK molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between CSAPK and its target molecule, without the labeling of any of the interactants. For example, a microphysiometer can be used to detect the interaction of CSAPK with its target molecule without the labeling of either CSAPK or the target molecule. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the CSAPK protein to bind to or interact with a CSAPK target molecule can be accomplished by determining the activity of the target molecule. For example, the activity of the target molecule can be determined by detecting induction of a cellular second messenger of the target (e.g., intracellular Ca$^{2+}$, diacylglycerol, IP$_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which a CSAPK protein or biologically active portion thereof is contacted with a test compound and the ability of the test compound to bind to the CSAPK protein or biologically active portion thereof is determined. Binding of the test compound to the CSAPK protein can be determined either directly or indirectly as described above. In a preferred embodiment, the assay includes contacting the CSAPK protein or biologically active portion thereof with a known compound which binds CSAPK to form an assay mixture, contacting the assay mixture with a test compound, and determining the ability of the test compound to interact with a CSAPK protein, wherein determining the ability of the test compound to interact with a CSAPK protein comprises determining the ability of the test compound to preferentially bind to CSAPK or biologically active portion thereof as compared to the known compound.

In another embodiment, the assay is a cell-free assay in which a CSAPK protein or biologically active portion thereof is contacted with a test compound and the ability of the test compound to modulate (e.g., stimulate or inhibit) the activity of the CSAPK protein or biologically active portion thereof is determined. Determining the ability of the test compound to modulate the activity of a CSAPK protein can be accomplished, for example, by determining the ability of the CSAPK protein to bind to a CSAPK target molecule by one of the methods described above for determining direct binding. Determining the ability of the CSAPK protein to bind to a CSAPK target molecule can also be accomplished using a technology such as real-time Biomolecular Interaction Analysis (BIA). Sjolander, S. and Urbaniczky, C. (1991) Anal. Chem. 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BiAcore). Changes in the optical phenomenon of surface plasmon resonance (SPR) can be used as an indication of real-time reactions between biological molecules.

In an alternative embodiment, determining the ability of the test compound to modulate the activity of a CSAPK protein can be accomplished by determining the ability of the CSAPK protein to further modulate the activity of a CSAPK target molecule (e.g., a CSAPK mediated signal transduction pathway component). For example, the activity of the effector molecule on an appropriate target can be determined, or the binding of the effector to an appropriate target can be determined as previously described.

In yet another embodiment, the cell-free assay involves contacting a CSAPK protein or biologically active portion thereof with a known compound which binds the CSAPK protein to form an assay mixture, contacting the assay mixture with a test compound, and determining the ability of the test compound to interact with the CSAPK protein, wherein determining the ability of the test compound to interact with the CSAPK protein comprises determining the ability of the CSAPK protein to preferentially bind to or modulate the activity of a CSAPK target molecule.

The cell-free assays of the present invention are amenable to use of both soluble and/or membrane-bound forms of proteins (e.g., CSAPK proteins or biologically active portions thereof, or receptors to which CSAPK binds). In the case of cell-free assays in which a membrane-bound form a protein is used (e.g., a cell surface CSAPK receptor) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Tritong® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CSAPK or its target molecule to facilitate separation of complexed from uncomplexed forms of one or both of the proteins, as well as to accommodate automation of the assay. Binding of a test compound to a CSAPK protein, or interaction of a CSAPK protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/ CSAPK fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or CSAPK protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CSAPK binding or activity determined using standard techniques.

Other techniques for immobilizing proteins on matrices can also be used in the screening assays of the invention. For example, either a CSAPK protein or a CSAPK target molecule can be immobilized utilizing conjugation of biotin and streptavidin. Biotinylated CSAPK protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CSAPK protein or target molecules but which do not interfere with binding of the CSAPK protein to its target molecule can be derivatized to the wells of the plate, and unbound target or CSAPK protein trapped in the wells by antibody conjugation. Methods for detecting such complexes, in addition to those described above for the GST-immobilized complexes, include immunodetection of complexes using antibodies reactive with the CSAPK protein or target molecule, as well as enzyme-linked assays which rely on detecting an enzymatic activity associated with the CSAPK protein or target molecule.

In another embodiment, modulators of CSAPK expression are identified in a method wherein a cell is contacted with a candidate compound and the expression of CSAPK mRNA or protein in the cell is determined. The level of expression of CSAPK mRNA or protein in the presence of the candidate compound is compared to the level of expression of CSAPK mRNA or protein in the absence of the candidate compound. The candidate compound can then be identified as a modulator of CSAPK expression based on this comparison. For example, when expression of CSAPK mRNA or protein is greater (statistically significantly greater) in the presence of the candidate compound than in its absence, the candidate compound is identified as a stimulator of CSAPK mRNA or protein expression. Alternatively, when expression of CSAPK mRNA or protein is less (statistically significantly less) in the presence of the candidate compound than in its absence, the candidate compound is identified as an inhibitor of CSAPK mRNA or protein expression. The level of CSAPK mRNA or protein expression in the cells can be determined by methods described herein for detecting CSAPK mRNA or protein.

In yet another aspect of the invention, the CSAPK proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with CSAPK ("CSAPK-binding proteins" or "CSAPK-bp") and are involved in CSAPK activity. Such CSAPK-binding proteins are also likely to be involved in the propagation of signals by the CSAPK proteins or CSAPK targets as, for example, downstream elements of a CSAPK-mediated signaling pathway. Alternatively, such CSAPK-binding proteins are likely to be CSAPK inhibitors.

The two-hybrid system is based on the modular nature of most transcription factors, which consist of separable DNA-binding and activation domains. Briefly, the assay utilizes two different DNA constructs. In one construct, the gene that codes for a CSAPK protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CSAPK-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the CSAPK protein.

This invention further pertains to novel agents identified by the above-described screening assays. Accordingly, it is within the scope of this invention to further use an agent identified as described herein in an appropriate animal model. For example, an agent identified as described herein (e.g., a CSAPK modulating agent, an antisense CSAPK nucleic acid molecule, a CSAPK-specific antibody, or a CSAPK-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the CSAPK nucleotide sequences, described herein, can be used to map the location of the CSAPK genes on a chromosome. The mapping of the CSAPK sequences to chromosomes is an important first step in correlating these sequences with genes associated with disease.

Briefly, CSAPK genes can be mapped to chromosomes by preparing PCR primers (preferably 15–25 bp in length) from the CSAPK nucleotide sequences. Computer analysis of the CSAPK sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the CSAPK sequences will yield an amplified fragment.

Somatic cell hybrids are prepared by fuising somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CSAPK nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization (described in Fan, Y. et al. (1990) *Proc. Natl. Acad. Sci. USA*, 87:6223–27), pre-scrchromosomes, and pre-sew-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the CSAPK gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CSAPK sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for to identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CSAPK nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CSAPK nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, SEQ ID NO:10, or SEQ ID NO:13, can comfortably provide postive individual identification with a panel of perhaps 10 to 1,000 primers which each yield a noncoding amplified sequence of 100 bases. If predicted coding sequences, such as those in SEQ ID NO:3, SEQ ID NO:6, SEQ ID NO:9, SEQ ID NO:12, or SEQ ID NO:15 are used, a more appropriate number of primers for positive individual identification would be 500–2,000.

If a panel of reagents from CSAPK nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial CSAPK Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, SEQ ID NO:7, SEQ ID NO:10, or SEQ ID NO:13 are particularly appropriate for this use as greater numbers of polymorphisms occur in the noncoding regions, making it easier to differentiate individuals using this technique. Examples of polynucleotide reagents include the CSAPK nucleotide sequences or portions thereof, e.g., fragments derived from the noncoding regions of SEQ ID NO:1, SEQ ID NO:4, SEQ ID NO:7, SEQ ID NO:10, or SEQ ID NO:13, having a length of at least 20 bases, preferably at least 30 bases.

The CSAPK nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CSAPK probes can be used to identify tissue by species and/or by organ type.

In a similar fashion, these reagents, e.g., CSAPK primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining CSAPK protein and/or nucleic acid expression as well as CSAPK activity, in the context of a biological sample (e.g., blood, serum, cells, tissue) to thereby determine whether an individual is afflicted with a disease or disorder, or is at risk of developing a disorder, associated with aberrant CSAPK expression or activity. The invention also provides for prognostic (or predictive) assays for determining whether an individual is at risk of developing a disorder associated with CSAPK protein, nucleic acid expression or activity. For example, mutations in a CSAPK gene can be assayed in a biological sample. Such assays can be used for prognostic or predictive purpose to thereby phophylactically treat an individual prior to the onset of a disorder characterized by or associated with CSAPK protein, nucleic acid expression or activity.

Another aspect of the invention pertains to monitoring the influence of agents (e.g., drugs, compounds) on the expression or activity of CSAPK in clinical trials.

These and other agents are described in further detail in the following sections.

I. Diagnostic Assays

An exemplary method for detecting the presence or absence of CSAPK protein or nucleic acid in a biological sample involves obtaining a biological sample from a test subject and contacting the biological sample with a compound or an agent capable of detecting CSAPK protein or nucleic acid (e.g., mRNA, genomic DNA) that encodes CSAPK protein such that the presence of CSAPK protein or nucleic acid is detected in the biological sample. A preferred agent for detecting CSAPK mRNA or genomic DNA is a labeled nucleic acid probe capable of hybridizing to CSAPK mRNA or genomic DNA. The nucleic acid probe can be, for example, a human CSAPK nucleic acid, such as the nucleic acid of SEQ ID NO:1, SEQ ID NO:4, SEQ ID NO:7, SEQ ID NO:10, or SEQ ID NO: 13, or a portion thereof, such as an oligonucleotide of at least 15, 30, 50, 100, 250 or 500 nucleotides in length and sufficient to specifically hybridize under stringent conditions to CSAPK mRNA or genomic DNA. Other suitable probes for use in the diagnostic assays of the invention are described herein.

A preferred agent for detecting CSAPK protein is an antibody capable of binding to CSAPK protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CSAPK mRNA, protein, or genomic DNA in a biological sample in vitro as well as in vivo. For example, in vitro techniques for detection of CSAPK mRNA include Northern hybridizations and in situ hybridizations. In vitro techniques for detection of CSAPK protein include enzyme linked immunosorbent assays (ELISAs), Western blots, immunoprecipitations and immunofluorescence. In vitro techniques for detection of CSAPK genomic DNA include Southern hybridizations. Furthermore, in vivo techniques for detection of CSAPK protein include introducing into a subject a labeled anti-CSAPK antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting CSAPK protein, mRNA, or genomic DNA, such that the presence of CSAPK protein, mRNA or genomic DNA is detected in the biological sample, and comparing the presence of CSAPK protein, mRNA or genomic DNA in the control sample with the presence of CSAPK protein, mRNA or genomic DNA in the test sample.

The invention also encompasses kits for detecting the presence of CSAPK in a biological sample. For example, the kit can comprise a labeled compound or agent capable of detecting CSAPK protein or mRNA in a biological sample; means for determining the amount of CSAPK in the sample; and means for comparing the amount of CSAPK in the sample with a standard. The compound or agent can be packaged in a suitable container. The kit can further comprise instructions for using the kit to detect CSAPK protein or nucleic acid.

2. Prognostic Assays

The diagnostic methods described herein can furthermore be utilized to identify subjects having or at risk of developing a disease or disorder associated with aberrant CSAPK expression or activity. For example, the assays described herein, such as the preceding diagnostic assays or the following assays, can be utilized to identify a subject having or at risk of developing a disorder associated with CSAPK protein, nucleic acid expression or activity. Thus, the present invention provides a method for identifying a disease or disorder associated with aberrant CSAPK expression or activity in which a test sample is obtained from a subject and CSAPK protein or nucleic acid (e.g., mRNA, genomic DNA) is detected, wherein the presence of CSAPK protein or nucleic acid is diagnostic for a subject having or at risk of developing a disease or disorder associated with aberrant CSAPK expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CSAPK expression or activity. Thus, the present invention provides methods for determining whether a subject can be effectively treated with an agent for a disorder associated with aberrant CSAPK expression or activity in which a test sample is obtained and CSAPK protein or nucleic acid expression or activity is detected (e.g., wherein the abundance of CSAPK protein or nucleic acid expression or activity is diagnostic for a subject that can be administered the agent to treat a disorder associated with aberrant CSAPK expression or activity).

The methods of the invention can also be used to detect genetic alterations in a CSAPK gene, thereby determining if a subject with the altered gene is at risk for a disorder associated with the CSAPK gene. In preferred embodiments, the methods include detecting, in a sample of cells from the subject, the presence or absence of a genetic alteration characterized by at least one of an alteration affecting the integrity of a gene encoding a CSAPK-protein, or the mis-expression of the CSAPK gene. For example, such genetic alterations can be detected by ascertaining the existence of at least one of 1) a deletion of one or more nucleotides from a CSAPK gene; 2) an addition of one or more nucleotides to a CSAPK gene; 3) a substitution of one or more nucleotides of a CSAPK gene, 4) a chromosomal rearrangement of a CSAPK gene; 5) an alteration in the level of a messenger RNA transcript of a CSAPK gene, 6) aberrant modification of a CSAPK gene, such as of the methylation pattern of the genomic DNA, 7) the presence of a non-wild type splicing pattern of a messenger RNA transcript of a CSAPK gene, 8) a non-wild type level of a CSAPK-protein, 9) allelic loss of a CSAPK gene, and 10) inappropriate post-translational modification of a CSAPK-protein. As described herein, there are a large number of assay techniques known in the art which can be used for detecting alterations in a CSAPK gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad Sci. USA* 91:360–364), the latter of which can be particularly useful for detecting point mutations in the CSAPK-gene (see Abravaya et al. (1995) *Nucleic Acids Res* .23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CSAPK gene under conditions such that hybridization and amplification of the CSAPK-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad Sci. USA* 87:1874–1878), transcriptional amplification system (Kwoh, D. Y. et al., (1989) *Proc. Natl. Acad Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CSAPK gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in CSAPK can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in CSAPK can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CSAPK gene and detect mutations by comparing the sequence of the sample CSAPK with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the CSAPK gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type CSAPK sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CSAPK cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a CSAPK sequence, e.g., a wild-type CSAPK sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in CSAPK genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi (1992) *Genet Anal Tech Appl* 9:73–79). Single-stranded DNA fragments of sample and control CSAPK nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' eend of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CSAPK gene.

Furthermore, any cell type or tissue in which CSAPK is expressed may be utilized in the prognostic assays described herein.

3. Monitoring of Effects During Clinical Trials

Monitoring the influence of agents (e.g., drugs or compounds) on the expression or activity of a CSAPK protein can be applied not only in basic drug screening, but also in clinical trials. For example, the effectiveness of an agent determined by a screening assay as described herein to increase CSAPK gene expression, protein levels, or upregulate CSAPK activity, can be monitored in clinical trials of subjects exhibiting decreased CSAPK gene expression, protein levels, or downregulated CSAPK activity. Alternatively, the effectiveness of an agent determined by a screening assay to decrease CSAPK gene expression, protein levels, or downregulate CSAPK activity, can be monitored in clinical trials of subjects exhibiting increased CSAPK gene expression, protein levels, or upregulated CSAPK activity. In such clinical trials, the expression or activity of a CSAPK gene, and preferably, other genes that have been implicated in a disorder can be used as a "read out" or markers of the phenotype of a particular cell.

For example, and not by way of limitation, genes, including CSAPK, that are modulated in cells by treatment with an agent (e.g., compound, drug or small molecule) which modulates CSAPK activity (e.g., identified in a screening assay as described herein) can be identified. Thus, to study the effect of agents on a CSAPK associated disorder, for example, in a clinical trial, cells can be isolated and RNA prepared and analyzed for the levels of expression of CSAPK and other genes implicated in the CSAPK associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CSAPK or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CSAPK protein, mRNA, or genomic DNA in the pre-administration sample; (iii) obtaining one or more post-administration samples from the subject; (iv) detecting the level of expression or activity of the CSAPK protein, mRNA, or genomic DNA in the post-administration samples; (v) comparing the level of expression or activity of the CSAPK protein, mRNA, or genomic DNA in the pre-administration sample with the CSAPK protein, mRNA, or genomic DNA in the post administration sample or samples; and (vi) altering the administration of the agent to the subject accordingly. For example, increased administration of the agent may be desirable to increase the expression or activity of CSAPK to higher levels than detected, i.e., to increase the effectiveness of the agent. Alternatively, decreased administration of the agent may be desirable to decrease expression or activity of CSAPK to lower levels than detected, i.e. to decrease the effectiveness of the agent. According to such an embodiment, CSAPK expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant CSAPK expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the CSAPK molecules of the present invention or CSAPK modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant CSAPK expression or activity, by administering to the subject a CSAPK or an agent which modulates CSAPK expression or at least one CSAPK activity. Subjects at risk for a disease which is caused or contributed to by aberrant CSAPK expression or activity can be identified by, for example, any or a combination of diagnostic or prognostic assays as described herein. Administration of a prophylactic agent can occur prior to the manifestation of symptoms characteristic of the CSAPK aberrancy, such that a disease or disorder is prevented or, alternatively, delayed in its progression. Depending on the type of CSAPK aberrancy, for example, a CSAPK, CSAPK agonist or CSAPK antagonist agent can be used for treating the subject. The appropriate agent can be determined based on screening assays described herein.

2. Therapeutic Methods

Another aspect of the invention pertains to methods of modulating CSAPK expression or activity for therapeutic purposes. Accordingly, in an exemplary embodiment, the modulatory method of the invention involves contacting a cell with a CSAPK or agent that modulates one or more of the activities of CSAPK protein activity associated with the cell. An agent that modulates CSAPK protein activity can be an agent as described herein, such as a nucleic acid or a protein, a naturally-occurring target molecule of a CSAPK protein (e.g., a CSAPK phosphorylation substrate), a CSAPK antibody, a CSAPK agonist or antagonist, a peptidomimetic of a CSAPK agonist or antagonist, or other small molecule. In one embodiment, the agent stimulates one or more CSAPK activities. Examples of such stimulatory agents include active CSAPK protein and a nucleic acid molecule encoding CSAPK that has been introduced into the cell. In another embodiment, the agent inhibits one or more CSAPK activites. Examples of such inhibitory agents include antisense CSAPK nucleic acid molecules, anti-CSAPK antibodies, and CSAPK inhibitors. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a CSAPK protein or nucleic acid molecule. In one embodiment, the method involves administering an agent (e.g., an agent identified by a screening assay described herein), or combination of agents that modulates (e.g., upregulates or downregulates) CSAPK expression or activity. In another embodiment, the method involves administering a CSAPK protein or nucleic acid molecule as therapy to compensate for reduced or aberrant CSAPK expression or activity.

Stimulation of CSAPK activity is desirable in situations in which CSAPK is abnormally downregulated and/or in which increased CSAPK activity is likely to have a beneficial effect. For example, stimulation of CSAPK activity is desirable in situations in which a CSAPK is downregulated and/or in which increased CSAPK activity is likely to have a beneficial effect. Likewise, inhibition of CSAPK activity is desirable in situations in which CSAPK is abnormally upregulated and/or in which decreased CSAPK activity is likely to have a beneficial effect.

3. Pharmacogenomics

The CSAPK molecules of the present invention, as well as agents, or modulators which have a stimulatory or inhibitory effect on CSAPK activity (e.g., CSAPK gene expression) as identified by a screening assay described herein can be administered to individuals to treat (prophylactically or therapeutically) disorders (e.g, cardiovascular disorders such as congestive heart failure) associated with aberrant CSAPK activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a CSAPK molecule or CSAPK modulator as well as tailoring the dosage and/or therapeutic regimen of treatment with a CSAPK molecule or CSAPK modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11) :983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonarnides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict a drug response. According to this method, if a gene that encodes a drug target is known (e.g., a CSAPK protein or CSAPK receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a CSAPK molecule or CSAPK modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a CSAPK molecule or CSAPK modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

IDENTIFICATION AND CHARACTERIZATION OF HUMAN CSAPK cDNA

In this example, the identification and characterization of the genes encoding human CSAPK-1, CSAPK-2, CSAPK-3, CSAPK-4, and CSAPK-5 (also referred to as b004a10, b086g01, b007e05, b002d04, and b155a01, respectively) is described.

Isolation of the human CSAPK cDNA

The invention is based, at least in part, on the discovery of five human genes encoding members of the CSAPK family. The human CSAPK family members were isolated from cDNA libraries which were prepared from tissue obtained from subjects suffering from congestive heart failure of ischemic and idiopathic origin. Briefly, a cardiac tissue sample was obtained from a biopsy of a patient suffering from congestive heart failure. mRNA was isolated from the cardiac tissue and a cDNA library was prepared therefrom using art known methods (described in, for example, *Molecular Cloning A Laboratory Manual,* 2nd Ed., ed. by Sambrook, Fritsch and Maniatis (Cold Spring Harbor Laboratory Press: 1989). Positive clones were isolated following comparison to homologs in public protein databases, including a comparison with known kinases and/or examination of the sequence for protein motifs of kinases.

The sequences of the positive clones were determined and found to contain open reading frames. The nucleotide sequence encoding the human CSAPK-1 protein is shown in FIG. 1 and is set forth as SEQ ID NO:1. The protein encoded by this nucleic acid comprises about 302 amino acids and has the amino acid sequence shown in FIG. 1 and set forth as SEQ ID NO:2. The coding region (open reading frame) of SEQ ID NO:1 is set forth as SEQ ID NO:3. The clone comprising the entire coding region of human CSAPK-1 was deposited with the American Type Culture Collection (ATCC®), 10801 University Boulevard, Manassas, Va. 20110-2209, on , Oct. 27, 1998, and assigned Accession No. 203308.

The nucleotide sequence encoding the human CSAPK-2 protein is shown in FIG. 2 and is set forth as SEQ ID NO:4. The protein encoded by this nucleic acid comprises about 455 amino acids and has the amino acid sequence shown in FIG. 2 and set forth as SEQ ID NO:5. The coding region (open reading frame) of SEQ ID NO:4 is set forth as SEQ ID NO:6. The clone comprising the entire coding region of human CSAPK-2 was deposited with the American Type Culture Collection (ATCC®), 10801 University Boulevard, Manassas, Va. 20110-2209, on Oct. 27, 1998, and assigned Accession No. 203306.

The nucleotide sequence encoding the human CSAPK-3 protein is shown in FIG. 3 and is set forth as SEQ ID NO:7. The protein encoded by this nucleic acid comprises about 581 amino acids and has the amino acid sequence shown in FIG. 3 and set forth as SEQ ID NO:8. The coding region (open reading frame) of SEQ ID NO:7 is set forth as SEQ ID NO:9. The clone comprising the entire coding region of human CSAPK-3 was deposited with the American Type Culture Collection (ATCC®), 10801 University Boulevard, Manassas, Va. 20110-2209, on Oct. 27, 1998, and assigned Accession No. 203309.

The nucleotide sequence encoding the human CSAPK-4 protein is shown in FIG. 4 and is set forth as SEQ ID NO:10. The protein encoded by this nucleic acid comprises about 160 amino acids and has the amino acid sequence shown in FIG. 4 and set forth as SEQ ID NO: 11. The coding region (open reading frame) of SEQ ID NO:10 is set forth as SEQ ID NO:12. The clone comprising the entire coding region of human CSAPK-4 was deposited with the American Type Culture Collection (ATCC®), 10801 University Boulevard, Manassas, Va. 20110-2209, on Oct. 27, 1998, and assigned Accession No. 203307.

The nucleotide sequence encoding the human CSAPK-5 protein is shown in FIG. 5 and is set forth as SEQ ID NO:13. The protein encoded by this nucleic acid comprises about 444 amino acids and has the amino acid sequence shown in FIG. 5 and set forth as SEQ ID NO:14. The coding region (open reading frame) of SEQ ID NO:13 is set forth as SEQ ID NO:15.

Analysis of human CSAPK Molecule

A BLASTN 1.4.9 search, using a score of 100 and a word length of 12 (Altschul et al. (1990) *J. Mol. Biol.* 215:403) of the nucleotide sequence of human CSAPK-1 revealed that CSAPK-1 is similar to the human protein kinase HPK-1 coding sequence (Accession No. V23831). This nucleic acid molecule is approximately 70% identical to CSAPK-1, over nucleotides 388–1214.

CSAPK-2 is similar to the human MST mRNA for serine/threonine kinase (Accession No. Z48615). This nucleic acid molecule is approximately 54% identical to CSAPK-2, over nucleotides 482–805.

CSAPK-3 is similar to the human cDNA clone IMAGE: 1257327 (Accession No. AA746653). This nucleic acid molecule is approximately 99% identical to CSAPK-3, over nucleotides 2068–2430.

CSAPK-4 is similar to the Mus musculus cDNA clone 902193 (Accession No. AA516800) This nucleic acid molecule is approximately 86% identical to CSAPK-4, over nucleotides 321–755.

CSAPK-5 is similar to the non-annotated human mRNA for KIAA0551 protein (Accession No. AB011123). This nucleic acid molecule is approximately 100% identical to CSAPK-5, over nucleotides 1–1333.

Tissue Distribution of CSAPK mRNA

This Example describes the tissue distribution of CSAPK mRNA, as determined by Northern blot hybridizations.

Northern blot hybridizations with the various RNA samples were performed under standard conditions and washed under stringent conditions, i.e., 0.2×SSC at 65° C. The DNA probe was radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations.

CSAPK-1 message was detected predominantly in the heart, skeletal muscle, or the placenta. CSAPK-2 message was detected predominantly in muscle, e.g., skeletal or cardiac muscle. CSAPK-3 message was detected predominantly in heart, skeletal muscle, brain, placenta, lung, liver, kidney, and pancreas. CSAPK-4 message was detected predominantly in skeletal muscle.

Example 2

EXPRESSION OF RECOMBINANT CSAPK PROTEIN IN BACTERIAL CELLS

In this example, CSAPK is expressed as a recombinant glutathione-S-transferase (GST) fusion polypeptide in *E. coli* and the fusion polypeptide is isolated and characterized. Specifically, CSAPK is fused to GST and this fusion polypeptide is expressed in *E. coli*, e.g., strain PEB199. Expression of the GST-CSAPK fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 3

EXPRESSION OF RECOMBINANT CSAPK PROTEIN IN COS CELLS

To express the CSAPK gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire CSAPK protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the CSAPK DNA sequence is amplified by PCR using two primers. The 5' primer contains the restriction site of interest followed by approximately twenty nucleotides of the CSAPK coding sequence starting from the initiation codon; the 3' end sequence contains complementary sequences to the other restriction site of interest, a translation stop codon, the HA tag or FLAG tag and the last 20 nucleotides of the CSAPK coding sequence. The PCR amplified fragment and the pCDNA/Amp vector are digested with the appropriate restriction enzymes and the vector is dephosphorylated using the ClAP enzyme (New England Biolabs, Beverly, Mass.). Preferably the two restriction sites chosen are different so that the CSAPK gene is inserted in the correct orientation. The ligation mixture is transformed into *E. coli* cells (strains HB 101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the CSAPK-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the CSAPK polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the CSAPK coding sequence is cloned directly into the polylinker of the pCDNA/Amp vector using the appropriate restriction sites. The resulting plasmid is transfected into COS cells in the manner described above, and the expression of the CSAPK polypeptide is detected by radiolabelling and immunoprecipitation using a CSAPK specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide comprising the amino acid sequence of SEQ ID NO:2.

2. An isolated polypeptide consisting of the amino acid sequence of SEQ ID NO:2.

3. An isolated naturally occurring allerlic variant of a polypeptide comprising the amino acid sequence of SEQ ID NO:2 wherein the naturally occurring allelic variant of the polypeptide is encoded by a nucleic acid molecule which hybridizes to a complement of a nucleic acid molecule consisting of SEQ ID NO:1 or 3, in 6×SSC at 45° C., followed by one or more washes in 0.2×SSC, 0.1% SDS at 65° C., and wherein the naturally occuring alluelic vatiant of the polypeptide is at least 302 amino acids in length.

4. An isolated naturally occurring allelic variant of a polypeptide consisting of the amino acid sequence of SEQ ID NO:2, wherein the naturally occuring allelic variant of the polypepiide is encoded by a nucleic acid molecule which hybridizes to a complement of a nucleic acid molecule consisting of SEQ ID NO:1 or 3, in 6×SSC at 45° C., followed by one or more washes in 0.2×SSC, 0.1% SDS at 65° C., and wherein the naturally occurring allelic variant of the polypeptide is at least 302 amino acids in length.

5. An isolated polypeptide which is encoded by a nucleic acid molecule comprising a nucleotide sequence which is at least 98% identical to a nucleic acid comprising the nucleotide sequence of SEQ ID NO:1 or 3, wherein the polypeptide is at least 302 amino acids in length.

6. An isolated polypeptide which is encoded by a nucleic acid molecule consisting of a nucleotide sequence which is at least 98% identical to a nucleic acid consisting of the nucleotide sequence of SEQ ID NO:1 or 3, wherein the polypeptide is at least 302 amino acids in length.

7. The polypeptide of claim 1 further comprising heterologous amino acid sequences.

8. The polypeptide of claim 2 further comprising heterologous amino acid sequences.

9. The polypeptide of claim 3 further comprising heterologous amino acid sequences.

10. The polypeptide of claim 4 further comprising heterologous amino acid sequences.

11. The polypeptide of claim 5 further comprising heterologous amino acid sequences.

12. The polypeptide of claim 6 further comprising heterologous amino acid sequences.

13. An isolated polypeptide which is encoded by the nucleotide sequence of the human DNA insert of the plasmid deposited with ATCC as Accession Number 203308.

* * * * *

UNITED STATES PATENT AND TRADEMARK OFFICE
CERTIFICATE OF CORRECTION

PATENT NO.: 6,153,417

DATED : November 28, 2000

INVENTOR(S): Susan Acton

It is certified that error appears in the above-identified patent and that said Letters Patent is hereby corrected as shown below:

At column 105, line 49, please delete "allerlic" and insert -- allelic--"
At column 105, line 56, please delete "alluelic" and insert -- allelic--"
At column 105, line 56, please delete "vatiant" and insert -- variant --"
At column 105, line 61, please delete "polypepiide" and insert -- polypeptide--"
At column 105, line 63, please delete "morc" and insert -- more--"

Signed and Sealed this

Fifteenth Day of May, 2001

Attest:

NICHOLAS P. GODICI

*Attesting Officer*   Acting Director of the United States Patent and Trademark Office